US012747275B2

(12) United States Patent
Shen et al.

(10) Patent No.: US 12,747,275 B2
(45) Date of Patent: Sep. 29, 2026

(54) FUSION POLYPEPTIDE AND POLYPEPTIDE DIMER, AND USE THEREOF

(71) Applicant: Nanjing Normal University, Nanjing (CN)

(72) Inventors: Jian Shen, Nanjing (CN); Jiahong Zhou, Nanjing (CN)

(73) Assignee: Nanjing Normal University, Nanjing (CN)

( * ) Notice: Subject to any disclaimer, the term of this patent is extended or adjusted under 35 U.S.C. 154(b) by 745 days.

(21) Appl. No.: 18/004,634

(22) PCT Filed: Jul. 8, 2021

(86) PCT No.: PCT/CN2021/105187

§ 371 (c)(1),
(2) Date: Jan. 6, 2023

(87) PCT Pub. No.: WO2022/007885

PCT Pub. Date: Jan. 13, 2022

(65) Prior Publication Data

US 2023/0322882 A1 Oct. 12, 2023

(30) Foreign Application Priority Data

Jul. 8, 2020 (CN) ........................ 202010650886.X
Jul. 8, 2020 (CN) ........................ 202010651373.0

(51) Int. Cl.
*C07K 14/55* (2006.01)
*A61K 38/00* (2006.01)
(Continued)

(52) U.S. Cl.
CPC .......... *C07K 14/55* (2013.01); *C07K 14/5443* (2013.01); *C12N 15/63* (2013.01); *A61K 38/00* (2013.01); *C07K 2319/31* (2013.01)

(58) Field of Classification Search
None
See application file for complete search history.

(56) References Cited

U.S. PATENT DOCUMENTS 9,359,415 B2 * 6/2016 Alvarez ................ C07K 14/55
2014/0044675 A1 2/2014 Hosse et al.
(Continued)

FOREIGN PATENT DOCUMENTS

CN 104507504 A 4/2015
CN 110325205 A 10/2019
(Continued)

OTHER PUBLICATIONS

Berger, et al. Fusion protein technologies for biopharmaceuticals: applications and challenges. mAbs (2015), 7:3, p. 456-460.*
(Continued)

*Primary Examiner* — Joanne Hama
*Assistant Examiner* — Jami Michelle Gurley
(74) *Attorney, Agent, or Firm* — Stites & Harbison PLLC; Patrick M. Torre

(57) ABSTRACT

The present invention provides a fusion polypeptide, comprising a carrier protein and a polypeptide of interest, wherein the carrier protein has a plurality of coil domains linked by a ring, the polypeptide of interest is inserted in the ring of the carrier protein, and the carrier protein masks a site of interest on the polypeptide of interest, thereby blocking the accessibility of the site. The present invention also provides a polypeptide dimer, comprising a first polypeptide and a second polypeptide, wherein the first polypeptide comprises a first dimerization domain and a polypeptide of interest, the second polypeptide comprises a second dimerization domain and a binding domain, and the binding domain can bind to a site of interest on the polypeptide of interest. The present invention also provides a polynucle-
(Continued)

otide and a vector encoding the fusion polypeptide and polypeptide dimer, and a host cell comprising the polynucleotide and/or vector. Furthermore, the present invention also provides use of the fusion polypeptide and polypeptide dimer of the present invention in the treatment of cancer and/or the activation of immune cells.

6 Claims, 14 Drawing Sheets

Specification includes a Sequence Listing.

(51) Int. Cl.
*C07K 14/54* (2006.01)
*C12N 15/63* (2006.01)

(56) References Cited

U.S. PATENT DOCUMENTS

| | | | |
|---|---|---|---|
| 2015/0218260 | A1 | 8/2015 | Klein et al. |
| 2019/0352363 | A1 | 11/2019 | Seidel et al. |
| 2020/0040052 | A1 | 2/2020 | Winston et al. |

FOREIGN PATENT DOCUMENTS

| | | | |
|---|---|---|---|
| CN | 110724198 | A | 1/2020 |
| WO | WO 03/060071 | A2 | 7/2003 |
| WO | WO 03/066085 | A1 | 8/2003 |
| WO | WO 2015/036579 | A1 | 3/2015 |
| WO | WO2019222283 | A1 | 11/2019 |

OTHER PUBLICATIONS

Bendezu, et al. Spontaneous Cdc42 polarization independent of GDI-mediated extraction and actin-based trafficking. PLOS Biology (2015), 13:4, p. 1-30.*

Goedhart. Fluorescent proteins 101: GFP fusion proteins—Making the right connection. Addgene (2019), p. 1-10 Internet—https://blog.addgene.org/gfp-fusion-proteins-making-the-right-connection.*

Dijkstra et al. Identification of a gene for an ancient cytokine, interleukin 15-like, in mammals; interleukins 2 and 15 co-evolved with this third family member, all sharing binding motifs for IL-15Rα. Immunogenetics (2014), 66:93, p. 93-103.*

Sugio, et al. Crystal structure of human serum albumin at 2.5 Å resolution. Protein Engineering (1999), 12:6, p. 439-446.*

Adabi, et al., Evaluation of an Albumin-Binding Domain Protein Fused to Recombinant Human IL-2 and Its Effects on the Bioactivity and Serum Half-Life of the Cytokine'; Iranian Biomedical Journal 21(2): 77-83 Mar. 2017.

Varma, et al., Regulatory T Cell Selective IL-2-Fc Fusion Proteins for the Treatment of Autoimmune Diseases; Blood (2018) 132 (Supplement 1): 3709.

Ward, et al., IL-2/CD25: A Long-Acting Fusion Protein That Promotes Immune Tolerance by Selectively Targeting the IL-2 Receptor on Regulatory T Cells; J Immunol published online Oct. 3, 2018.

* cited by examiner structural model

SDS-PAGE analytic sieve chromatography structural model

SDS-PAGE analytic sieve chromatography structural model

SDS-PAGE analytic sieve chromatography cellular activity assay cellular activity assay

SEQUENCE LISTING

```
<160> NUMBER OF SEQ ID NOS: 34

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150


<210> SEQ ID NO 2
<211> LENGTH: 126
<212> TYPE: PRT
<213> ORGANISM: Artificial Sequence
<220> FEATURE:
<223> OTHER INFORMATION: IL-2-1
```

<400> SEQUENCE: 2

Arg Asp Leu Ile Ser Asn Ile Asn Val Ile Val Leu Glu Leu Lys Gly
1 5 10 15

Ser Glu Thr Thr Phe Met Cys Glu Tyr Ala Asp Glu Thr Ala Thr Ile
20 25 30

Val Glu Phe Leu Asn Arg Trp Ile Thr Phe Ser Gln Ser Ile Ile Ser
35 40 45

Thr Leu Thr Gly Ser Gly Pro Ala Ser Ser Ser Thr Lys Lys Thr Gln
50 55 60

Leu Gln Leu Glu His Leu Leu Leu Asp Leu Gln Met Ile Leu Asn Gly
65 70 75 80

Ile Asn Asn Tyr Lys Asn Pro Lys Leu Thr Arg Met Leu Thr Phe Lys
85 90 95

Phe Tyr Met Pro Lys Lys Ala Thr Glu Leu Lys His Leu Gln Cys Leu
100 105 110

Glu Glu Glu Leu Lys Pro Leu Glu Glu Val Leu Asn Leu Ala
115 120 125

<210> SEQ ID NO 3
<211> LENGTH: 135
<212> TYPE: PRT
<213> ORGANISM: Artificial Sequence
<220> FEATURE:
<223> OTHER INFORMATION: IL-2-2

<400> SEQUENCE: 3

Leu Thr Arg Met Leu Thr Phe Lys Phe Tyr Met Pro Lys Lys Ala Thr
1 5 10 15

Glu Leu Lys His Leu Gln Cys Leu Glu Glu Glu Leu Lys Pro Leu Glu
20 25 30

Glu Val Leu Asn Leu Ala Gln Ser Lys Asn Phe His Leu Arg Pro Arg
35 40 45

Asp Leu Ile Ser Asn Ile Asn Val Ile Val Leu Glu Leu Lys Gly Ser
50 55 60

Glu Thr Thr Phe Met Cys Glu Tyr Ala Asp Glu Thr Ala Thr Ile Val
65 70 75 80

Glu Phe Leu Asn Arg Trp Ile Thr Phe Ser Gln Ser Ile Ile Ser Thr
85 90 95

Leu Thr Gly Ser Gly Pro Ala Ser Ser Ser Thr Lys Lys Thr Gln Leu
100 105 110

Gln Leu Glu His Leu Leu Leu Asp Leu Gln Met Ile Leu Asn Gly Ile
115 120 125

Asn Asn Tyr Lys Asn Pro Lys
130 135

<210> SEQ ID NO 4
<211> LENGTH: 135
<212> TYPE: PRT
<213> ORGANISM: Artificial Sequence
<220> FEATURE:
<223> OTHER INFORMATION: IL-2-3

<400> SEQUENCE: 4

Asn Pro Lys Leu Thr Arg Met Leu Thr Phe Lys Phe Tyr Met Pro Lys
1 5 10 15

Lys Ala Thr Glu Leu Lys His Leu Gln Cys Leu Glu Glu Glu Leu Lys
20 25 30

```
Pro Leu Glu Glu Val Leu Asn Leu Ala Gln Ser Lys Asn Phe His Leu
        35                  40                  45

Arg Pro Arg Asp Leu Ile Ser Asn Ile Asn Val Ile Val Leu Glu Leu
    50                  55                  60

Lys Gly Ser Glu Thr Thr Phe Met Cys Glu Tyr Ala Asp Glu Thr Ala
65                  70                  75                  80

Thr Ile Val Glu Phe Leu Asn Arg Trp Ile Thr Phe Ser Gln Ser Ile
                85                  90                  95

Ile Ser Thr Leu Thr Gly Ser Gly Pro Ala Ser Ser Ser Thr Lys Lys
            100                 105                 110

Thr Gln Leu Gln Leu Glu His Leu Leu Leu Asp Leu Gln Met Ile Leu
        115                 120                 125

Asn Gly Ile Asn Asn Tyr Lys
    130                 135


<210> SEQ ID NO 5
<211> LENGTH: 162
<212> TYPE: PRT
<213> ORGANISM: Homo sapiens

<400> SEQUENCE: 5

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser


<210> SEQ ID NO 6
<211> LENGTH: 118
<212> TYPE: PRT
<213> ORGANISM: Artificial Sequence
<220> FEATURE:
<223> OTHER INFORMATION: IL-15-1

<400> SEQUENCE: 6

Ala Ser Ile His Asp Thr Val Glu Asn Leu Ile Ile Leu Ala Asn Asn
1               5                   10                  15

Ser Leu Ser Ser Asn Gly Asn Val Thr Glu Ser Gly Cys Lys Glu Cys
            20                  25                  30
```

Glu Glu Leu Glu Glu Lys Asn Ile Lys Glu Phe Leu Gln Ser Phe Val
35 40 45

His Ile Val Gln Met Phe Ile Asn Thr Ser Gly Gly Gly Gly Asn Trp
50 55 60

Val Asn Val Ile Ser Asp Leu Lys Lys Ile Glu Asp Leu Ile Gln Ser
65 70 75 80

Met His Ile Asp Ala Thr Leu Tyr Thr Glu Ser Asp Val His Pro Ser
85 90 95

Cys Lys Val Thr Ala Met Lys Cys Phe Leu Leu Glu Leu Gln Val Ile
100 105 110

Ser Leu Glu Ser Gly Asp
115

<210> SEQ ID NO 7
<211> LENGTH: 720
<212> TYPE: PRT
<213> ORGANISM: Artificial Sequence
<220> FEATURE:
<223> OTHER INFORMATION: C361-IL2-1

<400> SEQUENCE: 7

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

Arg Ala Asp Leu Ala Lys Tyr Ile Cys Glu Asn Gln Asp Ser Ile Ser
260 265 270

-continued

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Glu Ala Ala Ala Lys Ala Glu
        355                 360                 365

Ala Ala Ala Arg Asp Leu Ile Ser Asn Ile Asn Val Ile Val Leu Glu
    370                 375                 380

Leu Lys Gly Ser Glu Thr Thr Phe Met Cys Glu Tyr Ala Asp Glu Thr
385                 390                 395                 400

Ala Thr Ile Val Glu Phe Leu Asn Arg Trp Ile Thr Phe Ser Gln Ser
                405                 410                 415

Ile Ile Ser Thr Leu Thr Gly Ser Gly Pro Ala Ser Ser Ser Thr Lys
            420                 425                 430

Lys Thr Gln Leu Gln Leu Glu His Leu Leu Leu Asp Leu Gln Met Ile
        435                 440                 445

Leu Asn Gly Ile Asn Asn Tyr Lys Asn Pro Lys Leu Thr Arg Met Leu
    450                 455                 460

Thr Phe Lys Phe Tyr Met Pro Lys Lys Ala Thr Glu Leu Lys His Leu
465                 470                 475                 480

Gln Cys Leu Glu Glu Glu Leu Lys Pro Leu Glu Glu Val Leu Asn Leu
                485                 490                 495

Ala Gly Ser Asp Pro His Glu Cys Tyr Ala Lys Val Phe Asp Glu Phe
            500                 505                 510

Lys Pro Leu Val Glu Glu Pro Gln Asn Leu Ile Lys Gln Asn Cys Glu
        515                 520                 525

Leu Phe Glu Gln Leu Gly Glu Tyr Lys Phe Gln Asn Ala Leu Leu Val
    530                 535                 540

Arg Tyr Thr Lys Lys Val Pro Gln Val Ser Thr Pro Thr Leu Val Glu
545                 550                 555                 560

Val Ser Arg Asn Leu Gly Lys Val Gly Ser Lys Cys Cys Lys His Pro
                565                 570                 575

Glu Ala Lys Arg Met Pro Cys Ala Glu Asp Tyr Leu Ser Val Val Leu
            580                 585                 590

Asn Gln Leu Cys Val Leu His Glu Lys Thr Pro Val Ser Asp Arg Val
        595                 600                 605

Thr Lys Cys Cys Thr Glu Ser Leu Val Asn Arg Arg Pro Cys Phe Ser
    610                 615                 620

Ala Leu Glu Val Asp Glu Thr Tyr Val Pro Lys Glu Phe Asn Ala Glu
625                 630                 635                 640

Thr Phe Thr Phe His Ala Asp Ile Cys Thr Leu Ser Glu Lys Glu Arg
                645                 650                 655

Gln Ile Lys Lys Gln Thr Ala Leu Val Glu Leu Val Lys His Lys Pro
            660                 665                 670

Lys Ala Thr Lys Glu Gln Leu Lys Ala Val Met Asp Asp Phe Ala Ala
        675                 680                 685
```

```
Phe Val Glu Lys Cys Cys Lys Ala Asp Asp Lys Glu Thr Cys Phe Ala
    690                 695                 700

Glu Glu Gly Lys Lys Leu Val Ala Ala Ser Gln Ala Ala Leu Gly Leu
705                 710                 715                 720


<210> SEQ ID NO 8
<211> LENGTH: 726
<212> TYPE: PRT
<213> ORGANISM: Artificial Sequence
<220> FEATURE:
<223> OTHER INFORMATION: D56-IL2-2

<400> SEQUENCE: 8

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Ala Ala Ala Ala Ala Lys Leu Thr
    50                  55                  60

Arg Met Leu Thr Phe Lys Phe Tyr Met Pro Lys Lys Ala Thr Glu Leu
65                  70                  75                  80

Lys His Leu Gln Cys Leu Glu Glu Glu Leu Lys Pro Leu Glu Glu Val
                85                  90                  95

Leu Asn Leu Ala Gln Ser Lys Asn Phe His Leu Arg Pro Arg Asp Leu
            100                 105                 110

Ile Ser Asn Ile Asn Val Ile Val Leu Glu Leu Lys Gly Ser Glu Thr
        115                 120                 125

Thr Phe Met Cys Glu Tyr Ala Asp Glu Thr Ala Thr Ile Val Glu Phe
    130                 135                 140

Leu Asn Arg Trp Ile Thr Phe Ser Gln Ser Ile Ile Ser Thr Leu Thr
145                 150                 155                 160

Gly Ser Gly Pro Ala Ser Ser Ser Thr Lys Lys Thr Gln Leu Gln Leu
                165                 170                 175

Glu His Leu Leu Leu Asp Leu Gln Met Ile Leu Asn Gly Ile Asn Asn
            180                 185                 190

Tyr Lys Asn Pro Lys Glu Ser Ala Glu Asn Cys Asp Lys Ser Leu His
        195                 200                 205

Thr Leu Phe Gly Asp Lys Leu Cys Thr Val Ala Thr Leu Arg Glu Thr
    210                 215                 220

Tyr Gly Glu Met Ala Asp Cys Cys Ala Lys Gln Glu Pro Glu Arg Asn
225                 230                 235                 240

Glu Cys Phe Leu Gln His Lys Asp Asp Asn Pro Asn Leu Pro Arg Leu
                245                 250                 255

Val Arg Pro Glu Val Asp Val Met Cys Thr Ala Phe His Asp Asn Glu
            260                 265                 270

Glu Thr Phe Leu Lys Lys Tyr Leu Tyr Glu Ile Ala Arg Arg His Pro
        275                 280                 285

Tyr Phe Tyr Ala Pro Glu Leu Leu Phe Phe Ala Lys Arg Tyr Lys Ala
    290                 295                 300

Ala Phe Thr Glu Cys Cys Gln Ala Ala Asp Lys Ala Ala Cys Leu Leu
305                 310                 315                 320

Pro Lys Leu Asp Glu Leu Arg Asp Glu Gly Lys Ala Ser Ser Ala Lys
                325                 330                 335
```

```
Gln Arg Leu Lys Cys Ala Ser Leu Gln Lys Phe Gly Glu Arg Ala Phe
            340                 345                 350

Lys Ala Trp Ala Val Ala Arg Leu Ser Gln Arg Phe Pro Lys Ala Glu
        355                 360                 365

Phe Ala Glu Val Ser Lys Leu Val Thr Asp Leu Thr Lys Val His Thr
    370                 375                 380

Glu Cys Cys His Gly Asp Leu Leu Glu Cys Ala Asp Asp Arg Ala Asp
385                 390                 395                 400

Leu Ala Lys Tyr Ile Cys Glu Asn Gln Asp Ser Ile Ser Ser Lys Leu
                405                 410                 415

Lys Glu Cys Cys Glu Lys Pro Leu Leu Glu Lys Ser His Cys Ile Ala
            420                 425                 430

Glu Val Glu Asn Asp Glu Met Pro Ala Asp Leu Pro Ser Leu Ala Ala
        435                 440                 445

Asp Phe Val Glu Ser Lys Asp Val Cys Lys Asn Tyr Ala Glu Ala Lys
    450                 455                 460

Asp Val Phe Leu Gly Met Phe Leu Tyr Glu Tyr Ala Arg Arg His Pro
465                 470                 475                 480

Asp Tyr Ser Val Val Leu Leu Leu Arg Leu Ala Lys Thr Tyr Glu Thr
                485                 490                 495

Thr Leu Glu Lys Cys Cys Ala Ala Ala Asp Pro His Glu Cys Tyr Ala
            500                 505                 510

Lys Val Phe Asp Glu Phe Lys Pro Leu Val Glu Glu Pro Gln Asn Leu
        515                 520                 525

Ile Lys Gln Asn Cys Glu Leu Phe Glu Gln Leu Gly Glu Tyr Lys Phe
    530                 535                 540

Gln Asn Ala Leu Leu Val Arg Tyr Thr Lys Lys Val Pro Gln Val Ser
545                 550                 555                 560

Thr Pro Thr Leu Val Glu Val Ser Arg Asn Leu Gly Lys Val Gly Ser
                565                 570                 575

Lys Cys Cys Lys His Pro Glu Ala Lys Arg Met Pro Cys Ala Glu Asp
            580                 585                 590

Tyr Leu Ser Val Val Leu Asn Gln Leu Cys Val Leu His Glu Lys Thr
        595                 600                 605

Pro Val Ser Asp Arg Val Thr Lys Cys Cys Thr Glu Ser Leu Val Asn
    610                 615                 620

Arg Arg Pro Cys Phe Ser Ala Leu Glu Val Asp Glu Thr Tyr Val Pro
625                 630                 635                 640

Lys Glu Phe Asn Ala Glu Thr Phe Thr Phe His Ala Asp Ile Cys Thr
                645                 650                 655

Leu Ser Glu Lys Glu Arg Gln Ile Lys Lys Gln Thr Ala Leu Val Glu
            660                 665                 670

Leu Val Lys His Lys Pro Lys Ala Thr Lys Glu Gln Leu Lys Ala Val
        675                 680                 685

Met Asp Asp Phe Ala Ala Phe Val Glu Lys Cys Cys Lys Ala Asp Asp
    690                 695                 700

Lys Glu Thr Cys Phe Ala Glu Glu Gly Lys Lys Leu Val Ala Ala Ser
705                 710                 715                 720

Gln Ala Ala Leu Gly Leu
                725
```

<210> SEQ ID NO 9
<211> LENGTH: 721
<212> TYPE: PRT

<213> ORGANISM: Artificial Sequence
<220> FEATURE:
<223> OTHER INFORMATION: A300-IL-2-3

<400> SEQUENCE: 9

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

Arg Ala Asp Leu Ala Lys Tyr Ile Cys Glu Asn Gln Asp Ser Ile Ser
260 265 270

Ser Lys Leu Lys Glu Cys Cys Glu Lys Pro Leu Leu Glu Lys Ser His
275 280 285

Cys Ile Ala Glu Val Glu Asn Asp Glu Met Pro Ala Asn Pro Lys Leu
290 295 300

Thr Arg Met Leu Thr Phe Lys Phe Tyr Met Pro Lys Lys Ala Thr Glu
305 310 315 320

Leu Lys His Leu Gln Cys Leu Glu Glu Glu Leu Lys Pro Leu Glu Glu
325 330 335

Val Leu Asn Leu Ala Gln Ser Lys Asn Phe His Leu Arg Pro Arg Asp
340 345 350

Leu Ile Ser Asn Ile Asn Val Ile Val Leu Glu Leu Lys Gly Ser Glu
355 360 365

Thr Thr Phe Met Cys Glu Tyr Ala Asp Glu Thr Ala Thr Ile Val Glu
370 375 380

```
Phe Leu Asn Arg Trp Ile Thr Phe Ser Gln Ser Ile Ile Ser Thr Leu
385                 390                 395                 400

Thr Gly Ser Gly Pro Ala Ser Ser Ser Thr Lys Lys Thr Gln Leu Gln
                405                 410                 415

Leu Glu His Leu Leu Leu Asp Leu Gln Met Ile Leu Asn Gly Ile Asn
            420                 425                 430

Asn Tyr Lys Gly Asp Leu Pro Ser Leu Ala Ala Asp Phe Val Glu Ser
        435                 440                 445

Lys Asp Val Cys Lys Asn Tyr Ala Glu Ala Lys Asp Val Phe Leu Gly
    450                 455                 460

Met Phe Leu Tyr Glu Tyr Ala Arg Arg His Pro Asp Tyr Ser Val Val
465                 470                 475                 480

Leu Leu Leu Arg Leu Ala Lys Thr Tyr Glu Thr Thr Leu Glu Lys Cys
                485                 490                 495

Cys Ala Ala Ala Asp Pro His Glu Cys Tyr Ala Lys Val Phe Asp Glu
            500                 505                 510

Phe Lys Pro Leu Val Glu Glu Pro Gln Asn Leu Ile Lys Gln Asn Cys
        515                 520                 525

Glu Leu Phe Glu Gln Leu Gly Glu Tyr Lys Phe Gln Asn Ala Leu Leu
    530                 535                 540

Val Arg Tyr Thr Lys Lys Val Pro Gln Val Ser Thr Pro Thr Leu Val
545                 550                 555                 560

Glu Val Ser Arg Asn Leu Gly Lys Val Gly Ser Lys Cys Cys Lys His
                565                 570                 575

Pro Glu Ala Lys Arg Met Pro Cys Ala Glu Asp Tyr Leu Ser Val Val
            580                 585                 590

Leu Asn Gln Leu Cys Val Leu His Glu Lys Thr Pro Val Ser Asp Arg
        595                 600                 605

Val Thr Lys Cys Cys Thr Glu Ser Leu Val Asn Arg Arg Pro Cys Phe
    610                 615                 620

Ser Ala Leu Glu Val Asp Glu Thr Tyr Val Pro Lys Glu Phe Asn Ala
625                 630                 635                 640

Glu Thr Phe Thr Phe His Ala Asp Ile Cys Thr Leu Ser Glu Lys Glu
                645                 650                 655

Arg Gln Ile Lys Lys Gln Thr Ala Leu Val Glu Leu Val Lys His Lys
            660                 665                 670

Pro Lys Ala Thr Lys Glu Gln Leu Lys Ala Val Met Asp Asp Phe Ala
        675                 680                 685

Ala Phe Val Glu Lys Cys Cys Lys Ala Asp Asp Lys Glu Thr Cys Phe
    690                 695                 700

Ala Glu Glu Gly Lys Lys Leu Val Ala Ala Ser Gln Ala Ala Leu Gly
705                 710                 715                 720

Leu
```

<210> SEQ ID NO 10
<211> LENGTH: 720
<212> TYPE: PRT
<213> ORGANISM: Artificial Sequence
<220> FEATURE:
<223> OTHER INFORMATION: A362-IL2-3

<400> SEQUENCE: 10

```
Asp Ala His Lys Ser Glu Val Ala His Arg Phe Lys Asp Leu Gly Glu
1               5                   10                  15
```

-continued

```
Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Asn Pro Lys Leu Thr Arg
        355                 360                 365

Met Leu Thr Phe Lys Phe Tyr Met Pro Lys Lys Ala Thr Glu Leu Lys
    370                 375                 380

His Leu Gln Cys Leu Glu Glu Glu Leu Lys Pro Leu Glu Glu Val Leu
385                 390                 395                 400

Asn Leu Ala Gln Ser Lys Asn Phe His Leu Arg Pro Arg Asp Leu Ile
                405                 410                 415

Ser Asn Ile Asn Val Ile Val Leu Glu Leu Lys Gly Ser Glu Thr Thr
            420                 425                 430
```

```
Phe Met Cys Glu Tyr Ala Asp Glu Thr Ala Thr Ile Val Glu Phe Leu
        435                 440                 445

Asn Arg Trp Ile Thr Phe Ser Gln Ser Ile Ile Ser Thr Leu Thr Gly
    450                 455                 460

Ser Gly Pro Ala Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Ala Ala Asp Pro His Glu Cys Tyr Ala Lys Val Phe Asp Glu Phe
            500                 505                 510

Lys Pro Leu Val Glu Glu Pro Gln Asn Leu Ile Lys Gln Asn Cys Glu
        515                 520                 525

Leu Phe Glu Gln Leu Gly Glu Tyr Lys Phe Gln Asn Ala Leu Leu Val
    530                 535                 540

Arg Tyr Thr Lys Lys Val Pro Gln Val Ser Thr Pro Thr Leu Val Glu
545                 550                 555                 560

Val Ser Arg Asn Leu Gly Lys Val Gly Ser Lys Cys Cys Lys His Pro
                565                 570                 575

Glu Ala Lys Arg Met Pro Cys Ala Glu Asp Tyr Leu Ser Val Val Leu
            580                 585                 590

Asn Gln Leu Cys Val Leu His Glu Lys Thr Pro Val Ser Asp Arg Val
        595                 600                 605

Thr Lys Cys Cys Thr Glu Ser Leu Val Asn Arg Arg Pro Cys Phe Ser
    610                 615                 620

Ala Leu Glu Val Asp Glu Thr Tyr Val Pro Lys Glu Phe Asn Ala Glu
625                 630                 635                 640

Thr Phe Thr Phe His Ala Asp Ile Cys Thr Leu Ser Glu Lys Glu Arg
                645                 650                 655

Gln Ile Lys Lys Gln Thr Ala Leu Val Glu Leu Val Lys His Lys Pro
            660                 665                 670

Lys Ala Thr Lys Glu Gln Leu Lys Ala Val Met Asp Asp Phe Ala Ala
        675                 680                 685

Phe Val Glu Lys Cys Cys Lys Ala Asp Asp Lys Glu Thr Cys Phe Ala
    690                 695                 700

Glu Glu Gly Lys Lys Leu Val Ala Ala Ser Gln Ala Ala Leu Gly Leu
705                 710                 715                 720


<210> SEQ ID NO 11
<211> LENGTH: 726
<212> TYPE: PRT
<213> ORGANISM: Artificial Sequence
<220> FEATURE:
<223> OTHER INFORMATION: C361-IL-2-1-His

<400> SEQUENCE: 11

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Glu Ala Ala Ala Lys Ala Glu
        355                 360                 365

Ala Ala Ala Arg Asp Leu Ile Ser Asn Ile Asn Val Ile Val Leu Glu
    370                 375                 380

Leu Lys Gly Ser Glu Thr Thr Phe Met Cys Glu Tyr Ala Asp Glu Thr
385                 390                 395                 400

Ala Thr Ile Val Glu Phe Leu Asn Arg Trp Ile Thr Phe Ser Gln Ser
                405                 410                 415

Ile Ile Ser Thr Leu Thr Gly Ser Gly Pro Ala Ser Ser Ser Thr Lys
            420                 425                 430

Lys Thr Gln Leu Gln Leu Glu His Leu Leu Leu Asp Leu Gln Met Ile
        435                 440                 445

Leu Asn Gly Ile Asn Asn Tyr Lys Asn Pro Lys Leu Thr Arg Met Leu
    450                 455                 460

Thr Phe Lys Phe Tyr Met Pro Lys Lys Ala Thr Glu Leu Lys His Leu
465                 470                 475                 480

Gln Cys Leu Glu Glu Glu Leu Lys Pro Leu Glu Glu Val Leu Asn Leu
                485                 490                 495
```

```
Ala Gly Ser Asp Pro His Glu Cys Tyr Ala Lys Val Phe Asp Glu Phe
            500                 505                 510

Lys Pro Leu Val Glu Glu Pro Gln Asn Leu Ile Lys Gln Asn Cys Glu
        515                 520                 525

Leu Phe Glu Gln Leu Gly Glu Tyr Lys Phe Gln Asn Ala Leu Leu Val
    530                 535                 540

Arg Tyr Thr Lys Lys Val Pro Gln Val Ser Thr Pro Thr Leu Val Glu
545                 550                 555                 560

Val Ser Arg Asn Leu Gly Lys Val Gly Ser Lys Cys Cys Lys His Pro
                565                 570                 575

Glu Ala Lys Arg Met Pro Cys Ala Glu Asp Tyr Leu Ser Val Val Leu
            580                 585                 590

Asn Gln Leu Cys Val Leu His Glu Lys Thr Pro Val Ser Asp Arg Val
        595                 600                 605

Thr Lys Cys Cys Thr Glu Ser Leu Val Asn Arg Arg Pro Cys Phe Ser
    610                 615                 620

Ala Leu Glu Val Asp Glu Thr Tyr Val Pro Lys Glu Phe Asn Ala Glu
625                 630                 635                 640

Thr Phe Thr Phe His Ala Asp Ile Cys Thr Leu Ser Glu Lys Glu Arg
                645                 650                 655

Gln Ile Lys Lys Gln Thr Ala Leu Val Glu Leu Val Lys His Lys Pro
            660                 665                 670

Lys Ala Thr Lys Glu Gln Leu Lys Ala Val Met Asp Asp Phe Ala Ala
        675                 680                 685

Phe Val Glu Lys Cys Cys Lys Ala Asp Asp Lys Glu Thr Cys Phe Ala
    690                 695                 700

Glu Glu Gly Lys Lys Leu Val Ala Ala Ser Gln Ala Ala Leu Gly Leu
705                 710                 715                 720

His His His His His His
                725


<210> SEQ ID NO 12
<211> LENGTH: 732
<212> TYPE: PRT
<213> ORGANISM: Artificial Sequence
<220> FEATURE:
<223> OTHER INFORMATION: D56-IL-2-2-His

<400> SEQUENCE: 12

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Ala Ala Ala Ala Ala Lys Leu Thr
    50                  55                  60

Arg Met Leu Thr Phe Lys Phe Tyr Met Pro Lys Lys Ala Thr Glu Leu
65                  70                  75                  80

Lys His Leu Gln Cys Leu Glu Glu Glu Leu Lys Pro Leu Glu Glu Val
                85                  90                  95

Leu Asn Leu Ala Gln Ser Lys Asn Phe His Leu Arg Pro Arg Asp Leu
            100                 105                 110

Ile Ser Asn Ile Asn Val Ile Val Leu Glu Leu Lys Gly Ser Glu Thr
        115                 120                 125
```

```
Thr Phe Met Cys Glu Tyr Ala Asp Glu Thr Ala Thr Ile Val Glu Phe
    130                 135                 140

Leu Asn Arg Trp Ile Thr Phe Ser Gln Ser Ile Ile Ser Thr Leu Thr
145                 150                 155                 160

Gly Ser Gly Pro Ala Ser Ser Ser Thr Lys Lys Thr Gln Leu Gln Leu
                165                 170                 175

Glu His Leu Leu Leu Asp Leu Gln Met Ile Leu Asn Gly Ile Asn Asn
            180                 185                 190

Tyr Lys Asn Pro Lys Glu Ser Ala Glu Asn Cys Asp Lys Ser Leu His
        195                 200                 205

Thr Leu Phe Gly Asp Lys Leu Cys Thr Val Ala Thr Leu Arg Glu Thr
    210                 215                 220

Tyr Gly Glu Met Ala Asp Cys Cys Ala Lys Gln Glu Pro Glu Arg Asn
225                 230                 235                 240

Glu Cys Phe Leu Gln His Lys Asp Asp Asn Pro Asn Leu Pro Arg Leu
                245                 250                 255

Val Arg Pro Glu Val Asp Val Met Cys Thr Ala Phe His Asp Asn Glu
            260                 265                 270

Glu Thr Phe Leu Lys Lys Tyr Leu Tyr Glu Ile Ala Arg Arg His Pro
        275                 280                 285

Tyr Phe Tyr Ala Pro Glu Leu Leu Phe Phe Ala Lys Arg Tyr Lys Ala
    290                 295                 300

Ala Phe Thr Glu Cys Cys Gln Ala Ala Asp Lys Ala Ala Cys Leu Leu
305                 310                 315                 320

Pro Lys Leu Asp Glu Leu Arg Asp Glu Gly Lys Ala Ser Ser Ala Lys
                325                 330                 335

Gln Arg Leu Lys Cys Ala Ser Leu Gln Lys Phe Gly Glu Arg Ala Phe
            340                 345                 350

Lys Ala Trp Ala Val Ala Arg Leu Ser Gln Arg Phe Pro Lys Ala Glu
        355                 360                 365

Phe Ala Glu Val Ser Lys Leu Val Thr Asp Leu Thr Lys Val His Thr
    370                 375                 380

Glu Cys Cys His Gly Asp Leu Leu Glu Cys Ala Asp Asp Arg Ala Asp
385                 390                 395                 400

Leu Ala Lys Tyr Ile Cys Glu Asn Gln Asp Ser Ile Ser Ser Lys Leu
                405                 410                 415

Lys Glu Cys Cys Glu Lys Pro Leu Leu Glu Lys Ser His Cys Ile Ala
            420                 425                 430

Glu Val Glu Asn Asp Glu Met Pro Ala Asp Leu Pro Ser Leu Ala Ala
        435                 440                 445

Asp Phe Val Glu Ser Lys Asp Val Cys Lys Asn Tyr Ala Glu Ala Lys
    450                 455                 460

Asp Val Phe Leu Gly Met Phe Leu Tyr Glu Tyr Ala Arg Arg His Pro
465                 470                 475                 480

Asp Tyr Ser Val Val Leu Leu Leu Arg Leu Ala Lys Thr Tyr Glu Thr
                485                 490                 495

Thr Leu Glu Lys Cys Cys Ala Ala Ala Asp Pro His Glu Cys Tyr Ala
            500                 505                 510

Lys Val Phe Asp Glu Phe Lys Pro Leu Val Glu Glu Pro Gln Asn Leu
        515                 520                 525

Ile Lys Gln Asn Cys Glu Leu Phe Glu Gln Leu Gly Glu Tyr Lys Phe
    530                 535                 540
```

Gln Asn Ala Leu Leu Val Arg Tyr Thr Lys Lys Val Pro Gln Val Ser
545 550 555 560

Thr Pro Thr Leu Val Glu Val Ser Arg Asn Leu Gly Lys Val Gly Ser
565 570 575

Lys Cys Cys Lys His Pro Glu Ala Lys Arg Met Pro Cys Ala Glu Asp
580 585 590

Tyr Leu Ser Val Val Leu Asn Gln Leu Cys Val Leu His Glu Lys Thr
595 600 605

Pro Val Ser Asp Arg Val Thr Lys Cys Cys Thr Glu Ser Leu Val Asn
610 615 620

Arg Arg Pro Cys Phe Ser Ala Leu Glu Val Asp Glu Thr Tyr Val Pro
625 630 635 640

Lys Glu Phe Asn Ala Glu Thr Phe Thr Phe His Ala Asp Ile Cys Thr
645 650 655

Leu Ser Glu Lys Glu Arg Gln Ile Lys Lys Gln Thr Ala Leu Val Glu
660 665 670

Leu Val Lys His Lys Pro Lys Ala Thr Lys Glu Gln Leu Lys Ala Val
675 680 685

Met Asp Asp Phe Ala Ala Phe Val Glu Lys Cys Cys Lys Ala Asp Asp
690 695 700

Lys Glu Thr Cys Phe Ala Glu Glu Gly Lys Lys Leu Val Ala Ala Ser
705 710 715 720

Gln Ala Ala Leu Gly Leu His His His His His His
725 730

<210> SEQ ID NO 13
<211> LENGTH: 727
<212> TYPE: PRT
<213> ORGANISM: Artificial Sequence
<220> FEATURE:
<223> OTHER INFORMATION: A300-IL-2-3_His

<400> SEQUENCE: 13

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asn Pro Lys Leu
    290                 295                 300

Thr Arg Met Leu Thr Phe Lys Phe Tyr Met Pro Lys Lys Ala Thr Glu
305                 310                 315                 320

Leu Lys His Leu Gln Cys Leu Glu Glu Glu Leu Lys Pro Leu Glu Glu
                325                 330                 335

Val Leu Asn Leu Ala Gln Ser Lys Asn Phe His Leu Arg Pro Arg Asp
            340                 345                 350

Leu Ile Ser Asn Ile Asn Val Ile Val Leu Glu Leu Lys Gly Ser Glu
        355                 360                 365

Thr Thr Phe Met Cys Glu Tyr Ala Asp Glu Thr Ala Thr Ile Val Glu
    370                 375                 380

Phe Leu Asn Arg Trp Ile Thr Phe Ser Gln Ser Ile Ile Ser Thr Leu
385                 390                 395                 400

Thr Gly Ser Gly Pro Ala Ser Ser Ser Thr Lys Lys Thr Gln Leu Gln
                405                 410                 415

Leu Glu His Leu Leu Leu Asp Leu Gln Met Ile Leu Asn Gly Ile Asn
            420                 425                 430

Asn Tyr Lys Gly Asp Leu Pro Ser Leu Ala Ala Asp Phe Val Glu Ser
        435                 440                 445

Lys Asp Val Cys Lys Asn Tyr Ala Glu Ala Lys Asp Val Phe Leu Gly
    450                 455                 460

Met Phe Leu Tyr Glu Tyr Ala Arg Arg His Pro Asp Tyr Ser Val Val
465                 470                 475                 480

Leu Leu Leu Arg Leu Ala Lys Thr Tyr Glu Thr Thr Leu Glu Lys Cys
                485                 490                 495

Cys Ala Ala Ala Asp Pro His Glu Cys Tyr Ala Lys Val Phe Asp Glu
            500                 505                 510

Phe Lys Pro Leu Val Glu Glu Pro Gln Asn Leu Ile Lys Gln Asn Cys
        515                 520                 525

Glu Leu Phe Glu Gln Leu Gly Glu Tyr Lys Phe Gln Asn Ala Leu Leu
    530                 535                 540

Val Arg Tyr Thr Lys Lys Val Pro Gln Val Ser Thr Pro Thr Leu Val
545                 550                 555                 560

Glu Val Ser Arg Asn Leu Gly Lys Val Gly Ser Lys Cys Cys Lys His
                565                 570                 575

Pro Glu Ala Lys Arg Met Pro Cys Ala Glu Asp Tyr Leu Ser Val Val
            580                 585                 590
```

Leu Asn Gln Leu Cys Val Leu His Glu Lys Thr Pro Val Ser Asp Arg
595 600 605

Val Thr Lys Cys Cys Thr Glu Ser Leu Val Asn Arg Arg Pro Cys Phe
610 615 620

Ser Ala Leu Glu Val Asp Glu Thr Tyr Val Pro Lys Glu Phe Asn Ala
625 630 635 640

Glu Thr Phe Thr Phe His Ala Asp Ile Cys Thr Leu Ser Glu Lys Glu
645 650 655

Arg Gln Ile Lys Lys Gln Thr Ala Leu Val Glu Leu Val Lys His Lys
660 665 670

Pro Lys Ala Thr Lys Glu Gln Leu Lys Ala Val Met Asp Asp Phe Ala
675 680 685

Ala Phe Val Glu Lys Cys Cys Lys Ala Asp Asp Lys Glu Thr Cys Phe
690 695 700

Ala Glu Glu Gly Lys Lys Leu Val Ala Ala Ser Gln Ala Ala Leu Gly
705 710 715 720

Leu His His His His His His
725

<210> SEQ ID NO 14
<211> LENGTH: 726
<212> TYPE: PRT
<213> ORGANISM: Artificial Sequence
<220> FEATURE:
<223> OTHER INFORMATION: A362-IL-2-3_His

<400> SEQUENCE: 14

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

-continued

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Asn Pro Lys Leu Thr Arg
        355                 360                 365

Met Leu Thr Phe Lys Phe Tyr Met Pro Lys Lys Ala Thr Glu Leu Lys
    370                 375                 380

His Leu Gln Cys Leu Glu Glu Glu Leu Lys Pro Leu Glu Glu Val Leu
385                 390                 395                 400

Asn Leu Ala Gln Ser Lys Asn Phe His Leu Arg Pro Arg Asp Leu Ile
                405                 410                 415

Ser Asn Ile Asn Val Ile Val Leu Glu Leu Lys Gly Ser Glu Thr Thr
            420                 425                 430

Phe Met Cys Glu Tyr Ala Asp Glu Thr Ala Thr Ile Val Glu Phe Leu
        435                 440                 445

Asn Arg Trp Ile Thr Phe Ser Gln Ser Ile Ile Ser Thr Leu Thr Gly
    450                 455                 460

Ser Gly Pro Ala Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Ala Ala Asp Pro His Glu Cys Tyr Ala Lys Val Phe Asp Glu Phe
            500                 505                 510

Lys Pro Leu Val Glu Glu Pro Gln Asn Leu Ile Lys Gln Asn Cys Glu
        515                 520                 525

Leu Phe Glu Gln Leu Gly Glu Tyr Lys Phe Gln Asn Ala Leu Leu Val
    530                 535                 540

Arg Tyr Thr Lys Lys Val Pro Gln Val Ser Thr Pro Thr Leu Val Glu
545                 550                 555                 560

Val Ser Arg Asn Leu Gly Lys Val Gly Ser Lys Cys Cys Lys His Pro
                565                 570                 575

Glu Ala Lys Arg Met Pro Cys Ala Glu Asp Tyr Leu Ser Val Val Leu
            580                 585                 590

Asn Gln Leu Cys Val Leu His Glu Lys Thr Pro Val Ser Asp Arg Val
        595                 600                 605

Thr Lys Cys Cys Thr Glu Ser Leu Val Asn Arg Arg Pro Cys Phe Ser
    610                 615                 620

Ala Leu Glu Val Asp Glu Thr Tyr Val Pro Lys Glu Phe Asn Ala Glu
625                 630                 635                 640
```

```
Thr Phe Thr Phe His Ala Asp Ile Cys Thr Leu Ser Glu Lys Glu Arg
                645                 650                 655

Gln Ile Lys Lys Gln Thr Ala Leu Val Glu Leu Val Lys His Lys Pro
            660                 665                 670

Lys Ala Thr Lys Glu Gln Leu Lys Ala Val Met Asp Asp Phe Ala Ala
        675                 680                 685

Phe Val Glu Lys Cys Cys Lys Ala Asp Asp Lys Glu Thr Cys Phe Ala
    690                 695                 700

Glu Glu Gly Lys Lys Leu Val Ala Ala Ser Gln Ala Ala Leu Gly Leu
705                 710                 715                 720

His His His His His His
                725


<210> SEQ ID NO 15
<211> LENGTH: 609
<212> TYPE: PRT
<213> ORGANISM: Homo sapiens

<400> SEQUENCE: 15

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270
```

```
Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu


<210> SEQ ID NO 16
<211> LENGTH: 4
<212> TYPE: PRT
<213> ORGANISM: Artificial Sequence
<220> FEATURE:
<223> OTHER INFORMATION: linker

<400> SEQUENCE: 16

Gly Gly Gly Gly
1
```

<210> SEQ ID NO 17
<211> LENGTH: 20
<212> TYPE: PRT
<213> ORGANISM: Artificial Sequence
<220> FEATURE:
<223> OTHER INFORMATION: signal peptide

<400> SEQUENCE: 17

Met Glu Thr Asp Thr Leu Leu Leu Trp Val Leu Leu Leu Trp Val Pro
1 5 10 15

Gly Ser Thr Gly
20

<210> SEQ ID NO 18
<211> LENGTH: 10
<212> TYPE: PRT
<213> ORGANISM: Artificial Sequence
<220> FEATURE:
<223> OTHER INFORMATION: linker

<400> SEQUENCE: 18

Glu Ala Ala Ala Lys Ala Glu Ala Ala Ala
1 5 10

<210> SEQ ID NO 19
<211> LENGTH: 6
<212> TYPE: PRT
<213> ORGANISM: Artificial Sequence
<220> FEATURE:
<223> OTHER INFORMATION: linker

<400> SEQUENCE: 19

Ala Ala Ala Ala Ala Lys
1 5

<210> SEQ ID NO 20
<211> LENGTH: 130
<212> TYPE: PRT
<213> ORGANISM: Artificial Sequence
<220> FEATURE:
<223> OTHER INFORMATION: IL-2*

<400> SEQUENCE: 20

Leu Thr Arg Met Leu Thr Phe Lys Phe Tyr Met Pro Lys Lys Ala Thr
1 5 10 15

Glu Leu Lys His Leu Gln Cys Leu Glu Glu Glu Leu Lys Pro Leu Glu
20 25 30

Glu Val Leu Asn Leu Ala Gln Ser Lys Asn Phe His Leu Arg Pro Arg
35 40 45

Asp Leu Ile Ser Asn Ile Asn Val Ile Val Leu Glu Leu Lys Gly Ser
50 55 60

Glu Thr Thr Phe Met Cys Glu Tyr Ala Asp Glu Thr Ala Thr Ile Val
65 70 75 80

Glu Phe Leu Asn Arg Trp Ile Thr Phe Ser Gln Ser Ile Ile Ser Thr
85 90 95

Leu Thr Gly Ser Gly Pro Ala Ser Ser Ser Thr Lys Lys Thr Gln Leu
100 105 110

Gln Leu Glu His Leu Leu Leu Asp Leu Gln Met Ile Leu Asn Gly Ile
115 120 125

Asn Asn
130

<210> SEQ ID NO 21
<211> LENGTH: 135
<212> TYPE: PRT
<213> ORGANISM: Artificial Sequence
<220> FEATURE:
<223> OTHER INFORMATION: circular permulated IL-2

<400> SEQUENCE: 21

```
Asn Phe His Leu Arg Pro Arg Asp Leu Ile Ser Asn Ile Asn Val Ile
1               5                   10                  15

Val Leu Glu Leu Lys Gly Ser Glu Thr Thr Phe Met Cys Glu Tyr Ala
            20                  25                  30

Asp Glu Thr Ala Thr Ile Val Glu Phe Leu Asn Arg Trp Ile Thr Phe
        35                  40                  45

Ser Gln Ser Ile Ile Ser Thr Leu Thr Gly Ser Gly Pro Ala Ser Ser
    50                  55                  60

Ser Thr Lys Lys Thr Gln Leu Gln Leu Glu His Leu Leu Leu Asp Leu
65                  70                  75                  80

Gln Met Ile Leu Asn Gly Ile Asn Asn Tyr Lys Asn Pro Lys Leu Thr
                85                  90                  95

Arg Met Leu Thr Phe Lys Phe Tyr Met Pro Lys Lys Ala Thr Glu Leu
            100                 105                 110

Lys His Leu Gln Cys Leu Glu Glu Glu Leu Lys Pro Leu Glu Glu Val
        115                 120                 125

Leu Asn Leu Ala Gln Ser Lys
    130                 135
```

<210> SEQ ID NO 22
<211> LENGTH: 115
<212> TYPE: PRT
<213> ORGANISM: Artificial Sequence
<220> FEATURE:
<223> OTHER INFORMATION: circular permulated IL-15

<400> SEQUENCE: 22

```
Ser Ile His Asp Thr Val Glu Asn Leu Ile Ile Leu Ala Asn Asn Ser
1               5                   10                  15

Leu Ser Ser Asn Gly Asn Val Thr Glu Ser Gly Cys Lys Glu Cys Glu
            20                  25                  30

Glu Leu Glu Glu Lys Asn Ile Lys Glu Phe Leu Gln Ser Phe Val His
        35                  40                  45

Ile Val Gln Met Phe Ile Asn Thr Ser Gly Gly Gly Gly Asn Trp Val
    50                  55                  60

Asn Val Ile Ser Asp Leu Lys Lys Ile Glu Asp Leu Ile Gln Ser Met
65                  70                  75                  80

His Ile Asp Ala Thr Leu Tyr Thr Glu Ser Asp Val His Pro Ser Cys
                85                  90                  95

Lys Val Thr Ala Met Lys Cys Phe Leu Leu Glu Leu Gln Val Ile Ser
            100                 105                 110

Leu Glu Ser
        115
```

<210> SEQ ID NO 23
<211> LENGTH: 223
<212> TYPE: PRT
<213> ORGANISM: Artificial Sequence
<220> FEATURE:
<223> OTHER INFORMATION: Fc knob

<400> SEQUENCE: 23

```
His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Glu Glu Met Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220
```

<210> SEQ ID NO 24
<211> LENGTH: 223
<212> TYPE: PRT
<213> ORGANISM: Artificial Sequence
<220> FEATURE:
<223> OTHER INFORMATION: Fc hole

<400> SEQUENCE: 24

```
His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Cys Thr Leu
        115                 120                 125
```

```
Pro Pro Ser Arg Glu Glu Met Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220


<210> SEQ ID NO 25
<211> LENGTH: 368
<212> TYPE: PRT
<213> ORGANISM: Artificial Sequence
<220> FEATURE:
<223> OTHER INFORMATION: IL-2-knob

<400> SEQUENCE: 25

His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Glu Glu Met Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Gly Gly Gly Gly Ser Asn Phe His Leu Arg Pro Arg
225                 230                 235                 240

Asp Leu Ile Ser Asn Ile Asn Val Ile Val Leu Glu Leu Lys Gly Ser
                245                 250                 255

Glu Thr Thr Phe Met Cys Glu Tyr Ala Asp Glu Thr Ala Thr Ile Val
            260                 265                 270
```

```
Glu Phe Leu Asn Arg Trp Ile Thr Phe Ser Gln Ser Ile Ile Ser Thr
        275                 280                 285

Leu Thr Gly Ser Gly Pro Ala Ser Ser Ser Thr Lys Lys Thr Gln Leu
    290                 295                 300

Gln Leu Glu His Leu Leu Leu Asp Leu Gln Met Ile Leu Asn Gly Ile
305                 310                 315                 320

Asn Asn Tyr Lys Asn Pro Lys Leu Thr Arg Met Leu Thr Phe Lys Phe
                325                 330                 335

Tyr Met Pro Lys Lys Ala Thr Glu Leu Lys His Leu Gln Cys Leu Glu
            340                 345                 350

Glu Glu Leu Lys Pro Leu Glu Glu Val Leu Asn Leu Ala Gln Ser Lys
        355                 360                 365


<210> SEQ ID NO 26
<211> LENGTH: 398
<212> TYPE: PRT
<213> ORGANISM: Artificial Sequence
<220> FEATURE:
<223> OTHER INFORMATION: CD25-hole

<400> SEQUENCE: 26

His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Glu Glu Met Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Gly Gly Gly Gly Ser Glu Leu Cys Asp Asp Asp Pro
225                 230                 235                 240

Pro Glu Ile Pro His Ala Thr Phe Lys Ala Met Ala Tyr Lys Glu Gly
                245                 250                 255

Thr Met Leu Asn Cys Glu Cys Lys Arg Gly Phe Arg Arg Ile Lys Ser
            260                 265                 270
```

Gly Ser Leu Tyr Met Leu Cys Thr Gly Asn Ser Ser His Ser Ser Trp
275 280 285

Asp Asn Gln Cys Gln Cys Thr Ser Ser Ala Thr Arg Asn Thr Thr Lys
290 295 300

Gln Val Thr Pro Gln Pro Glu Glu Gln Lys Glu Arg Lys Thr Thr Glu
305 310 315 320

Met Gln Ser Pro Met Gln Pro Val Asp Gln Ala Ser Leu Pro Gly His
325 330 335

Cys Arg Glu Pro Pro Pro Trp Glu Asn Glu Ala Thr Glu Arg Ile Tyr
340 345 350

His Phe Val Val Gly Gln Met Val Tyr Tyr Gln Cys Val Gln Gly Tyr
355 360 365

Arg Ala Leu His Arg Gly Pro Ala Glu Ser Val Cys Lys Met Thr His
370 375 380

Gly Lys Thr Arg Trp Thr Gln Pro Gln Leu Ile Cys Thr Gly
385 390 395

<210> SEQ ID NO 27
<211> LENGTH: 368
<212> TYPE: PRT
<213> ORGANISM: Artificial Sequence
<220> FEATURE:
<223> OTHER INFORMATION: IL-2-hole

<400> SEQUENCE: 27

His Thr Cys Pro Pro Cys Pro Ala Pro Glu Ala Ala Gly Gly Pro Ser
1 5 10 15

Val Phe Leu Phe Pro Pro Lys Pro Lys Asp Thr Leu Met Ile Ser Arg
20 25 30

Thr Pro Glu Val Thr Cys Val Val Val Asp Val Ser His Glu Asp Pro
35 40 45

Glu Val Lys Phe Asn Trp Tyr Val Asp Gly Val Glu Val His Asn Ala
50 55 60

Lys Thr Lys Pro Arg Glu Glu Gln Tyr Asn Ser Thr Tyr Arg Val Val
65 70 75 80

Ser Val Leu Thr Val Leu His Gln Asp Trp Leu Asn Gly Lys Glu Tyr
85 90 95

Lys Cys Lys Val Ser Asn Lys Ala Leu Gly Ala Pro Ile Glu Lys Thr
100 105 110

Ile Ser Lys Ala Lys Gly Gln Pro Arg Glu Pro Gln Val Cys Thr Leu
115 120 125

Pro Pro Ser Arg Glu Glu Met Thr Lys Asn Gln Val Ser Leu Ser Cys
130 135 140

Ala Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Val Ser Lys Leu Thr Val Asp Lys Ser
180 185 190

Arg Trp Gln Gln Gly Asn Val Phe Ser Cys Ser Val Met His Glu Ala
195 200 205

Leu His Asn His Tyr Thr Gln Lys Ser Leu Ser Leu Ser Pro Gly Gly
210 215 220

Gly Gly Gly Ser Gly Gly Gly Gly Ser Asn Phe His Leu Arg Pro Arg
225 230 235 240

```
Asp Leu Ile Ser Asn Ile Asn Val Ile Val Leu Glu Leu Lys Gly Ser
                245                 250                 255

Glu Thr Thr Phe Met Cys Glu Tyr Ala Asp Glu Thr Ala Thr Ile Val
            260                 265                 270

Glu Phe Leu Asn Arg Trp Ile Thr Phe Ser Gln Ser Ile Ile Ser Thr
        275                 280                 285

Leu Thr Gly Ser Gly Pro Ala Ser Ser Ser Thr Lys Lys Thr Gln Leu
    290                 295                 300

Gln Leu Glu His Leu Leu Leu Asp Leu Gln Met Ile Leu Asn Gly Ile
305                 310                 315                 320

Asn Asn Tyr Lys Asn Pro Lys Leu Thr Arg Met Leu Thr Phe Lys Phe
                325                 330                 335

Tyr Met Pro Lys Lys Ala Thr Glu Leu Lys His Leu Gln Cys Leu Glu
            340                 345                 350

Glu Glu Leu Lys Pro Leu Glu Glu Val Leu Asn Leu Ala Gln Ser Lys
        355                 360                 365


<210> SEQ ID NO 28
<211> LENGTH: 398
<212> TYPE: PRT
<213> ORGANISM: Artificial Sequence
<220> FEATURE:
<223> OTHER INFORMATION: CD25-knob

<400> SEQUENCE: 28

His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Glu Glu Met Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Gly Gly Gly Gly Ser Glu Leu Cys Asp Asp Asp Pro
225                 230                 235                 240
```

```
Pro Glu Ile Pro His Ala Thr Phe Lys Ala Met Ala Tyr Lys Glu Gly
                245                 250                 255

Thr Met Leu Asn Cys Glu Cys Lys Arg Gly Phe Arg Arg Ile Lys Ser
            260                 265                 270

Gly Ser Leu Tyr Met Leu Cys Thr Gly Asn Ser Ser His Ser Ser Trp
        275                 280                 285

Asp Asn Gln Cys Gln Cys Thr Ser Ser Ala Thr Arg Asn Thr Thr Lys
    290                 295                 300

Gln Val Thr Pro Gln Pro Glu Glu Gln Lys Glu Arg Lys Thr Thr Glu
305                 310                 315                 320

Met Gln Ser Pro Met Gln Pro Val Asp Gln Ala Ser Leu Pro Gly His
                325                 330                 335

Cys Arg Glu Pro Pro Pro Trp Glu Asn Glu Ala Thr Glu Arg Ile Tyr
            340                 345                 350

His Phe Val Val Gly Gln Met Val Tyr Tyr Gln Cys Val Gln Gly Tyr
        355                 360                 365

Arg Ala Leu His Arg Gly Pro Ala Glu Ser Val Cys Lys Met Thr His
    370                 375                 380

Gly Lys Thr Arg Trp Thr Gln Pro Gln Leu Ile Cys Thr Gly
385                 390                 395


<210> SEQ ID NO 29
<211> LENGTH: 165
<212> TYPE: PRT
<213> ORGANISM: Artificial Sequence
<220> FEATURE:
<223> OTHER INFORMATION: CD25ecd

<400> SEQUENCE: 29

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly
                165


<210> SEQ ID NO 30
<211> LENGTH: 10
<212> TYPE: PRT
<213> ORGANISM: Artificial Sequence
```

<220> FEATURE:
<223> OTHER INFORMATION: linker

<400> SEQUENCE: 30

Gly Gly Gly Gly Ser Gly Gly Gly Gly Ser
1 5 10

<210> SEQ ID NO 31
<211> LENGTH: 373
<212> TYPE: PRT
<213> ORGANISM: Artificial Sequence
<220> FEATURE:
<223> OTHER INFORMATION: IL-2-knob-full

<400> SEQUENCE: 31

His His His His His His Thr Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Gly Ala
100 105 110

Pro Ile Glu Lys Thr Ile Ser Lys Ala Lys Gly Gln Pro Arg Glu Pro
115 120 125

Gln Val Tyr Thr Leu Pro Pro Cys Arg Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Gly Gly Gly Gly Ser Gly Gly Gly Gly Ser Asn Phe
225 230 235 240

His Leu Arg Pro Arg Asp Leu Ile Ser Asn Ile Asn Val Ile Val Leu
245 250 255

Glu Leu Lys Gly Ser Glu Thr Thr Phe Met Cys Glu Tyr Ala Asp Glu
260 265 270

Thr Ala Thr Ile Val Glu Phe Leu Asn Arg Trp Ile Thr Phe Ser Gln
275 280 285

Ser Ile Ile Ser Thr Leu Thr Gly Ser Gly Pro Ala Ser Ser Ser Thr
290 295 300

Lys Lys Thr Gln Leu Gln Leu Glu His Leu Leu Leu Asp Leu Gln Met
305 310 315 320

```
Ile Leu Asn Gly Ile Asn Asn Tyr Lys Asn Pro Lys Leu Thr Arg Met
                325                 330                 335

Leu Thr Phe Lys Phe Tyr Met Pro Lys Lys Ala Thr Glu Leu Lys His
            340                 345                 350

Leu Gln Cys Leu Glu Glu Glu Leu Lys Pro Leu Glu Glu Val Leu Asn
        355                 360                 365

Leu Ala Gln Ser Lys
    370


<210> SEQ ID NO 32
<211> LENGTH: 406
<212> TYPE: PRT
<213> ORGANISM: Artificial Sequence
<220> FEATURE:
<223> OTHER INFORMATION: CD25-hole-full

<400> SEQUENCE: 32

His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Glu Glu Met Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Gly Gly Gly Gly Ser Glu Leu Cys Asp Asp Asp Pro
225                 230                 235                 240

Pro Glu Ile Pro His Ala Thr Phe Lys Ala Met Ala Tyr Lys Glu Gly
                245                 250                 255

Thr Met Leu Asn Cys Glu Cys Lys Arg Gly Phe Arg Arg Ile Lys Ser
            260                 265                 270

Gly Ser Leu Tyr Met Leu Cys Thr Gly Asn Ser Ser His Ser Ser Trp
        275                 280                 285

Asp Asn Gln Cys Gln Cys Thr Ser Ser Ala Thr Arg Asn Thr Thr Lys
    290                 295                 300
```

Gln Val Thr Pro Gln Pro Glu Glu Gln Lys Glu Arg Lys Thr Thr Glu
305 310 315 320

Met Gln Ser Pro Met Gln Pro Val Asp Gln Ala Ser Leu Pro Gly His
325 330 335

Cys Arg Glu Pro Pro Pro Trp Glu Asn Glu Ala Thr Glu Arg Ile Tyr
340 345 350

His Phe Val Val Gly Gln Met Val Tyr Tyr Gln Cys Val Gln Gly Tyr
355 360 365

Arg Ala Leu His Arg Gly Pro Ala Glu Ser Val Cys Lys Met Thr His
370 375 380

Gly Lys Thr Arg Trp Thr Gln Pro Gln Leu Ile Cys Thr Gly Asp Tyr
385 390 395 400

Lys Asp Asp Asp Asp Lys
405

<210> SEQ ID NO 33
<211> LENGTH: 373
<212> TYPE: PRT
<213> ORGANISM: Artificial Sequence
<220> FEATURE:
<223> OTHER INFORMATION: IL-2-hole-full

<400> SEQUENCE: 33

His His His His His His Thr Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Gly Ala
100 105 110

Pro Ile Glu Lys Thr Ile Ser Lys Ala Lys Gly Gln Pro Arg Glu Pro
115 120 125

Gln Val Cys Thr Leu Pro Pro Ser Arg Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Gly Gly Gly Gly Ser Gly Gly Gly Gly Ser Asn Phe
225 230 235 240

His Leu Arg Pro Arg Asp Leu Ile Ser Asn Ile Asn Val Ile Val Leu
245 250 255

```
Glu Leu Lys Gly Ser Glu Thr Thr Phe Met Cys Glu Tyr Ala Asp Glu
            260                 265                 270

Thr Ala Thr Ile Val Glu Phe Leu Asn Arg Trp Ile Thr Phe Ser Gln
        275                 280                 285

Ser Ile Ile Ser Thr Leu Thr Gly Ser Gly Pro Ala Ser Ser Ser Thr
    290                 295                 300

Lys Lys Thr Gln Leu Gln Leu Glu His Leu Leu Leu Asp Leu Gln Met
305                 310                 315                 320

Ile Leu Asn Gly Ile Asn Asn Tyr Lys Asn Pro Lys Leu Thr Arg Met
                325                 330                 335

Leu Thr Phe Lys Phe Tyr Met Pro Lys Lys Ala Thr Glu Leu Lys His
            340                 345                 350

Leu Gln Cys Leu Glu Glu Glu Leu Lys Pro Leu Glu Glu Val Leu Asn
        355                 360                 365

Leu Ala Gln Ser Lys
    370


<210> SEQ ID NO 34
<211> LENGTH: 406
<212> TYPE: PRT
<213> ORGANISM: Artificial Sequence
<220> FEATURE:
<223> OTHER INFORMATION: CD25-knob-full

<400> SEQUENCE: 34

His Thr Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Gly Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Glu Glu Met Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Gly
    210                 215                 220

Gly Gly Gly Ser Gly Gly Gly Gly Ser Glu Leu Cys Asp Asp Asp Pro
225                 230                 235                 240
```

-continued

```
Pro Glu Ile Pro His Ala Thr Phe Lys Ala Met Ala Tyr Lys Glu Gly
                245                 250                 255

Thr Met Leu Asn Cys Glu Cys Lys Arg Gly Phe Arg Arg Ile Lys Ser
            260                 265                 270

Gly Ser Leu Tyr Met Leu Cys Thr Gly Asn Ser Ser His Ser Ser Trp
        275                 280                 285

Asp Asn Gln Cys Gln Cys Thr Ser Ser Ala Thr Arg Asn Thr Thr Lys
    290                 295                 300

Gln Val Thr Pro Gln Pro Glu Glu Gln Lys Glu Arg Lys Thr Thr Glu
305                 310                 315                 320

Met Gln Ser Pro Met Gln Pro Val Asp Gln Ala Ser Leu Pro Gly His
                325                 330                 335

Cys Arg Glu Pro Pro Pro Trp Glu Asn Glu Ala Thr Glu Arg Ile Tyr
            340                 345                 350

His Phe Val Val Gly Gln Met Val Tyr Tyr Gln Cys Val Gln Gly Tyr
        355                 360                 365

Arg Ala Leu His Arg Gly Pro Ala Glu Ser Val Cys Lys Met Thr His
    370                 375                 380

Gly Lys Thr Arg Trp Thr Gln Pro Gln Leu Ile Cys Thr Gly Asp Tyr
385                 390                 395                 400

Lys Asp Asp Asp Asp Lys
                405
```

FUSION POLYPEPTIDE AND POLYPEPTIDE DIMER, AND USE THEREOF

This application claims priority from International Patent Application No. PCT/CN2021/105187, filed 2021 Jul. 8, which claims priority from Chinese Application No. 202010650886.X filed Jul. 8, 2020 and Chinese Application No. 202010651373.0 filed Jul. 8, 2020, the entire disclosures of which are incorporated herein by this reference in its entirety.

REFERENCE TO SEQUENCE LISTING SUBMITTED ELECTRONICALLY

A sequence listing electronically submitted with the present application as an ASCII file named NP2019TC571-Sequence Listing.txt, created on Jan. 6, 2023 and having a size of 4742000 bytes, is incorporated herein by reference in its entirety.

TECHNICAL FIELD

Provided are a fusion polypeptide and a polypeptide dimer. Particularly, provided is a modified immunoregulatory molecule and use thereof for treating a cancer.

BACKGROUND

Regulation of the immune system by a cytokine, such as activation of an immune cell, is a strategy for cancer immunotherapy. However, certain sites on the cytokines influence their functions (e.g., immunomodulatory effect).

For example, interleukin-2 (IL-2) can regulate the function of immune cells. After binding to receptors IL2Rα (CD25), IL2Rβ (CD122) and IL2Rγ (CD132), IL-2 can activate downstream signaling pathways, including JAKI and JAK3 kinases and transcription factor STAT5, to stimulate activation and proliferation of immune cells (such as T cells and natural killer (NK) cells). IL-2 can perform signal transduction through CD25/CD122/CD132 trimer or activate signaling pathway through CD122/CD132 dimer. Binding of CD25 to IL-2 will change the conformation of IL-2, increasing its affinity for CD122/CD132 dimer by 100-fold (KD value increased from InM to 10 μM). CD122/CD132 dimer is mainly expressed on the surface of CD8+ memory T cells and NK cells, while CD25/CD122/CD132 trimer is abundantly expressed on the surface of regulatory T cells (Treg) that play an immunosuppressive role. Therefore, the role of IL-2 is to stimulate or inhibit the activation of the immune system, depending on the activation of different immune cell types.

IL-2 is also a class of potential drugs for cancer immunotherapy that has attracted much attention. Recombinant IL-2 (ALDESLEUKIN) was approved by the U.S. Food and Drug Administration (FDA) in 1998 for the treatment of metastatic melanoma and renal cancer and is the only IL-2-based drug approved so far. However, only 10% of patients respond, and its side effects are significant, mainly due to the two-sided nature of IL-2, requiring a higher dose to stimulate immune activation, but the higher dose can cause side effects like capillary leakage syndrome.

Interleukin-15 (IL-15) can also activate the immune response and play an important role in the differentiation and proliferation of T cells and NK cells, as well as the development of dendritic cells. IL-15 shares a similar mechanism with IL-2 and activates downstream signaling pathways (JAK1/JAK3 and STAT3/STAT5) by binding to CD122/CD132 receptor dimer, but its a receptor is different from IL-2, being a unique IL-15Rα (CD215) receptor. It is generally believed that after binding to the IL-15R α receptor on the cell membrane, IL-15 is presented to the CD122/CD132 receptor with high affinity as "trans" (cell-cell contact) or "cis" (cis, on the same cell). It has also been found that IL-15 can also bind to CD122/CD132 with moderate affinity and function without binding to IL-15Rα.

It is recently reported (Alexandra Berger et al., 2019 J for ImmunoTherapy for Cancer) that IL-15 alone was more effective than the IL-15/IL-15Rα receptor extracellular domain complex in a mouse tumor model for durable antitumor activity. The applicant believes that this may be because although the complex can stimulate immunity quickly and potently, it will also cause immune cells exhaustion more quickly and reduce response durability. Those skilled in the art also know that strong immune stimulation may bring about safety issues.

In addition, cytokines, such as IL-2 and IL-15, have short in vivo half-lives and require continuous injection.

Therefore, it is desirable to develop an engineered recombinant cytokine such as IL-2 and IL-15 that can specifically activate immunity and have an extended half-life, have improved activity, have a more durable ability to activate immunity, and/or have enhanced safety, thereby improving the clinical application and commercial conversion value.

SUMMARY

In the first aspect, provided is a fusion polypeptide, comprising a carrier protein and a polypeptide of interest, wherein the carrier protein has a plurality of helical domains linked with loops, the polypeptide of interest is inserted into a loop of the carrier protein, the carrier protein shields a site of interest on the polypeptide of interest, thereby blocking the accessibility of the site.

In some embodiments, the polypeptide of interest is derived from a cytokine of the four α-helical bundle cytokine family, the cytokine comprises four α-helix bundles of, from N-terminal to C-terminal, helical bundle 1 (H1), helical bundle 2 (H2), helical bundle 3 (H3) and helical bundle 4 (H4).

In some embodiments, the polypeptide of interest is a cytokine of the circularly permutated four α-helical bundle cytokine family, comprising four α-helical bundles of, from N-terminal to C-terminal, H2, H3, H4 and H1; H3, H4, H1 and H2; or H4, H1, H2 and H3.

In some embodiments, the amino acid in the circularly permutated cytokine corresponding to N-terminal of the uncircularly permutated cytokine is linked to the amino acid corresponding to C-terminal of the uncircularly permutated cytokine via a linker. In some embodiments, the linker is a GS linker or a polyglycine linker having a length of 1-10 amino acids.

In some embodiments, the polypeptide of interest is selected from the group consisting of a circularly permutated IL-2 and a circularly permutated IL-15.

In some embodiments, the circularly permutated IL-2 comprises four α-helical bundles of, from N-terminal to C-terminal, H3, H4, H1 and H2, or H4, H1, H2 and H3. In some embodiments, the circularly permutated IL-2 comprises an amino acid sequence of SEQ ID NO: 2, 3, 4 or 5. In some embodiments, the site of interest is a CD25 binding site.

In some embodiments, the circularly permutated IL-15 comprises four α-helical bundles of, from N-terminal to C-terminal, H3, H4, H1 and H2. In some embodiments, the circularly permutated IL-15 comprises an amino acid sequence of SEQ ID NO: 7. In some embodiments, the site of interest is a CD215 binding site.

In some embodiments, the carrier protein is an albumin, preferably a human serum albumin (HSA). In some embodiments, the loop is selected from the group consisting of loops at D56-L66, A92-P96, D129-E131, Q170-A172, K281-L283, V293-L305, E311-S312, E321-A322, A362-D365, L398-E400, K439-R445, E465-D471, P537-E542 and A561-T566, the positions are numbered by reference to SEQ ID NO: 16. In some embodiments, the polypeptide of interest is a circularly permutated IL-2, the loop is selected from the group consisting of loops at D56-L66, V293-L305 and A362-D365 of the HSA. In some embodiments, the insertion site of the polypeptide of interest is selected from the group consisting of D56, A300, C361 and A362 of the HSA.

In some embodiments, provided is a fusion polypeptide, comprising a carrier protein HSA and a circularly permutated IL-2, wherein the circularly permutated IL-2 comprises four α-helical bundles of, from N-terminal to C-terminal, H3, H4, H1 and H2, or H4, H1, H2 and H3; and wherein the circularly permutated IL-2 is inserted into a loop of the HSA, the loop is selected from the group consisting of loops at D56-L66, A92-P96, D129-E131, Q170-A172, K281-L283, V293-L305, E311-S312, E321-A322, A362-D365, L398-E400, K439-R445, E465-D471, P537-E542, A561-T566, the positions are numbered by reference to SEQ ID NO: 16, the HSA shields the CD25 binding site of the circularly permutated IL-2, thereby blocking the accessibility of the site. In some embodiments, the circularly permutated IL-2 comprises an amino acid sequence of SEQ ID NO: 2, 3, 4 or 5. In some embodiments, the loop is selected from the group consisting of loops at D56-L66, V293-L305 and A362-D365 of the HSA. In some embodiments, the insertion site of the circularly permutated IL-2 is selected from the group consisting of D56, A300, C361 and A362 of the HSA.

In some embodiments, provided is a fusion polypeptide, comprising a carrier protein HSA and a circularly permutated IL-15, wherein the circularly permutated IL-15 comprises four α-helical bundles of, from N-terminal to C-terminal, H3, H4, H1 and H2; and wherein the circularly permutated IL-15 is inserted into a loop of the HSA, the loop is selected from the group consisting of loops at D56-L66, A92-P96, D129-E131, Q170-A172, K281-L283, V293-L305, E311-SS312, E321-A322, A362-D365, L398-E400, K439-R445, E465-D471, P537-E542 and A561-T566, the positions are renumbered by reference to SEQ ID NO: 16, the HSA shields the CD215 binding site of the circularly permutated IL-15, thereby blocking the accessibility of the site. In some embodiments, the circularly permutated IL-15 comprises an amino acid sequence of SEQ ID NO: 7.

In some embodiments, provided is a fusion polypeptide, comprising an amino acid sequence of one of SEQ ID NOs: 8-11.

Provided is also a pharmaceutical composition, comprising the fusion polypeptide according to the present disclosure.

In the second aspect, provided is a polypeptide dimer, comprising a first polypeptide and a second polypeptide, wherein the first polypeptide comprises a first dimerization domain and a polypeptide of interest, wherein the polypeptide of interest is located at the first end of the first dimerization domain, wherein the second polypeptide comprises a second dimerization domain and a binding domain, wherein the binding domain is located at the first end of the second dimerization domain, wherein the first polypeptide forms a dimer with the second polypeptide through the first dimerization domain and the second dimerization domain, and wherein the first end of the first dimerization domain is adjacent to the first end of the second dimerization domain, the binding domain is capable of binding to the site of interest on the polypeptide of interest.

In some embodiments, the polypeptide of interest is derived from a cytokine of the four α-helical bundle cytokine family, the cytokine comprises four α-helix bundles of, from N-terminal to C-terminal, helical bundle 1 (H1), helical bundle 2 (H2), helical bundle 3 (H3) and helical bundle 4 (H4). In some embodiments, the polypeptide of interest is a cytokine of the circularly permutated four α-helical bundle cytokine family, comprising four α-helical bundles of, from N-terminal to C-terminal, H2, H3, H4 and H1; H3, H4, H1 and H2; or H4, H1, H2 and H3.

In some embodiments, the amino acid in the circularly permutated cytokine corresponding to N-terminal of the natural cytokine is linked to the amino acid corresponding to C-terminal of the natural cytokine via a linker. In some embodiments, the linker is a GS linker or a polyglycine linker having a length of 1-10 amino acids.

In some embodiments, the polypeptide of interest is a circularly permutated IL-2 or a circularly permutated IL-15.

In some embodiments, the circularly permutated IL-2 comprises four α-helical bundles of, from N-terminal to C-terminal, H3, H4, H1 and H2, or H4, H1, H2 and H3. In some embodiments, the circularly permutated IL-2 comprises an amino acid sequence of SEQ ID NO: 21. In some embodiments, the site of interest is a CD25 binding site, the binding domain is an extracellular domain of CD25.

In some embodiments, the circularly permutated IL-15 comprises four α-helical bundles of, from N-terminal to C-terminal, H3, H4, H1 and H2. In some embodiments, the circularly permutated IL-15 comprises an amino acid sequence of SEQ ID NO: 22. In some embodiments, the site of interest is a CD215 binding site, the binding domain is an extracellular domain of CD215.

In some embodiments, the first and second dimerization domains comprise heavy chain constant regions CH2 and CH3 of immunoglobulin (Ig). In some embodiments, the Ig is human Ig, for example human IgG1. In some embodiments, the first dimerization domain forms Fc region of the human IgG1 with the second dimerization domain. In some embodiments, the Fc region of the human IgG1 is modified. In some embodiments, the first dimerization domain comprises an amino acid sequence of SEQ ID NO: 23, and the second dimerization domain comprises an amino acid sequence of SEQ ID NO: 24; or the first dimerization domain comprises an amino acid sequence of SEQ ID NO: 24, and the second dimerization domain comprises an amino acid sequence of SEQ ID NO: 23.

In some embodiments, the first end of the first dimerization domain is C-terminal, and the first end of the second dimerization domain is C-terminal.

In some embodiments, the polypeptide dimer according to the present disclosure comprises a first polypeptide and a second polypeptide, wherein the first polypeptide comprises a first chain of the Fc region of the human IgG1 and a circularly permutated IL-2, the circularly permutated IL-2 is linked to C-terminal of the first chain of the Fc region of the human IgG1, wherein the second polypeptide comprises a second chain of the Fc region of the human IgG1 and a CD25 extracellular domain, the CD25 extracellular domain is linked to C-terminal of the second chain of the Fc region of the human IgG1, and the circularly permutated IL-2 comprises four α-helical bundles of, from N-terminal to C-terminal, H3, H4, H1 and H2; or H4, H1, H2 and H3.

In some embodiments, the circularly permutated IL-2 comprises an amino acid sequence of SEQ ID NO: 21.

In some embodiments, the polypeptide dimer according to the present disclosure comprises a first polypeptide and a second polypeptide, wherein the first polypeptide comprises a first chain of the Fc region of the human IgG1 and a circularly permutated IL-15, the circularly permutated IL-15 is linked to C-terminal of the first chain of the Fc region of the human IgG1, wherein the second polypeptide comprises a second chain of the Fc region of the human IgG1 and a CD215 extracellular domain, the CD215 extracellular domain is linked to C-terminal of the second chain of the Fc region of the human IgG1, and the circularly permutated IL-15 comprises four α-helical bundles of, from N-terminal to C-terminal, H3, H4, H1 and H2.

In some embodiments, the circularly permutated IL-2 comprises an amino acid sequence of SEQ ID NO: 22.

In some embodiments, the first chain comprises an amino acid sequence of SEQ ID NO: 23 and the second chain comprises an amino acid sequence of SEQ ID NO: 24; or the first chain comprises an amino acid sequence of SEQ ID NO: 24 and the second chain comprises an amino acid sequence of SEQ ID NO: 23.

Provided is also a pharmaceutical composition, comprising the polypeptide dimer according to the present disclosure.

In the third aspect, provided is a method for treating a cancer or for activating an immune cell or improving proliferation of an immune cell (e.g., T cell or NK cell), comprising administering a subject in need thereof an effective amount of the fusion polypeptide, polypeptide dimer or pharmaceutical composition according to the present disclosure.

Provided is also use of the fusion polypeptide, polypeptide dimer or pharmaceutical composition according to the present disclosure for the manufacture of a medicament for treating a cancer or for activating an immune cell or improving proliferation of an immune cell (e.g., T cell or NK cell).

In some embodiments, provided is the fusion polypeptide, polypeptide dimer or pharmaceutical composition according to the present disclosure for use in treating a cancer or in activating an immune cell or improving proliferation of an immune cell (e.g., T cell or NK cell).

In the third aspect, provided are a polynucleotide, encoding the fusion polypeptide or polypeptide dimer according to the present disclosure, a vector comprising the polynucleotide, and a host cell comprising the polynucleotide or the vector.

DETAILED DESCRIPTION

Figure 1:
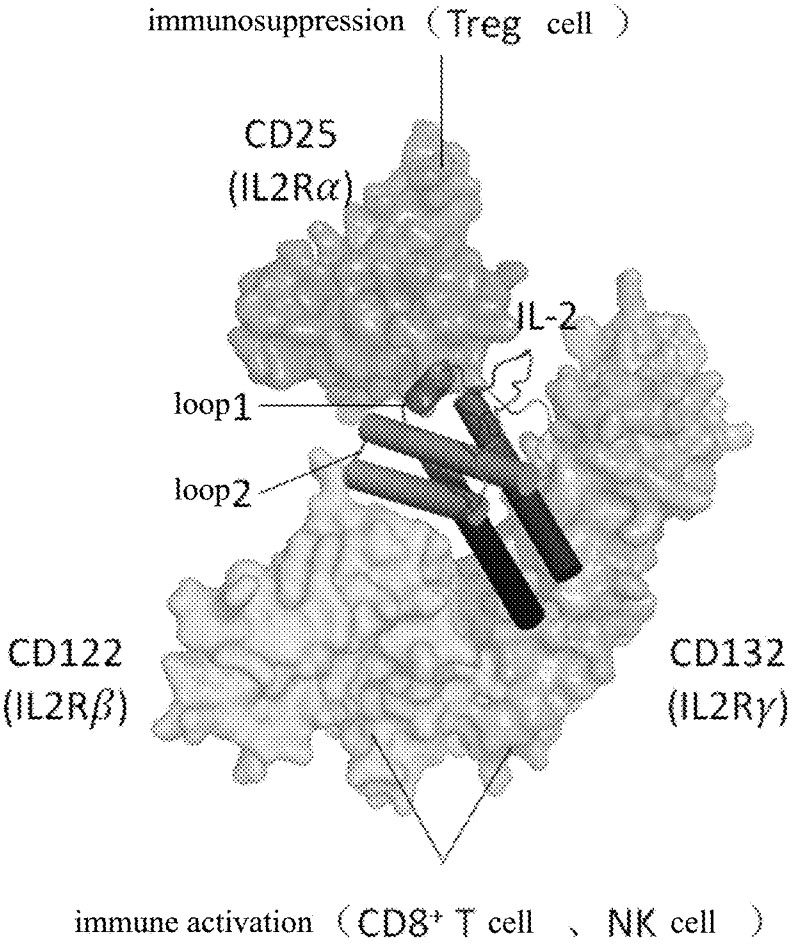
FIG. 1 shows the schematic diagram of the three-dimensional structure of wild-type IL-2 binding to its receptor (based on PDB No. 2ERJ), where "loop 1" corresponds to S95-L100 of native IL-2, and "loop 2" corresponds to N50-P54 of native IL-2. Unless otherwise stated, the positions referring to IL-2 herein are numbered by reference to the IL-2 precursor sequence of SEQ ID NO: 1 (UniProt P60568), where amino acid residues 1-21 are the signal peptide sequence, and the sequence of natural IL-2 is amino acid residues 22-153 of SEQ ID NO: 1.

While the present disclosure will be described in view of the embodiments below, it should be understood that they are not intended to limit the present disclosure to those embodiments. Rather, the present disclosure is intended to cover all alternatives, modifications and equivalents as defined in the claims. Those skilled in the art will understand that many methods and materials similar or equivalent to those described herein could be used in the practice of the present disclosure. The present disclosure is not limited to the methods and materials as described. In the event that one or more of the cited literature, patents and similar materials differs from or contradicts with those herein, including but not limited to the defined term, term usage, described techniques or the like, this present disclosure shall prevail. Unless otherwise defined, all technical and scientific terms used herein have the same meaning as commonly understood by those skilled in the art to which present disclosure belongs. Although methods and materials similar or equivalent to those described herein can be used in the practice or testing of the present disclosure, suitable methods and materials are described below. All publications, patent applications, patents and other references mentioned herein are incorporated by reference in their entirety.

I. Definition

As used herein, the term "peptide" refers to a chain of at least two amino acids linked by peptide bonds. The term "polypeptide" is used interchangeably herein with the term "protein" and refers to a chain containing ten or more amino acids residues. All peptide and polypeptide formulae or sequences herein are written from left to right, indicating the direction from the amino terminal to the carboxy terminal.

As used herein, the term "dihedral angle in peptide chain" refers to the angle at which two adjacent peptide bond planes can rotate around the a carbon atom between these two peptide bond planes.

In the context of peptides, the terms "amino acid", "residue" and "amino acid residue" are used interchangeably and include naturally occurring amino acids and non-natural amino acids in proteins. The one-letter and three-letter nomenclature of the naturally occurring amino acids in proteins use the terminology commonly used in the art, and reference can be made to Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

| Amino acid | One-letter | Three-letter |
|---|---|---|
| alanine | A | Ala |
| arginine | R | Arg |
| asparagine | N | Asn |
| aspartate | D | Asp |
| cysteine | C | Cys |
| glutamine | Q | Gln |
| glutamate | E | Glu |
| glycine | G | Gly |
| histidine | H | His |
| isoleucine | I | Ile |
| leucine | L | Leu |
| lysine | K | Lys |
| methionine | M | Met |
| phenylalanine | F | Phe |
| proline | P | Pro |
| serine | S | Ser |
| threonine | T | Thr |
| tryptophan | W | Trp |
| tyrosine | Y | Tyr |
| valine | V | Val |

As used herein, the term "polynucleotide" or "nucleic acid molecule" includes a DNA molecule (e.g., cDNA or genomic DNA) and an RNA molecule (e.g., mRNA) and an analog of DNA or RNA produced with a nucleotide analog. The nucleic acid molecule may be single-stranded or double-stranded, preferably double-stranded DNA.

The nucleic acid can be synthesized using nucleotide analogs or derivatives thereof (e.g., inosine or phosphorothioate nucleotides). Such nucleotides can be used, for example, to prepare a nucleic acid with altered base-pairing ability or increased nuclease-resistance.

As used herein, the term "encode" refers to the amino acid sequence of a polynucleotide that directly specifies its protein product. The boundaries of the coding sequence are generally defined by an open reading frame, which usually begins with an ATG initiation codon or another initiation codon like GTG and TTG, and ends with a stop codon like TAA, TAG and TGA. A coding sequence can be DNA, cDNA or a recombinant nucleotide sequence.

As used herein, the term "hybridize" is nucleotide sequences that are at least about 90%, preferably at least about 95%, more preferably at least about 96%, more preferably at least 98% homologous to each other generally remain hybridized to each other under given stringent hybridization and washing conditions.

Those skilled in the art are aware of various conditions for hybridization, such as stringent hybridization conditions and highly stringent hybridization conditions. See, for example, Sambrook et al., 1989, Molecular Cloning, A Laboratory Manual, Cold Spring Harbor Press, N.Y.; and Ausubel et al. (eds.), 1995, Current Protocols in Molecular Biology, John Wiley & Sons, N.Y.

As used herein, "amino acid percent identity" or "amino acid sequence percent identity" refers to comparison of the amino acids of two polypeptides that, when optimally aligned, have approximately the same amino acid percentage as specified. For example, "95% amino acid identity" refers to comparison of the amino acids of two polypeptides that, when optimally aligned, are 95% identical in amino acids.

For the present invention, to determine the identity percentage of two amino acid sequences or two nucleic acid sequences, the sequences are aligned for optimal comparison (e.g., gaps can be introduced in the first amino acid or nucleic acid sequence to be compared with the second amino acid sequence or nucleic acid sequence for optimal alignment). The amino acid residues or nucleotides at corresponding amino acid positions or nucleotide positions are then compared. When a position in the first sequence is occupied by the same amino acid residue or nucleotide at the corresponding position in the second sequence, these molecules are identical at this position. The identity percentage between two sequences is a function of the number of identical positions shared by the sequences (i.e., identity percentage=number of identical positions/total number of positions (i.e., overlapping positions)×100). Preferably, the two sequences are of the same length. Those skilled in the art know that different computer programs can be used to determine the identity between two sequences.

As used herein, the term "conservative substitution", also referred to as substitution by a "homologous" amino acid residue, refers to a substitution in which the amino acid residue is replaced by an amino acid residue with a similar side chain, e.g., an amino acid with basic side chain (such as, lysine, arginine and histidine), an amino acid with acidic side chains (such as, aspartate, glutamate), an uncharged amino acid with polar side chain (such as, glycine, asparagine, glutamine, serine, threonine, tyrosine, cysteine), an amino acid with non-polar side chain (such as, alanine, valine, leucine, isoleucine, proline, phenylalanine, methionine, tryptophan), a β-branched side chain amino acid (such as, threonine, valine, isoleucine) and an amino acid with aromatic side chain (such as, tyrosine, phenylalanine, tryptophan, histidine).

A conservative amino acid substitution generally has minimal effect on the activity of the resulting protein. Such a substitution is described below. A conservative substitution is the replacement of an amino acid with another amino acid which is similar in size, hydrophobicity, charge, polarity, steric characteristic, aromaticity, etc. A substitution is usually conservative when it is desired to fine-tune the properties of a protein.

As used herein, "homologous" amino acid residues refer to amino acid residues that have similar chemical properties with respect to hydrophobicity, charge, polarity, steric characteristics, aromatic characteristics, etc. Examples of amino acids that are homologous to each other include positively-charged amino acids lysine, arginine, histidine; negatively charged amino acids glutamate, aspartate; hydrophobic amino acids glycine, alanine, valine, leucine, isoleucine, proline, phenylalanine; polar amino acids serine, threonine, cysteine, methionine, tryptophan, tyrosine, asparagine, glutamine; aromatic phenylalanine, tyrosine, tryptophan; amino acids with chemically-similar side groups serine and threonine; or glutamine and asparagine; or leucine and isoleucine.

Examples of conservative substitutions of amino acids in proteins include: Ser substituting Ala, Lys substituting Arg, Gln or His substituting Asn, Glu substituting Asp, Ser substituting Cys, Asn substituting Gln, Asp substituting Glu, Pro substituting Gly, Asn or Gln substituting His, Leu or Val substituting Ile, Ile or Val substituting Leu, Arg or Gln substituting Lys, Leu or Ile substituting Met, Met, Leu or Tyr substituting Phe, Thr substituting Ser, Ser substituting Thr, Tyr substituting Trp, Trp or Phe substituting Tyr, and Ile or Leu substituting Val.

As used herein, the term "expression" includes any step involved in the production of a polypeptide, including but not limited to transcription, post-transcriptional modification, translation, post-translational modification and secretion.

As used herein, the term "cytokine" refers to a series of small molecule proteins with a wide range of biological activities that are synthesized and secreted upon stimulation by immune cells (such as monocytes, macrophages, T cells, B cells, NK cells, etc.) and some non-immune cells (endothelial cells, epidermal cells, fibroblasts, etc.). Cytokines generally regulate cell growth and differentiation as well as immune responses, by binding to corresponding receptors.

As used herein, the term "four α-helical bundle cytokine family" refers to cytokines comprising four α-helical bundles in the tertiary structure. A cytokine in the native (wild-type) four α-helical bundle cytokine family comprising four α-helix bundles of, from N-terminal to C-terminal, helical bundle 1 (H1), helical bundle 2 (H2), helical bundle 3 (H3) and helical bundle 4 (H4). The cytokines in the four α-helical bundle cytokine family comprise but not limited to IL-2, IL-4, IL-6, IL-7, IL-9, IL-15, IL-21, G-CSF and GM-CSF.

As used herein, the term "circular permutation" refers to modification of the arrangement order of the four α-helical bundles in the primary structure of the cytokines of the four α-helical bundle cytokine family. For example, a circularly permutated cytokine comprises four α-helix bundles of, from N-terminal to C-terminal, H2, H3, H4 and H1; H3, H4, H1 and H2; or H4, H1, H2 and H3. Circular permutation involves the following design of polypeptides: N-terminal and C-terminal of a polypeptide (original polypeptide, such as wild-type four α-helical bundle cytokine) are fused (either directly or via a linker) to form a circular molecule, and the circular molecule is opened (cleaved or broken) between H1 and H2, H2 and H3 or H3 and H4 to form a new linear polypeptide with N-terminal and C-terminal different from the original polypeptide. The circular permutation maintains the sequence, structure and function of the polypeptide (except the optional linker), while creating new C-terminal and N-terminal at different positions. The circular permutation also includes any process that produces the circularly permutated linear molecules described herein. Typically, the circularly permutated polypeptides are expressed directly as linear molecules without real steps of cyclization and opening.

For a polypeptide, "linker" or "linker sequence" refers to an amino acid sequence covalently linked to the N-terminal and/or C-terminal of the polypeptide. The linker can be used to link N-terminal and C-terminal of the same polypeptide (as in circular permutation), or in the same meaning to link the N-terminal and C-terminal of different polypeptides to form a fusion polypeptide. The linker also involves the polynucleotide encoding the amino acid sequence of the linker. In general, the linker does not have a specific biological activity. However, the amino acids constituting the linker can be selected based on certain properties of the linker or the resulting molecule, such as flexibility, hydrophilicity, net charge or whether it is proteolytically sensitive, and non-immunogenicity.

As used herein, a "wild-type" polypeptide refers to a naturally occurring polypeptide.

As used herein, the term "modification" refers to the modification of a polynucleotide or polypeptide sequence, including but not limited to substitution, deletion, insertion and/or addition of one or more nucleotides or amino acids. Modifications also include chemical modifications that do not alter the sequence of the polynucleotide or polypeptide, such as polynucleotide methylation, polypeptide glycosylation, etc. As used herein, modifications also include circular permutation as described above.

As used herein, the term "opening site" refers to the position in a circular molecule where peptide bonds are eliminated to form new amino-terminal and carboxyl-terminal during circularly permutation process, or the corresponding position in the polynucleotide encoding the polypeptide. The opening site is designated by the positions of a pair of amino acids located between the amino-terminal and carboxyl-terminal of the wild-type polypeptide, and these amino acids become the new amino-terminal and carboxyl-terminal of the circularly permutated polypeptide. For example, in IL-2 (97/96), the new N-terminal corresponds to the residue at position 97 of natural IL-2, and the new C-terminal corresponds to the residue at position 96 of natural IL-2; in IL-15 (105/102), the new N-terminal corresponds to the residue at position 105 of natural IL-15, and the new C-terminal corresponds to the residue at position 102, and residues at positions 103 and 104 of natural IL-15 are removed.

As used herein, the term "receptor" refers to a protein present on the cell surface which binds to a ligand, and also covers a soluble receptor which is not present on the cell surface and has a corresponding cell surface receptor or is associated with a corresponding cell surface receptor. A cell surface receptor is generally composed of different domains or subunits with different functions, such as an extracellular domain containing a region interacting with a ligand, a transmembrane domain anchoring the receptor in the cell membrane, and an intracellular effector domain generating a cellular signal in response to ligand binding (signal transduction). A soluble receptor is typically composed of one or more extracellular domains proteolytically cleaved from the membrane anchoring region.

As used herein, the term "variant" refers to a polypeptide which differs from a reference polypeptide but retains essential properties. A typical variant of a polypeptide has a primary amino acid sequence which differs from the reference polypeptide. The difference is always limited such that the sequences of the reference polypeptide and the variant are overall very similar and identical in many regions. The amino acid sequence of the variant and that of the reference polypeptide may differ by one or more modifications (e.g., substitution, addition and/or deletion). A substituted or inserted amino acid residue may or may not be one encoded by the genetic code. A variant of a polypeptide may be naturally occurring, such as an allelic variant, or be artificially produced. In addition, the term "variant" as used herein encompasses a circularly permutated variant of a polypeptide.

As used herein, the term "carrier protein" refers to a protein which is fused to a molecule of interest (e.g., a polypeptide or hapten) to facilitate the delivery of the protein of interest, prolong its half-life, render the hapten immunogenic. The carrier protein per se does not have the biological activity of the molecule of interest. The carrier protein used herein has a plurality of helical structures connected by loop(s), that is, has a "helix-loop-helix" structure, for example, albumin, such as human serum albumin (HSA), albumin binding protein, or the like.

As used herein, the "insertion site" of a polypeptide of interest in a carrier protein refers to the position of residue of the carrier protein closest to N-terminal of the polypeptide of interest in the primary structure after the polypeptide of interest is inserted into the carrier protein.

As used herein, a carrier protein "shielding" a site of interest means that the carrier protein sterically hinders the binding of the site of interest to its receptor, i.e., the carrier protein sterically clashes with the receptor.

As used herein, "accessibility of a site" refers to the ability of a site to contact and bind to its binding partner. When the accessibility of a site is blocked, it cannot contact and bind to its binding partner.

As used herein, the term "immunoglobulin (Ig)" refers to a globulin with antibody activity or chemical structure which is similar to antibody molecule. A natural immunoglobulin is a tetrapeptide chain structure composed of two identical light chains and two identical heavy chains linked via interchain disulfides.

As used herein, the term "Fc fragment" or "Fc region" is part of an immunoglobulin, where Ig is hydrolyzed by papain, cleaving the Ig into two identical Fab fragments and an Fc fragment. The Fc fragment of a native antibody comprises two identical polypeptides linked by disulfides. Each polypeptide comprises two heavy chain constant regions (CH2 and CH3, such as Fc region of IgG), or three heavy chain constant regions (CH2, CH3 and CH4, such as Fc region of IgM and IgE).

As used herein, the term "signal peptide" refers to a short peptide which directs the transfer of a newly synthesized protein to the secretory pathway. Generally, the signal peptide is located at N-terminal of the newly synthesized protein, with a length of, for example, 5-30 amino acid residues. The signal peptide can be removed during protein processing, such that the mature protein does not contain the signal peptide.

As used herein, the term "treatment" refers to a method of obtaining a beneficial or desired result, including but not limited to eradicating or improving the underlying disease being treated. Similarly, the treatment benefit can be obtained by eliminating or improving one or more physiological symptoms related to a basic disease. In this way, although the subject may still suffer from the basic disease, improvements have been observed in the subject.

As used herein, the terms "therapeutically effective amount" and "therapeutically effective dose" refer to the amount of active component. When administered in a single dose or repeated dose, the effective amount can achieve a detectable beneficial effect, including but not limited to the effect on any symptom, aspect, measured parameter or feature of a disease or disorder.

As used herein, the term "dose" refers to the amount administered to a subject once (unit dose) or twice or more within a defined time interval. For example, a dose may refer to the amount administered in one day, two days, one week, two weeks, three weeks or one or more months (for example, by one administration, or two or more administrations).

As used herein, the term "half-life" refers to the time consumed by the reduction of the in vivo concentration of a target molecule by 50%. If the target molecule remains in vivo in the biological matrix (blood, serum, plasma, tissue) for a longer time than an appropriate control, its half-life will be increased. Compared with the appropriate control, the half-life can be increased by 10%, 20%, 30%, 40%, 50% or more.

Those skilled in the art are familiar with the method of pharmacokinetic analysis and determination of ligand half-life. Detailed information can be found in Kenneth, A et al., Chemical Stability of Pharmaceuticals: A Handbook for Pharmacists and Peters et al., Pharmacokinetic analysis: A Practical Approach (1996). Reference can also be made to "Pharmacokinetics", M Gibaldi & D Perron, published by Marcel Dekker, 2.sup.nd Rev. ex edition (1982).

II. Circular Permutation of the Polypeptide

Circular permutation refers to change of the order in the primary structure of the four α-helical bundles in the cytokine of the four α-helical bundle cytokine family. For example, the circularly permutated four α-helical bundle cytokine comprises four α-helical bundles of, from N-terminal to C-terminal, H2, H3, H4 and H1; H3, H4, H1 and H2; or H4, H1, H2 and H3. Circular permutation involves the following design of polypeptides: N-terminal and C-terminal of the polypeptide (original polypeptide, such as wild-type four α-helical bundle cytokine) are fused (either directly or via a linker) to form a circular molecule, and the circular molecule is opened between H1 and H2, H2 and H3 or H3 and H4 (cleave or break) to form a new linear polypeptide with different N-terminal and C-terminal from the original polypeptide.

Importantly, the circularly permutated peptide provides optimized ends for fusion with other peptides while retaining the biological activity of the original peptide. If the new end blocks the essential region of the initial peptide, it may lose its activity. Similarly, if connecting the original end will destroy the activity, the circularly permutated peptide cannot retain its biological activity. Therefore, there are two requirements for the production of an active circulating permutated protein: 1) connecting the end of the initial polypeptide does not destroy its biological activity; 2) there must be at least one "opening site" in the initial polypeptide, where a new end can be formed without destroying the region critical to its folding and biological activity.

Therefore, in general, in the natural folding state (original protein), the original N-terminal and C-terminal of the candidate peptide for circularly permutation are very close, for example, the distance between the N-terminal and C-terminal of the original protein is less than or equal to 20 A.

For fusing with the desired polypeptide fusion partner and reducing the length of the required linker, the location of the new terminal is advantageous in geometry, structure and function (relative to the natural terminal).

Figure 2:
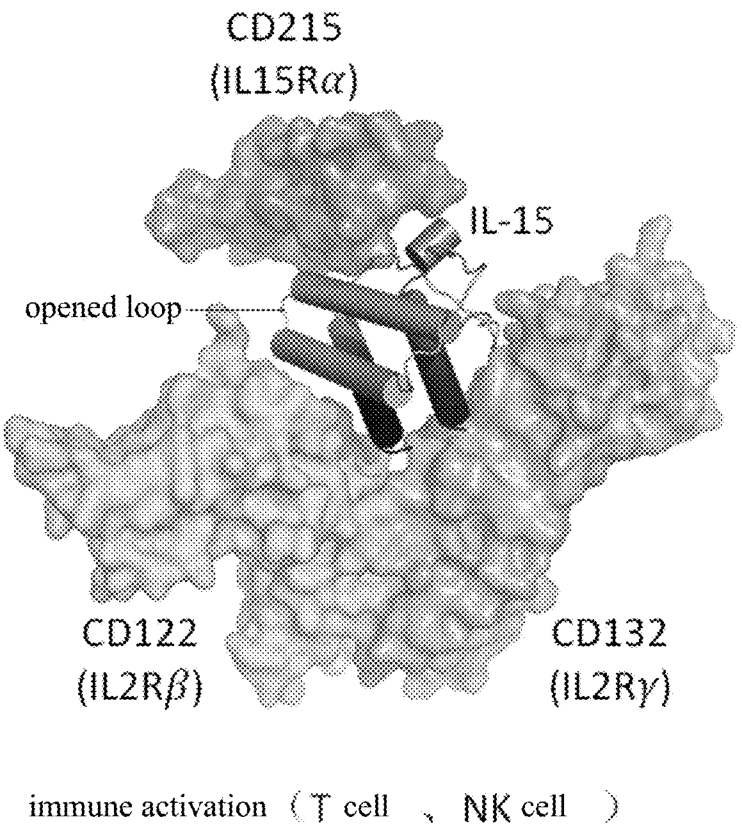
FIG. 2 shows the schematic diagram of the three-dimensional structure of wild-type IL-15 binding to its receptor (based on PDB No. 4GS7), where the "opened loop" corresponds to S102-A105 of natural IL-15. Unless otherwise stated, the positions of IL-15 are numbered by reference to the IL-15 precursor sequence of SEQ ID NO: 6 (UniProt P40933), wherein residues 1-48 are the signal peptide, and the sequence of natural IL-15 is amino acid residues 49-162 of SEQ ID NO: 6.

FIG. 1 shows the structure of IL-2, wherein loop 1 and loop 2 are examples of positions where new ends are formed. FIG. 2 shows the structure of IL-15, wherein the "opened loop" is an example of the position where a new end is formed.

In some embodiments, to perform circular permutation on IL-2, the engineering design is conducted for the recombinant construct, where the natural N-terminal and C-terminal of IL-2 are linked via a linker, and the cyclic molecule is opened between amino acid residues A93-R103 or N50-L56 to form a linear molecule with new N-terminal and C-terminal. In some embodiments, new N-terminal is formed at amino acid residue R103, new C-terminal is formed at amino acid residue A93 and amino acid residue Q94-P102 is deleted, i.e., IL-2 (R103/A93). In some embodiments, the circularly permutated IL-2 is IL-2 (L56/N50), IL-2 (L56/K55) or IL-2 (N53/K52). In some embodiments, new N-terminal is formed at amino acid residue N97 and new C-terminal is formed at amino acid residue K96, i.e., IL-2 (N97/K96).

In some embodiments, the circularly permutated IL-2 comprises an amino acid sequence of SEQ ID NO: 2, 3, 4 or 5.

In some embodiments, to perform circular permutation on IL-15, the engineering design is conducted for the recombinant construct, where the natural N-terminal and C-terminal of IL-15 are linked via a linker to form a cyclic molecule, and the cyclic molecule is opened between amino acid residence S102-A105 to form a linear molecule with new N-terminal and C-terminal. For example, new C-terminal is formed at amino acid residues S102, G103 or D104, and new N-terminal is formed at G103, D104, A105 or S106. In some embodiments, the circularly permutated IL-15 is IL-15 (G103/S102), IL-15 (D104/S102), IL-15 (A105/S102), IL-15 (S106/S102), IL-15 (S106/G103), IL-15 (A105/G103), IL-15 (D104/G103), IL-15 (A105/D104), IL-15 (S106/D104), IL-15 (S106/A105).

In a preferable embodiment, the length of the linker used to link N-terminal and C-terminal of the initial polypeptide is related to the distance between N-terminal and C-terminal in the original protein. In some embodiments, the linker used to link N-terminal and C-terminal of the initial polypeptide has a length of 1-10 amino acids, such as 1, 2, 3, 4, 5, 6, 7, 8, 9 or 10 amino acids. In some embodiments, the linker has a length of more than 10 amino acids. Preferably, a linker of 3 amino acids e.g., GSG is used to link N-terminal and C-terminal of natural IL-2; a linker of 4 amino acids e.g., GGGG (SEQ ID NO: 17) is used to link N-terminal and C-terminal of natural IL-15.

Those skilled in the art will understand that other modifications can be made to the initial polypeptide, such as amino acid substitution. In some embodiments, residue T23 of natural IL-2 (i.e., T2 of SEQ ID NO: 1) is substituted to A. In some embodiments, residue C145 of natural IL-2 (i.e., C124 of SEQ ID NO: 1) is substituted to S.

In some embodiments, the circularly permutated IL-2 comprises an amino acid sequence of SEQ ID NO: 2, 3, 4 or 5.

In some embodiments, the circularly permutated IL-15 comprises an amino acid sequence of SEQ ID NO: 7.

In some embodiments, the circularly permutated IL-2 comprises an amino acid sequence of SEQ ID NO: 23.

In some embodiments, the circularly permutated IL-15 comprises an amino acid sequence of SEQ ID NO: 24.

III. Fusion Polypeptide

The fusion polypeptide according to the present disclosure comprises a carrier protein and a polypeptide of interest, wherein the carrier protein has a plurality of helical domains linked with a loop, the polypeptide of interest is inserted into the loop of the carrier protein, the carrier protein shields a site of interest on the polypeptide of interest, thereby blocking the accessibility of the site.

The inventors found that when inserting the polypeptide of interest into a loop of the carrier protein, by selecting an appropriate insertion site, adjusting the linker (such as its sequence and/or length) between the polypeptide of interest and the carrier protein, deleting one or more amino acids in the inserted loop, deleting one or more amino acids at N-terminal and/or C-terminal of the polypeptide of interest, or any combination thereof, the dihedral angle in the peptide chain can be employed to control the relative position of the carrier protein and the polypeptide of interest, such that the carrier protein can shield the site of interest.

In some embodiments, the polypeptide of interest is derived from a cytokine of the four α-helical bundle cytokine family, including but not limited to IL-2, IL-4, IL6, IL-7, IL-9, IL15 and IL21. Preferably, the polypeptide of interest is a cytokine of the circularly permutated four α-helical bundle cytokine family. In a preferable embodiment, the polypeptide of interest is circularly permutated IL-2 or IL-15.

Natural IL-2 has binding sites for CD25, CD122 and CD132 (known as IL-2 receptors α, β and γ, respectively). IL-2 can not only bind to CD25/CD122/CD132 trimer to activate T regulatory cells (Treg) expressing the trimer and inhibit immune response, but also bind to CD122/CD132 dimer to activate immune cells (such as CD8+ memory T cell and NK cell) expressing the dimer and stimulate its proliferation. The binding of CD25 to IL-2 will change the conformation of IL-2 and increase its affinity for CD122/CD132 dimer.

Accordingly, in some embodiments, the polypeptide of interest is circularly permutated IL-2, the site of interest is CD25 binding site, and the fusion polypeptide has an activity comparable to or improved over natural IL-2, such as that of activating the JAK1/JAK3 and STAT3/STAT5 signal pathways.

IL-15 can also activate the immune response, which plays an important role in the differentiation and proliferation of T cells and NK cells, as well as the development of dendritic cells.

The working mechanism of IL-15 is similar to that of IL-2. It activates the downstream signal pathways (JAK1/JAK3 and STAT3/STAT5) by binding to CD122/CD132 receptor dimer, but its a receptor is different from that of IL-2 and is a unique IL-15R α (CD215). After binding to IL-15Rα, IL-15 binds to CD122/CD132 with high affinity, while in the case of not binding to IL-15Rα, IL-15 binds to CD122/CD132 with medium affinity.

Accordingly, in some embodiments, the polypeptide of interest is circularly permutated IL-15, the site of interest is CD215 binding site, and the fusion polypeptide has an activity comparable to or improved over natural IL-15, such as that of activating the JAK1/JAK3 and STAT3/STAT5 signal pathways.

Preferably, the carrier protein suitable herein can bind to a newborn Fc receptor (FcRn) (such as albumin), or the carrier protein can bind to a protein which can bind to FcRn (such as albumin binding protein)

Figure 3:
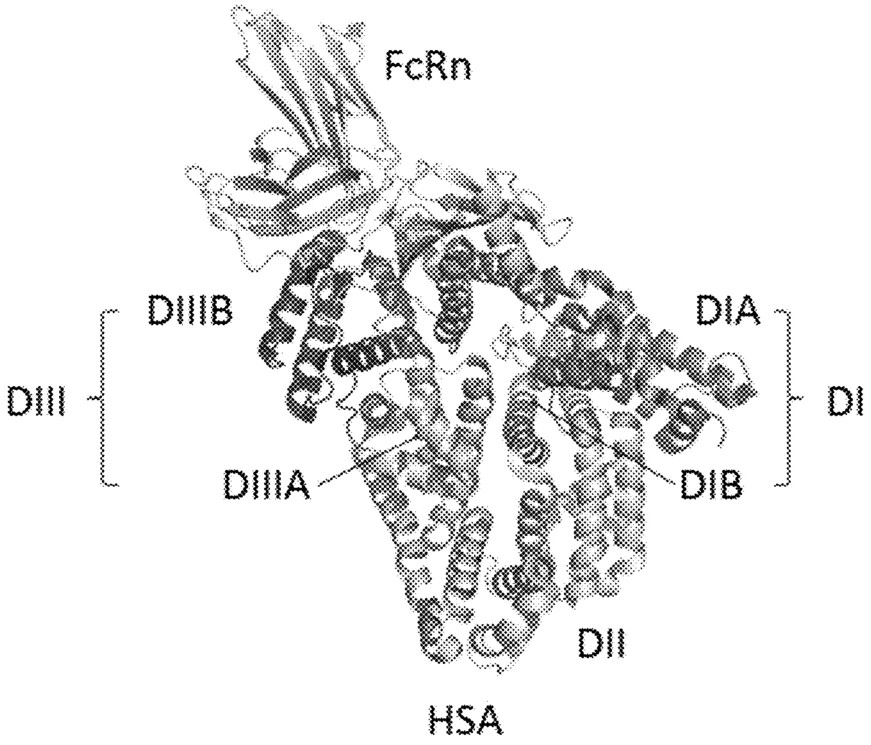
FIG. 3 shows the schematic diagram of the three-dimensional structure of HSA.

Human serum albumin (HSA) is one of the most stable proteins with the highest content (35-50 g/L) in human serum, accounting for half of the proteins in serum. Its main role is to transport substances (such as hormones, fatty acids, or the like), maintain pH and osmotic pressure. HSA herein comprises wild type HSA and modified HSA HSA is a whole α helix protein with a molecular weight of 66.5 kDa. It is composed of three similar domains (DI, DII, DIII) forming a "heart" structure (FIG. 3). HSA can bind to human FcRn under acidic condition (pH<6.5), and then be recovered to the cell surface and released back into the blood, preventing HSA from entering lysosome and being degraded. FcRn mainly bind to DIII and a part of DI.

The precursor sequence of HSA is as shown in SEQ ID NO: 16 (Uniprot P02768). All positions involving HSA herein are numbered with reference to SEQ ID NO: 16. In the precursor sequence of HSA, residues 1-24 is a signal peptide, and natural HSA comprises residues 25-609 of SEQ ID NO: 16.

In some embodiments, the carrier protein is HSA. Preferably, the insertion of the polypeptide of interest does not affect the binding of HSA and FcRn. In some embodiments, the polypeptide of interest is inserted into the loop of HSA, wherein the loop is selected from the group consisting of loops at D56-L66, A92-P96, D129-E131, Q170-A172, K281-L283, V293-L305, E311-S312, E321-A322, A362-D365, L398-E400, K439-R445, E465-D471, P537-E542, A561-T566, and preferably loops at D56-L66, V293-L305 and A362-D365. In some embodiments, the insertion site of the polypeptide of interest is amino acid residue D56, A300, C361 or A362 of HSA.

The relative position between the carrier protein and the polypeptide of interest by deleting one or more amino acids in the loop of the carrier protein such as HSA, or the amino acids in the loop of the carrier protein may not be deleted.

HSA can also be modified to improve its properties. For example, a free cysteines in the wild type HSA can be replaced with another amino acid, such as serine. In some embodiments, the HSA comprises an amino acid substitution C58S.

In some embodiments, the carrier protein has at least 70%, 80%, 90%, 95%, 96%, 97%, 98% or 99% sequence identity to SEQ ID NO: 16, and has an identical or similar structure as wild type HSA.

In some embodiments, N-terminal and C-terminal of the polypeptide of interest is linked to the carrier protein via a linker. In some embodiments, N-terminal of the polypeptide of interest is linked to the carrier protein via a linker, C-terminal of the polypeptide of interest is directly linked to the carrier protein. In some embodiments, N-terminal of the polypeptide of interest is directly linked to the carrier protein, C-terminal of the polypeptide of interest is linked to the carrier protein via a linker. In some embodiments, N-terminal and C-terminal are directly linked to the carrier protein. In some embodiments, the linker has 1, 2, 3, 4, 5, 6, 7, 8, 9, 10, 11, 12, 13, 14, 15, 16, 17, 18, 19, 20 or more amino acids. In some embodiments, the linker is selected from the group consisting of a helical linker, or a flexible linker (e.g., GS linker and polyglycine linker).

In some embodiments, the fusion polypeptide according to the present disclosure comprises a carrier protein HSA and a circularly permutated IL-2, wherein the circularly permutated IL-2 comprises four α-helical bundles of, from N-terminal to C-terminal, H3, H4, H1 and H2, or H4, H1, H2 and H3; and wherein the circularly permutated IL-2 is inserted into a loop of the HSA, the loop is selected from the group consisting of loops at D56-L66, A92-P96, D129-E131, Q170-A172, K281-L283, V293-L305, E311-S312, E321-A322, A362-D365, L398-E400, K439-R445, E465-D471, P537-E542 and A561-T566, the positions are numbered by reference to SEQ ID NO: 16, the HSA shields the CD25 binding site of the circularly permutated IL-2, thereby blocking the accessibility of the site. In some embodiments, the circularly permutated IL-2 comprises an amino acid sequence of SEQ ID NO: 2, 3, 4 or 5. In some embodiments, the loop is selected from the group consisting of loops at D56-L66, V293-L305 and A362-D365 of HSA. In some embodiments, the insertion site of the circularly permutated IL-2 is selected from the group consisting of D56, A300, C361 and A362 of HSA.

In some embodiments, the circularly permutated IL-2 comprises an amino acid sequence of SEQ ID NO: 2. In some embodiments, the loop is a loop at A362-D365 of HSA. Preferably, the insertion site is C361 of HSA. In some embodiments, N-terminal of the circularly permutated IL-2 is linked to C361 of HSA via a linker EAAAKAEAAA (SEQ ID NO: 19), C-terminal is linked to D365 of HSA via a linker GS, and residues 362-364 of HSA are deleted.

In some embodiments, the circularly permutated IL-2 comprises an amino acid sequence of SEQ ID NO: 4. In some embodiments, the loop is a loop at D56-L66 of HSA. Preferably, the insertion site is D56 of HSA. In some embodiments, N-terminal of the circularly permutated IL-2 is linked to D56 of HSA via a linker AAAAAK (SEQ ID NO: 20), C-terminal is directly linked to E57 of HSA.

In some embodiments, the circularly permutated IL-2 comprises an amino acid sequence of SEQ ID NO: 5. In some embodiments, the loop is a ring at V293-L305 of HSA. Preferably, the insertion site is A300 of HSA. In some embodiments, N-terminal of the circularly permutated IL-2 is directly linked to A300 of HSA, C-terminal is linked to D301 of HSA via a linker G.

In some embodiments, the circularly permutated IL-2 consists of an amino acid sequence SEQ ID NO: 4. In some embodiments, the loop is a loop at A362-D365 of HSA. Preferably, the insertion site is A362 of HSA. In some embodiments, N-terminal of the circularly permutated IL-2 is directly linked to A362 of HSA, C-terminal is directly linked to A363 of HSA.

In some embodiments, provided is a fusion polypeptide, comprising a carrier protein HSA and a circularly permutated IL-15, wherein the circularly permutated IL-15 comprises four α-helical bundles of, from N-terminal to C-terminal, H3, H4, H1 and H2; and wherein the circularly permutated IL-15 is inserted into a loop of the HSA, the loop is selected from the group consisting of loops at D56-L66, A92-P96, D129-E131, Q170-A172, K281-L283, V293-L305, E311-SS312, E321-A322, A362-D365, L398-E400, K439-R445, E465-D471, P537-E542 and A561-T566, the positions are renumbered by reference to SEQ ID NO: 16, the HSA shields the CD215 binding site of the circularly permutated IL-15, thereby blocking the accessibility of the site. In some embodiments, the circularly permutated IL-15 comprises an amino acid sequence of SEQ ID NO: 7.

In some embodiments, the fusion polypeptide according to the present disclosure comprises an amino acid sequence of one of SEQ ID NO: 8-11. In some embodiments, the fusion polypeptide according to the present disclosure comprises an amino acid sequence which has at least 70%, 80%, 90%, 95%, 96%, 97%, 98% or 99% sequence identity to one of SEQ ID NO: 8-11, wherein the fusion polypeptide comprises natural CD25 binding site and has an activity comparable to or improved over natural IL-2, such as that of activating the JAK1/JAK3 and STAT3/STAT5 signal pathways.

In some embodiments, the fusion polypeptide according to the present disclosure has more lasting immune stimulating effect. In some embodiments, the fusion polypeptide according to the present disclosure has higher safety.

In some embodiments, as compared to natural IL-2, the fusion polypeptide according to the present disclosure has a half-life increased by 10%, 20%, 30%, 40%, 50%, 60%, 70%, 80%, 90%, 100%, 150%, 200%, 300%, 400%, 500%, 600%, 700%, 800%, 900%, 1000% or more. In some embodiments, as compared to natural IL-15, the fusion polypeptide according to the present disclosure has a half-life increased by 10%, 20%, 30%, 40%, 50%, 60%, 70%, 80%, 90%, 100%, 150%, 200%, 300%, 400%, 500%, 600%, 700%, 800%, 900%, 1000% or more.

IV. Polypeptide Dimer

The polypeptide dimer according to the present disclosure comprises a first polypeptide and a second polypeptide, wherein the first polypeptide comprises a first dimerization domain and a polypeptide of interest, wherein the polypeptide of interest is located at a first end of the first dimerization domain, wherein the second polypeptide comprises a second dimerization domain and a binding domain, wherein the binding domain is located at a first end of the second dimerization domain, wherein the first polypeptide and the second polypeptide form a dimmer with the first dimerization domain and the second dimerization domain, and wherein the first end of the first dimerization domain is adjacent to the first end of the second dimerization domain, the binding domain is capable of binding to the site of interest on the polypeptide of interest.

In some embodiments, the polypeptide of interest is derived from a cytokine of the four α-helical bundle cytokine family, including but not limited to IL-2, IL-4, IL6, IL-7, IL-9, IL15 and IL21. Preferably, the polypeptide of interest is a cytokine of the circularly permutated four α-helical bundle cytokine family. In a preferable embodiment, the polypeptide of interest is circularly permutated IL-2 or IL-15, wherein the circular permutation is as described above.

Native IL-2 has binding sites for CD25, CD122 and CD132 (known as IL-2 receptors α, β and γ, respectively). IL-2 can not only bind to CD25/CD122/CD132 trimer to activate T regulatory cells (Treg) expressing the trimer and inhibit immune response, but also bind to CD122/CD132 dimer to activate immune cells (such as CD8+ memory T cell and NK cell) expressing the dimer and stimulate its proliferation. The binding of CD25 and IL-2 will change the conformation of IL-2 and increase its affinity for CD122/CD132 dimer.

Accordingly, in some embodiments, the polypeptide of interest is circularly permutated IL-2, the site of interest is CD25 binding site, the binding domain is extracellular domain of CD25, and the polypeptide dimer has an activity comparable to or improved over natural IL-2, such as that of activating the JAK1/JAK3 and STAT3/STAT5 signal pathways.

IL-15 can also activate the immune response, which plays an important role in the differentiation and proliferation of T cells and NK cells, as well as the development of dendritic cells. The working mechanism of IL-15 is similar to that of IL-2. It activates the downstream signal pathways (JAK1/JAK3 and STAT3/STAT5) by binding to CD122/CD132 receptor dimer, but its a receptor is different from that of IL-2 and is a unique IL-15Rα (CD215). After binding to IL-15Rα, IL-15 binds to CD122/CD132 with high affinity, while in the case of not binding to IL-15Rα, IL-15 binds to CD122/CD132 with medium affinity.

Accordingly, in some embodiments, the polypeptide of interest is circularly permutated IL-15, the site of interest is CD215 binding site, the binding domain is extracellular domain of CD215, and the polypeptide dimer has an activity comparable to or improved over natural IL-15, such as that of activating the JAK1/JAK3 and STAT3/STAT5 signal pathways.

In the polypeptide dimer according to the present disclosure, the site of interest and the binding domain are located in different (first and second) polypeptides. The first dimerization domain and second dimerization domain form a dimmer, making the site of interest close to the binding domain. The first dimerization domain and second dimerization domain form a dimmer by for example but not limited to covalent bonding, hydrogen bonding, electrostatic interaction and/or van der Waals force, preferably covalent bonding.

In some embodiments, the first dimerization domain and second dimerization domain form a dimmer by disulfide bond. In some embodiments, the first dimerization domain and second dimerization domain comprise heavy chain constant region CH2 and CH3 of immunoglobulin (Ig), such as human Ig (e.g., human IgG1). In some embodiments, the first dimerization domain and second dimerization domain form Fc region of human IgG1.

Various mutations can be introduced in the Fc segment to achieve different functions, for example, to increase the affinity of Fc and FcRn under acidic condition; reduce or increase the affinity of Fc with different Fc γ receptors and C1q to weaken or enhance antibody dependent cytotoxicity (ADCC), antibody dependent cell phagocytosis (ADCP), complement dependent cytotoxicity (CDC) or the like. In some embodiments, Fc region in the polypeptide dimer according to the present disclosure comprises Fc silent mutations, such as L234A+L235A+P329G, so as to reduce ADCC, ADCP and CDC, wherein the amino acid positions in the Fc region are numbered according to IMGT EU numbering rule (imgt.org/IMGTS cientificChart/Numbering/Hu_IGHGnber.html).

In some embodiments, the Fc region is a homodimer, that is, the first dimerization domain has a sequence identical to that of the second dimerization domain. In some embodiments, the Fc region is a heterodimer, that is, the first dimerization domain has a sequence different to that of the second dimerization domain. In some embodiments, a knob-in-hole modification is made to the Fc region. For example, a mutation T366Y (the 1$^{st}$ generation knob-in-hole) or S354C+T366W (the 2$^{nd}$ generation knob-in-hole) is introduced into a polypeptide chain to form a knob chain; and Y407T (the 1$^{st}$ generation knob-in-hole) or Y349C+T366S+L368A+Y407V (the 2$^{nd}$ generation knob-in-hole) is introduced into another polypeptide chain to form a hole chain, where the numbering rule is as described above.

In some embodiments, the first polypeptide comprises a knob chain and the second polypeptide comprises a hole chain. In some embodiments, the first polypeptide comprises a hole chain, and the second polypeptide comprises a knob chain.

In some embodiments, the knob chain comprises an amino acid sequence of SEQ ID NO: 23 or an amino acid sequence which has at least 70%, 80%, 90%, 95%, 96%, 97%, 98% or 99% sequence identity to SEQ ID NO: 23. In some embodiments, the hole chain comprises an amino acid sequence of SEQ ID NO: 24 or an amino acid sequence which has at least 70%, 80%, 90%, 95%, 96%, 97%, 98% or 99% sequence identity to SEQ ID NO: 24.

In some embodiments, the first dimerization domain comprises an amino acid sequence of SEQ ID NO: 23 or an amino acid sequence which has at least 70%, 80%, 90%, 95%, 96%, 97%, 98% or 99% sequence identity to SEQ ID NO: 23, and the second dimerization domain comprises an amino acid sequence of SEQ ID NO: 24 or an amino acid sequence which has at least 70%, 80%, 90%, 95%, 96%, 97%, 98% or 99% sequence identity to SEQ ID NO: 24; or the first dimerization domain comprises an amino acid sequence of SEQ ID NO: 24 or an amino acid sequence which has at least 70%, 80%, 90%, 95%, 96%, 97%, 98% or 99% sequence identity to SEQ ID NO: 24, and the second dimerization domain comprises an amino acid sequence of SEQ ID NO: 23 or an amino acid sequence which has at least 70%, 80%, 90%, 95%, 96%, 97%, 98% or 99% sequence identity to SEQ ID NO: 23.

In some embodiments involving immunoglobulin Fc region, the polypeptide of interest is located at C-terminal of the first dimerization domain (i.e., the first chain of Fc region), and the binding domain is located at C-terminal of the second dimerization domain (i.e., the second chain of Fc region). In some embodiments involving immunoglobulin Fc region, the polypeptide of interest is located at N-terminal of the first dimerization domain (i.e., the first chain of Fc region), and the binding domain is located at N-terminal of the second dimerization domain (i.e., the second chain of Fc region).

In some embodiments, the polypeptide of interest is linked to the first dimerization domain via a linker and the binding domain is linked to the second dimerization domain via a linker. In some embodiments, the linker is a flexible linker. In some embodiments, the linker has 1, 2, 3, 4, 5, 6, 7, 8, 9, 10, 11, 12, 13, 14, 15, 16, 17, 18, 19, 20 or more amino acids. In some embodiments, the linker has 1-20, 2-18, 3-16, 5-15, 6-12 or 8-10 amino acids. In some embodiments, the linker has an amino acid sequence of GGGGSGGGGS (SEQ ID NO: 30).

In some embodiments, the polypeptide dimer according to the present disclosure comprises a first polypeptide and a second polypeptide, wherein the first polypeptide comprises a first chain of Fc region of human IgG1 and a circularly permutated IL-2, the circularly permutated IL-2 is linked to C-terminal of the first chain of Fc region of human IgG1, wherein the second polypeptide comprises a second chain of Fc region of human IgG1 and a CD25 extracellular domain, the CD25 extracellular domain is linked to C-terminal of Fc region of human IgG1, and wherein the circularly permutated IL-2 is as described above, for example the circularly permutated IL-2 consists of an amino acid sequence of SEQ ID NO: 21. In some embodiments, the first chain consists of an amino acid of SEQ ID NO: 23, and the second chain consists of an amino acid sequence of SEQ ID NO: 24; or the first chain consists of an amino acid of SEQ ID NO: 24, and the second chain consists of an amino acid sequence of SEQ ID NO: 23.

In some embodiments, the polypeptide dimer according to the present disclosure comprises a first polypeptide and a second polypeptide, wherein the first polypeptide comprises a first chain of Fc region of human IgG1 and a circularly permutated IL-15, the circularly permutated IL-15 is linked to C-terminal of the first chain of Fc region of human IgG1, wherein the second polypeptide comprises a second chain of Fc region of human IgG1 and a CD215 extracellular domain, the CD215 extracellular domain is linked to C-terminal of the second chain of Fc region of human IgG1, and wherein the circularly permutated IL-15 is as described above, for example, the circularly permutated IL-15 comprises an amino acid sequence of SEQ ID NO: 22. In some embodiments, the first chain comprises an amino acid sequence of SEQ ID NO: 23 and the second chain comprises an amino acid of SEQ ID NO: 24; or the first chain comprises an amino acid sequence of SEQ ID NO: 24 and the second chain comprises an amino acid of SEQ ID NO: 23.

Those skilled in the art will understand that the amino acid sequence of a circularly permutated polypeptide can be modified without reducing its biological activity. Such modifications are well-known to those skilled in the art, and include the addition of a residue, such as methionine added at the amino end to provide an initiation site, or the addition of an additional amino acid at either end to protect the protein from damage by exopeptidase.

Those skilled in the art will understand that other modifications can be made. For example, amino acid substitutions, such as conservative substitutions, can be made without affecting protein activity. Alternatively, the unnecessary region of the molecule can be reduced or completely eliminated. Therefore, in the regions where the molecule per se is not involved in the molecular activity, they can be eliminated or replaced by shorter fragments, which are only used to maintain the correct spatial relationship between the active components of the molecule.

In some embodiments, the circularly permutated IL-2 comprises an amino acid sequence which has at least 70%, 80%, 90%, 95%, 96%, 97%, 98% or 99% sequence identity to SEQ ID NO: 21, wherein the first polypeptide comprises the natural CD25 binding site, and the polypeptide dimer has an activity comparable to or improved over natural IL-2.

In some embodiments, the circularly permutated IL-15 comprises an amino acid sequence which has at least 70%, 80%, 90%, 95%, 96%, 97%, 98% or 99% sequence identity to SEQ ID NO: 22, wherein the first polypeptide comprises the natural CD215 binding site, and the polypeptide dimer has an activity comparable to or improved over natural IL-15.

In some embodiments, the first polypeptide comprises an amino acid sequence of SEQ ID NO: 25, the second polypeptide comprises an amino acid sequence of SEQ ID NO: 26. In some embodiments, the first polypeptide comprises an amino acid sequence which has at 70%, 80%, 90%, 95%, 96%, 97%, 98% or 99% sequence identity to SEQ ID NO: 25, the second polypeptide comprises an amino acid sequence which has at 70%, 80%, 90%, 95%, 96%, 97%, 98% or 99% sequence identity to SEQ ID NO: 26, wherein the first polypeptide comprises the natural CD25 binding site, and the polypeptide dimer has an activity comparable to or improved over natural IL-2.

In some embodiments, the first polypeptide comprises an amino acid sequence of SEQ ID NO: 27, the second polypeptide comprises an amino acid sequence of SEQ ID NO: 28. In some embodiments, the first polypeptide comprises an amino acid sequence which has at 70%, 80%, 90%, 95%, 96%, 97%, 98% or 99% sequence identity to SEQ ID NO: 27, the second polypeptide comprises an amino acid sequence which has at 70%, 80%, 90%, 95%, 96%, 97%, 98% or 99% sequence identity to SEQ ID NO: 28, wherein the first polypeptide comprises the natural CD25 binding site, and the polypeptide dimer has an activity comparable to or improved over natural IL-2.

In some embodiments, as compared to natural IL-2, the polypeptide dimer according to the present disclosure has a half-life increased by 10%, 20%, 30%, 40%, 50%, 60%, 70%, 80%, 90%, 100%, 150%, 200% or more.

In some embodiments, as compared to natural IL-15, the polypeptide dimer according to the present disclosure has a half-life increased by 10%, 20%, 30%, 40%, 50%, 60%, 70%, 80%, 90%, 100%, 150%, 200% or more.

V. Expression of the Fusion Polypeptide and Polypeptide Dimer

To express the fusion polypeptide according to the present disclosure, provided is also a polynucleotide encoding the fusion polypeptide according to the present disclosure.

To express the polypeptide dimer according to the present disclosure, provided is also a polynucleotide encoding the polypeptide dimer according to the present disclosure. In some embodiments, the first polypeptide and second polypeptide are encoded by a single polynucleotide. In some embodiments, the first polypeptide and second polypeptide are encoded by different polynucleotides.

The nucleic acid molecules of all or part of the nucleic acid sequences according to the present disclosure can be isolated by polymerase chain reaction (PCR), using oligonucleotide primers designed and synthesized based on the sequence information contained in the sequences.

The polynucleotides according to the present disclosure can be amplified using cDNA, mRNA or genomic DNA as templates and appropriate oligonucleotide primers according to standard PCR amplification technology. The nucleic acid thus amplified can be cloned into a suitable vector and characterized by DNA sequence analysis.

The polynucleotide according to the present disclosure can be prepared by standard synthesis technology, such as using an automatic DNA synthesizer.

Provided is also a complementary chain of nucleic acid molecule described herein. The nucleic acid molecule complementary to another nucleotide sequence is a molecule sufficiently complementary to the nucleotide sequence, such that it can hybridize with the nucleotide sequence to form a stable double strand. Of course, the polynucleotide according to the present disclosure does not comprise the polynucleotide which only hybridizes only with the poly A sequence (such as 3'-end poly (A) of mRNA) or that hybrids with a section of complementary poly T (or U) residues.

Also provided is a vector comprising the polynucleotide according to the present disclosure, preferably an expression vector. Further provided is a host cell comprising the polynucleotide or carrier (preferably, an expression vector) according to the present disclosure. In some embodiments, the polynucleotide according to the present disclosure is incorporated into the genome of the host cell. In some annotations, the polynucleotide according to the present disclosure is not incorporated into the genome of the host cell.

In some embodiments, the first polypeptide and second polypeptide of the fusion polypeptide according to the present disclosure are express by a single expression vector. In some embodiments, the first polypeptide and second polypeptide of the fusion polypeptide according to the present disclosure are express by different vectors.

The selection of expression vectors is related to the host cell used to express the fusion polypeptide or polypeptide dimer. The host cells which can be used to express the fusion polypeptide according to the present disclosure comprise but not limited to bacteria (including *E. coli.*), yeast, insect cells and mammalian cells, such as COS, CHO, HeLa and 293-6E cells. Expression vectors suitable for various host cells are known in the art. For example, expression vectors suitable for bacteria comprise but not limited to pET vectors (such as pET-28a, pET-30a, pET-32a and pET-40a or the like), pEX vectors (such as pEX-1), pGH112, pUC118 and pEZZ18; expression vectors suitable for yeast comprise but not limited to pESP vectors (such as pESP-1, pESP-2, pESP-3 or the like), pDR196, pHiSi, p53his, pSH47 and pYCP211; expression vectors suitable for insect cells comprise but not limited to pCoBlast, pIEX/Bac-3, pIEXBac-c-EGFP-4, pFastBac1-His-C, pIEXBac-c-EGFP-3, pFastBac1-GST-N and pIEXBac-c-EGFP-2; expression vectors suitable for mammalian cells comprise but not limited to pCMVInt, pGL4.23, pX334, pX458, pBiFC-CC155, pDP4rs, pDC312 and pcDNA.

In some inclusions, the host cell is 293-6E cell. In some annotations, the expression vector is pcDNA3.4.

The precursor polypeptide comprises a signal peptide which facilitates the secretion and/or processing of the expressed polypeptide. Therefore, in some embodiments, the polynucleotide according to the present disclosure further comprises a sequence encoding the signal peptide. In some embodiments, the signal peptide comprises an amino acid sequence of

```
                                    (SEQ ID NO: 18)
            METDTLLLWVLLLWVPGSTG
```

The polynucleotides or vectors according to the present disclosure can be transferred (transfected) into selected host cells with methods known in the art, such as calcium chloride transformation and calcium phosphate treatment for *E. coli*, electroporation, lipid transfection amine treatment or PEI treatment for mammalian cells. The cells transformed by the vectors can be selected according to the antibiotic resistance genes (such as amp, gpt, neo and hyg genes) in the vectors.

After expression, the recombinant fusion protein can be purified according to standard procedures in the field, including ammonium sulfate precipitation, affinity chromatography, column chromatography using ion or hydrophobic resins, gel electrophoresis or the like. A substantially pure composition with a purity of at least about 90 to 95% is preferable, and a purity of 98 to 99% or higher is most preferably used for pharmaceutical purposes.

In order to facilitate purification, the fusion polypeptide according to the present disclosure can also include a tag sequence, including but not limited to His6 tag, FLAG tag, or the like.

In some embodiments, the fusion polypeptide according to the present disclosure comprises an amino acid sequence of one of SEQ ID NO: 12-15. In some embodiments, the fusion polypeptide according to the present disclosure comprises an amino acid sequence which has at least 70%, 80%, 90%, 95%, 96%, 97%, 98% or 99% sequence identity to one of SEQ ID NO: 12-15, wherein the fusion polypeptide comprises the natural CD25 binding site and has an activity comparable to or improved over natural IL-2, such as that of activating the JAK1/JAK3 and STAT3/STAT5 signal pathways.

In some embodiments, the polynucleotide or vector such as expression vector according to the present disclosure encodes an amino acid sequence of SEQ ID NO: 31 and an amino acid sequence of SEQ ID NO: 32. In some embodiments, the polynucleotide or vector such as expression vector according to the present disclosure encodes an amino acid sequence which has at least 70%, 80%, 90%, 95%, 96%, 97%, 98% or 99% sequence identity to SEQ ID NO: 31 and an amino acid sequence which has at least 70%, 80%, 90%, 95%, 96%, 97%, 98% or 99% sequence identity to SEQ ID NO: 32, wherein the expressed first polypeptide comprises the natural CD25 binding site and the polypeptide dimer has an activity comparable to or improved over natural IL-2, such as that of activating the JAK1/JAK3 and STAT3/STAT5 signal pathways.

In some embodiments, the polynucleotide or vector such as expression vector according to the present disclosure encodes an amino acid sequence of SEQ ID NO: 33 and an amino acid sequence of SEQ ID NO: 34. In some embodiments, the polynucleotide or vector such as expression vector according to the present disclosure encodes an amino acid sequence which has at least 70%, 80%, 90%, 95%, 96%, 97%, 98% or 99% sequence identity to SEQ ID NO: 33 and an amino acid sequence which has at least 70%, 80%, 90%, 95%, 96%, 97%, 98% or 99% sequence identity to SEQ ID NO: 34, wherein the expressed first polypeptide comprises the natural CD25 binding site and the polypeptide dimer has an activity comparable to or improved over natural IL-2, such as that of activating the JAK1/JAK3 and STAT3/STAT5 signal pathways.

VI. Pharmaceutical Composition

Provided is a pharmaceutical composition comprising the fusion polypeptide according to the present disclosure. In an embodiment, the pharmaceutical composition comprises the fusion polypeptide according to the present disclosure and at least one pharmaceutically acceptable carrier. The fusion polypeptide according to the present disclosure can be combined with a pharmaceutically acceptable carrier according to known methods to prepare the pharmaceutical composition.

Provided is also a pharmaceutical composition comprising the polypeptide dimer according to the present disclosure. In an embodiment, the pharmaceutical composition comprises the polypeptide dimer according to the present disclosure and at least one pharmaceutically acceptable carrier. The polypeptide dimer according to the present disclosure can be combined with a pharmaceutically acceptable carrier according to known methods to prepare the pharmaceutical composition.

The pharmaceutical acceptable carrier includes but not limited to solvent, emulsifier, buffer, stabilizer or the like. The solvent comprises water, aqueous solution and nonaqueous solvent (such as vegetable oil).

The pharmaceutical composition according to the present disclosure can be applied by any suitable route, including subcutaneous, intramuscular, intraarticular, intravenous, intradermal, intraperitoneal, intranasal, intracranial, parenteral administration. Preferably, the pharmaceutical composition according to the present disclosure is administered intravenously. It should be understood that the administration route may vary with the therapeutic agent, the condition and age of the recipient, and the disease being treated.

The pharmaceutical composition according to the present disclosure may be a solution or a lyophilized preparation.

In some embodiments, the pharmaceutical composition according to the present disclosure is provided in the form of freeze-dried powders for rehydration before administration. The pharmaceutical composition according to the present disclosure may also be provided in a liquid form, which can be directly applied to the patient. In some compositions, the composition is provided in a pre-filled syringe as a liquid.

In some embodiments, the composition according to the present disclosure is encapsulated in liposomes. In some embodiments, liposomes can be coated with flexible water-soluble polymers, which can avoid being taken up by organs of mononuclear phagocytic system, mainly liver and spleen. Hydrophilic polymers suitable for coating liposomes comprises but not limited to, PEG, polyvinylpyrrolidone, polyvinylmethyl ether, polymethyloxazoline, polyethyloxazoline, polyhydroxypropyloxazoline, polyhydroxypropylmethylacrylamide, polymethylacrylamide, polydimethylacrylamide, polyhydroxypropylmethacrylate, polyoxyethylacrylate, hydroxymethylcellulose hydroxyethylamide, hydrophilic polyvinyl alcohol or the like.

The pharmaceutical composition according to the present disclosure can be administered once or multiple times according to the dosage and frequency required and tolerated by the patient. In any case, the applied pharmaceutical composition should provide sufficient protein according to the present disclosure to effectively treat the patient.

VII. Treatment Application

Provided further is a method for treat a disease, such as that related to immunosuppression with the fusion polypeptide according to the present disclosure.

In some embodiments, provided is a method for treating a cancer, comprising administering a subject in need thereof the fusion polypeptide or the pharmaceutical composition according to the present disclosure in an effective amount. The cancer comprises but not limited to lung cancer, liver cancer, kidney cancer, head and neck cancer, colorectal cancer, gastric cancer, nasopharyngeal cancer, glioma, melanoma and osteosarcoma.

In some embodiments, provided is a method for activating an immune cell or improving proliferation of an immune cell, comprising administering a subject in need thereof the fusion polypeptide or the pharmaceutical composition according to the present disclosure in an effective amount. In some embodiments, the immune cell is T cell or NK cell.

In some embodiments, provided is use of the fusion polypeptide or the pharmaceutical composition according to the present disclosure for the manufacture of a medicament for treating a cancer. The cancer comprises but not limited to lung cancer, liver cancer, kidney cancer, head and neck cancer, colorectal cancer, gastric cancer, nasopharyngeal cancer, glioma, melanoma and osteosarcoma.

In some embodiments, provided is use of the fusion polypeptide or the pharmaceutical composition according to the present disclosure for the manufacture of a medicament for activating an immune cell or improving proliferation of an immune cell. In some embodiments, the immune cell is T cell or NK cell.

Provided further is a method for treating a disease, such as that related to immunosuppression with the polypeptide dimer according to the present disclosure.

In some embodiments, provided is a method for treating a cancer, comprising administering a subject in need thereof the polypeptide dimer or the pharmaceutical composition according to the present disclosure in an effective amount. The cancer comprises but not limited to lung cancer, liver cancer, kidney cancer, head and neck cancer, colorectal cancer, gastric cancer, nasopharyngeal cancer, glioma, melanoma and osteosarcoma.

In some embodiments, provided is a method for activating an immune cell or improving proliferation of an immune cell, comprising administering a subject in need thereof the polypeptide dimer or the pharmaceutical composition according to the present disclosure in an effective amount. In some embodiments, the immune cell is T cell or NK cell.

In some embodiments, provided is use of the polypeptide dimer or the pharmaceutical composition according to the present disclosure for the manufacture of a medicament for treating a cancer. The cancer comprises but not limited to lung cancer, liver cancer, kidney cancer, head and neck cancer, colorectal cancer, gastric cancer, nasopharyngeal cancer, glioma, melanoma and osteosarcoma.

In some embodiments, provided is use of the polypeptide dimer or the pharmaceutical composition according to the present disclosure for the manufacture of a medicament for activating an immune cell or improving proliferation of an immune cell. In some embodiments, the immune cell is T cell or NK cell.

Embodiments

P1. A polypeptide dimer, comprising a first polypeptide and a second polypeptide,

- wherein the first polypeptide comprises a first dimerization domain and a polypeptide of interest, wherein the polypeptide of interest is located at the first end of the first dimerization domain,
- wherein the second polypeptide comprises a second dimerization domain and a binding domain, wherein the binding domain is located at the first end of the second dimerization domain,
- wherein the first polypeptide forms a dimer with the second polypeptide through the first dimerization domain and the second dimerization domain, and wherein the first end of the first dimerization domain is adjacent to the first end of the second dimerization domain, the binding domain is capable of binding to the site of interest on the polypeptide of interest.

P2. The polypeptide dimer according to Embodiment P1, wherein the polypeptide of interest is derived from a cytokine of the four α-helical bundle cytokine family, the cytokine comprises four α-helix bundles of, from N-terminal to C-terminal, helical bundle 1 (H1), helical bundle 2 (H2), helical bundle 3 (H3) and helical bundle 4 (H4).

P3. The polypeptide dimer according to Embodiment P2, wherein the polypeptide of interest is a cytokine of the circularly permutated four α-helical bundle cytokine family, comprising four α-helical bundles of, from N-terminal to C-terminal, H2, H3, H4 and H1; H3, H4, H1 and H2; or H4, H1, H2 and H3.

P4. The polypeptide dimer according to Embodiment P3, wherein the amino acid in the circularly permutated cytokine corresponding to N-terminal of the natural cytokine is linked to the amino acid corresponding to C-terminal of the natural cytokine via a linker.

P5. The polypeptide dimer according to Embodiment P4, wherein the linker is a GS linker or a polyglycine linker having a length of 1-10 amino acids.

P6. The polypeptide dimer according to any one of Embodiments P1-P5, wherein the polypeptide of interest is a circularly permutated IL-2 or a circularly permutated IL-15.

P7. The polypeptide dimer according to Embodiment P6, wherein the circularly permutated IL-2 comprises four α-helical bundles of, from N-terminal to C-terminal, H3, H4, H1 and H2, or H4, H1, H2 and H3.

P8. The polypeptide dimer according to Embodiment P7, wherein the circularly permutated IL-2 comprises an amino acid sequence of SEQ ID NO: 21.

P9. The polypeptide dimer according to Embodiment P7 or P8, wherein the site of interest is a CD25 binding site, the binding domain is an extracellular domain of CD25.

P10. The polypeptide dimer according to Embodiment P6, wherein the circularly permutated IL-15 comprises four α-helical bundles of, from N-terminal to C-terminal, H3, H4, H1 and H2.

P11. The polypeptide dimer according to Embodiment P10, wherein the circularly permutated IL-15 comprises an amino acid sequence of SEQ ID NO: 4.

P12. The polypeptide dimer according to Embodiment P10 or P11, wherein the site of interest is a CD215 binding site, the binding domain is an extracellular domain of CD215.

P13. The polypeptide dimer according to any one of Embodiments P1-P12, wherein the first and second dimerization domains comprise heavy chain constant region CH2 and CH3 of immunoglobulin (Ig).

P14. The polypeptide dimer according to Embodiment P13, wherein the Ig is human Ig.

P15. The polypeptide dimer according to Embodiment P14, wherein the Ig is human IgG1.

P16. The polypeptide dimer according to any one of Embodiments P1-P15, wherein the first dimerization domain forms Fc region of the human IgG1 with the second dimerization domain.

P17. The polypeptide dimer according to any one of Embodiments P1-P16, wherein the first dimerization domain comprises an amino acid sequence of SEQ ID NO: 21, and the second dimerization domain comprises an amino acid sequence of SEQ ID NO: 22; or the first dimerization domain comprises an amino acid sequence of SEQ ID NO: 22, and the second dimerization domain comprises an amino acid sequence of SEQ ID NO: 21.

P18. The polypeptide dimer according to any one of Embodiments P13-P17, wherein the first end of the first dimerization domain is C-terminal, and the first end of the second dimerization domain is C-terminal.

P19. A polypeptide dimer, comprising a first polypeptide and a second polypeptide,

- wherein the first polypeptide comprises a first chain of the Fc region of the human IgG1 and a circularly permutated IL-2, the circularly permutated IL-2 is linked to C-terminal of the first chain of the Fc region of the human IgG1,
- wherein the second polypeptide comprises a second chain of the Fc region of the human IgG1 and a CD25 extracellular domain, the CD25 extracellular domain is linked to C-terminal of the second chain of the Fc region of the human IgG1, and
- wherein the circularly permutated IL-2 comprises four α-helical bundles of, from N-terminal to C-terminal, H3, H4, H1 and H2; or H4, H1, H2 and H3.

P20. The polypeptide dimer according to Embodiment P19, wherein the circularly permutated IL-2 comprises an amino acid sequence of SEQ ID NO: 2.

P21. A polypeptide dimer, comprising a first polypeptide and a second polypeptide,

- wherein the first polypeptide comprises a first chain of the Fc region of the human IgG1 and a circularly permutated IL-15, the circularly permutated IL-15 is linked to C-terminal of the first chain of the Fc region of the human IgG1,
- wherein the second polypeptide comprises a second chain of the Fc region of the human IgG1 and a CD215 extracellular domain, the CD215 extracellular domain is linked to C-terminal of the second chain of the Fc region of the human IgG1, and
- wherein the circularly permutated IL-15 comprises four α-helical bundles of, from N-terminal to C-terminal, H3, H4, H1 and H2.

P22. The polypeptide dimer according to Embodiment P21, wherein the circularly permutated IL-15 comprises an amino acid sequence of SEQ ID NO: 22.

P23. The polypeptide dimer according to any one of Embodiments P19-P22, wherein the first chain comprises an amino acid sequence of SEQ ID NO: 23 and the second chain comprises an amino acid sequence of SEQ ID NO: 24; or the first chain comprises an amino acid sequence of SEQ ID NO: 24 and the second chain comprises an amino acid sequence of SEQ ID NO: 23.

P24. A pharmaceutical composition, comprising the polypeptide dimer according to any one of Embodiments P1-P23.

P25. Use of the polypeptide dimer according to any one of Embodiments P1-P23 for the manufacture of a medicament for treating a cancer.

P26. Use of the polypeptide dimer according to any one of Embodiments P1-P23 for the manufacture of a medicament for activating an immune cell or improving proliferation of an immune cell.

P27. The use according to Embodiment P26, wherein the immune cell is T cell or NK cell.

P28. One or more isolated polynucleotides, encoding the polypeptide dimer according to any one of Embodiments P1-P23.

P29. One or more expression vectors, comprising the polynucleotide according to Embodiment P28.

P30. A host cell, comprising the polynucleotide according to Embodiment P28 or the vector according to Embodiment P29.

Examples

Through the following examples, those skilled in the art will have a better understanding of the present disclosure. It should be understood that the examples are provided only for illustration rather than limitation to the scope of the present disclosure. Unless otherwise specified, the experimental methods used herein are conventional methods, and the specific procedures of gene cloning can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989).

Example 1 Construction of Expression Vector

The construction of expression vector was completed by Nanjing GenScript Biotech Corp., including synthesis of nucleic acid encoding amino acid sequences of SEQ ID NO: 12-15 and 31-34, additionally containing the nucleotide sequence encoding signal peptide of SEQ ID NO: 18; construction of the nucleic acid into the mammalian cell expression vector pcDNA 3.4 by molecular cloning method, and amplification and purification of the plasmids.

Example 2 Expression of Fusion Polypeptide and Polypeptide Dimer

In this Example, 293-6E cells were transfected with nucleic acid encoding fusion polypeptide for eukaryotic expression. The expression and purification of fusion polypeptide was completed by Nanjing GenScript Biotech Corp. The procedures were as follows:

293-6E cells were cultured in serum free FreeStyle™ 293 Expression medium (Thermo Fisher Scientific, Inc., Carlsbad, CA, USA) in Erlenmeyer conical flask (Corning Inc., Acton, MA), where the culture was performed on vibrating incubator (VWR® Scientific, Chester, PA) at 37° C. and 5% $CO_2$.

The cells were diluted to the proper density one day prior to transfection.

On the day of transfection, the plasmid mixture (the mass ratio of the plasmid encoding the first polypeptide and that encoding the second polypeptide was 1:1) and the transfection reagents (such as Polyetherimide, PEI) were mixed in a suitable ratio (such as 1:3 mass ratio) in the culture medium, and then added into the cell culture medium for transfection for secretion and expression of the target protein.

After six days, the cell survival rate was about 50%-80%. The supernatant was obtained by centrifugation, which contained the target protein (the expressed polypeptide did not contain the signal peptide).

After filtration with 0.22 μm membrane, the supernatant was loaded into HisTrap™ FF Crude 5 ml (GE, catalog No. 17-5286-01) chromatographic column at a rate of 3 ml/min. After washing and elution, the purified protein was collected and stored in phosphate buffer solution (PBS pH 7.2) through buffer exchange.

The molecular weight, purity and sequence coverage of the purified protein were evaluated by SDS-PAGE, Western blot (results not shown), high performance liquid chromatography with molecular sieve (SEC-HPLC) and liquid chromatography mass spectrometry (LC-MS). The primary antibody used in immunoblotting was mouse anti-His tag antibody (GenScript, catalog No. A00186) or mouse anti-FLAG antibody (GENSCRIPT, catalog No. A00187), the secondary antibody was horseradish peroxidase modified goat anti mouse IgG antibody (GENSCRIPT, catalog No. A00160).

Figure 4:
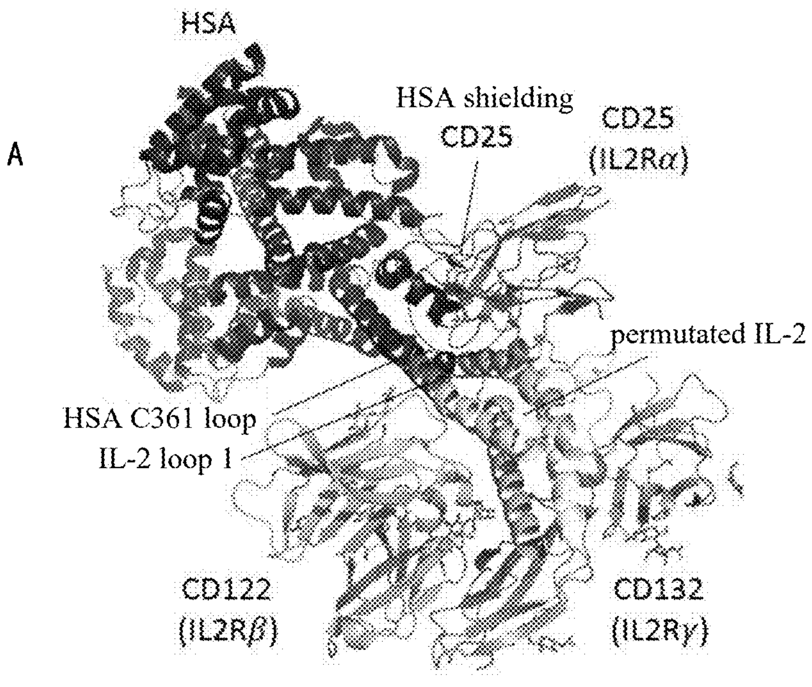
FIG. 4-7 shows the expression of fusion polypeptide according to the present disclosure and the structural model of HSA shielding the CD25 binding site on IL-2.
Figure 4:
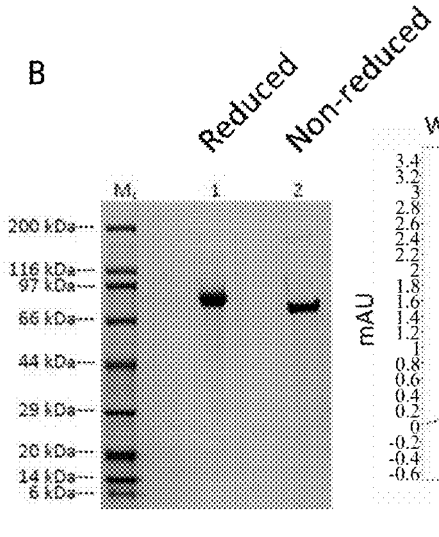
Figure 4:
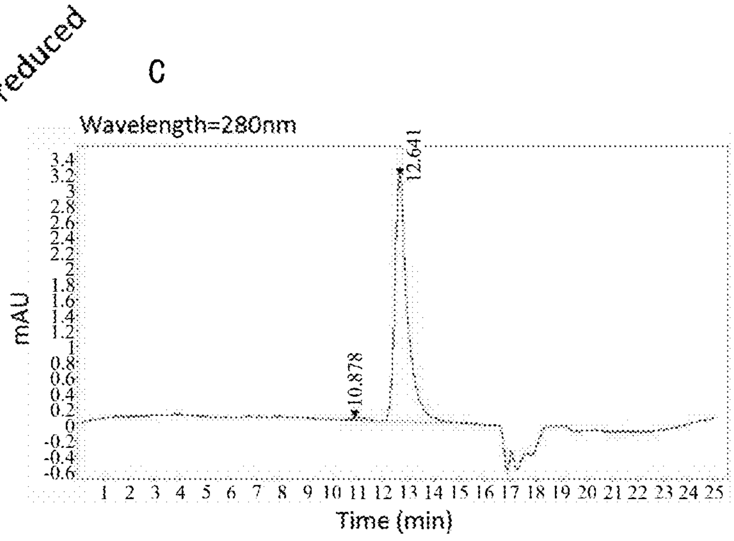
Figure 5:
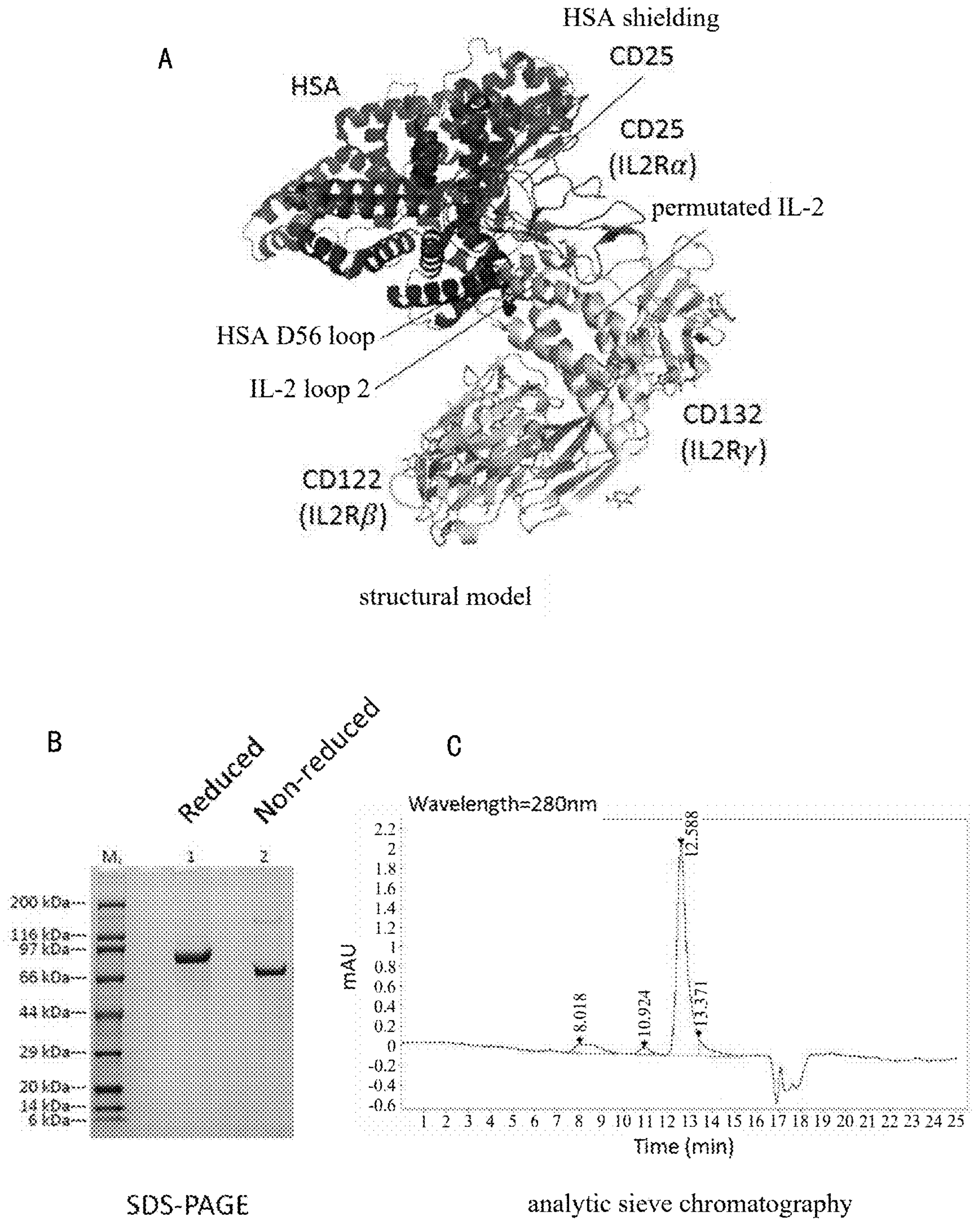
Figure 6:
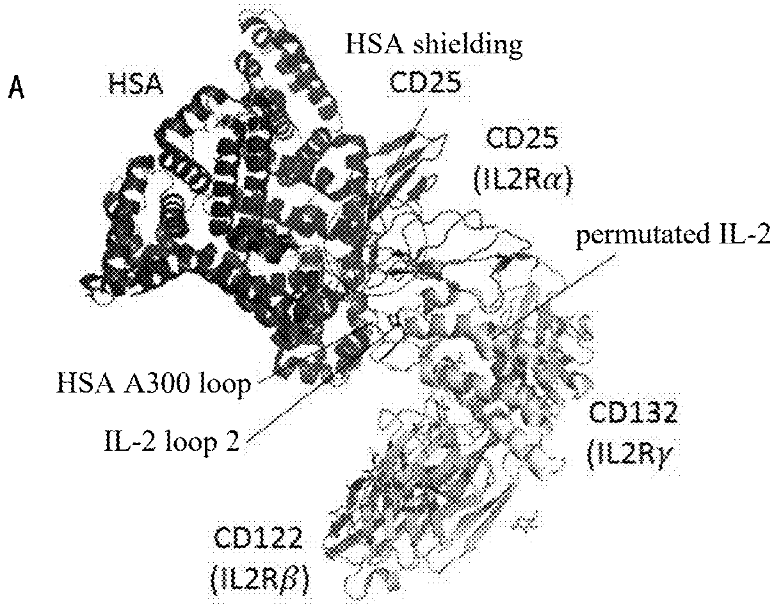
Figure 6:
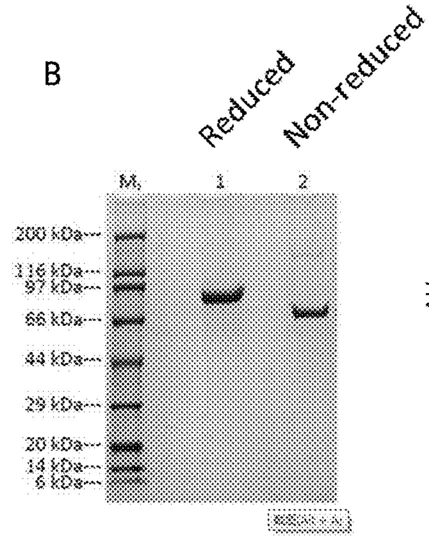
Figure 6:
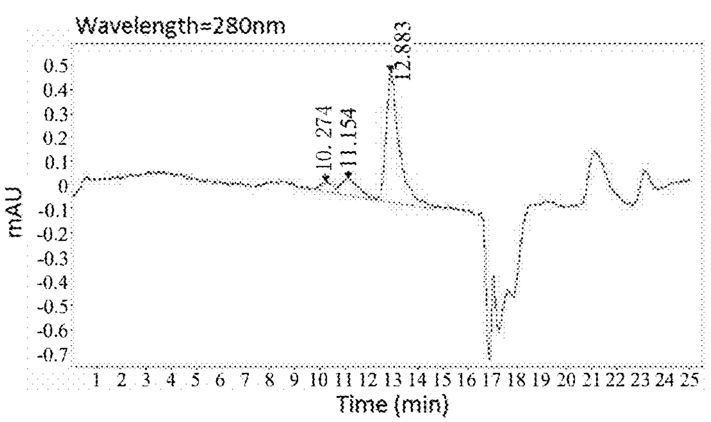
Figure 7:
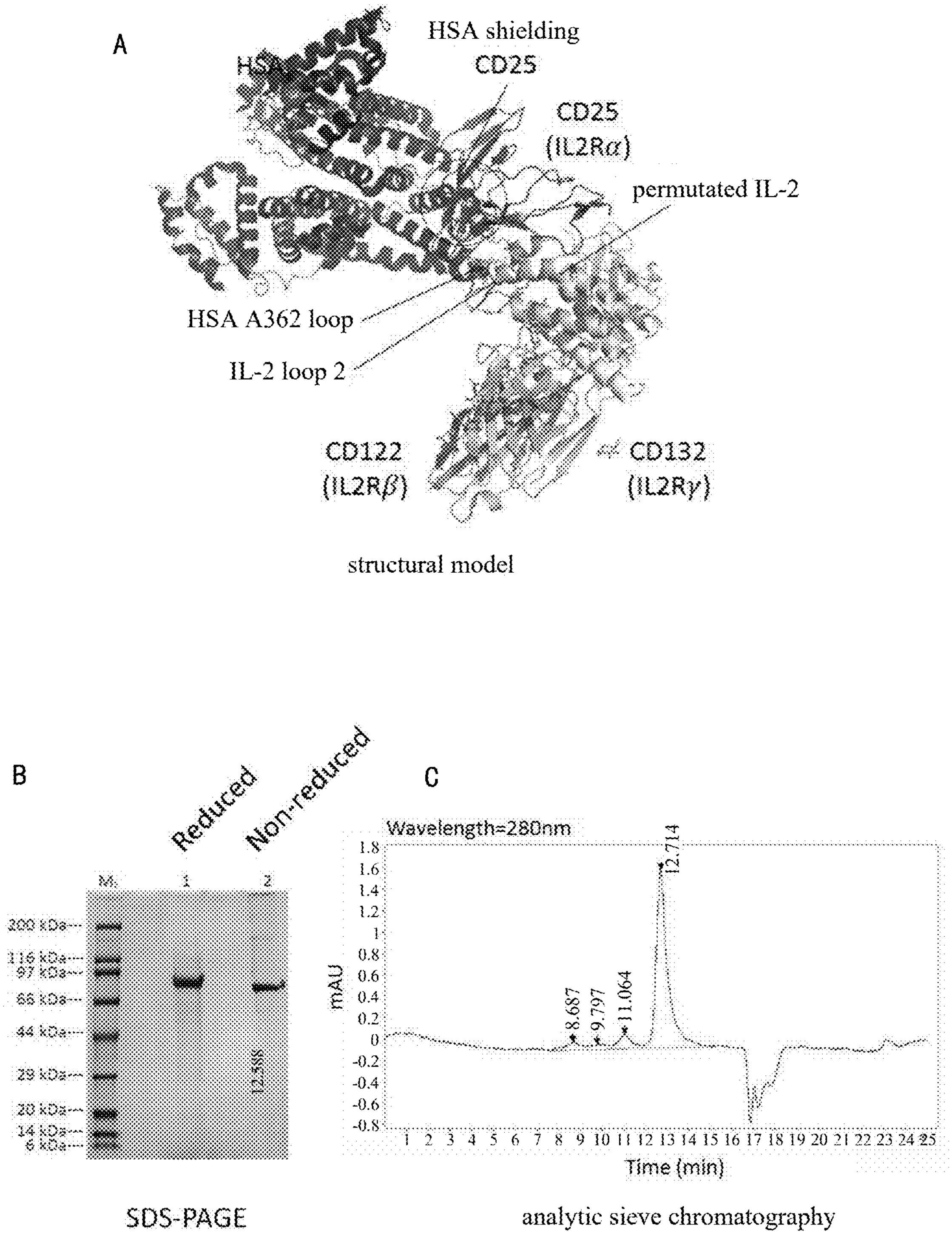
Figure 8:
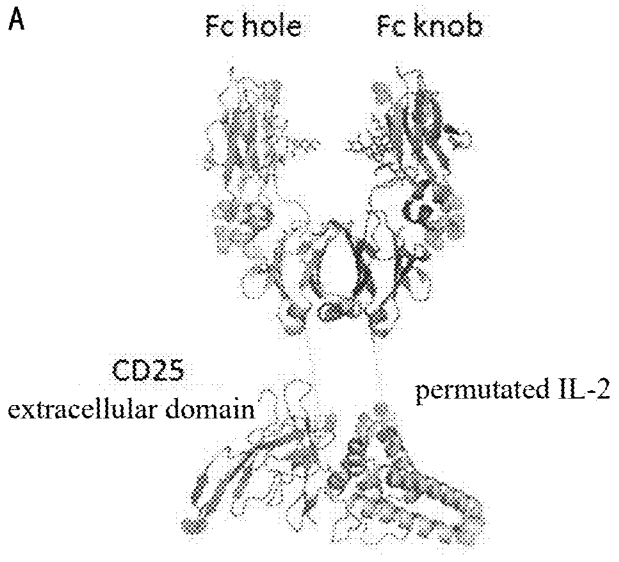
FIG. 8 and FIG. 9 show the structural model of the polypeptide dimer according to the present disclosure and its expression, and the amino acid sequence of the circularly permutated IL-2 is as shown in SEQ ID NO: 21.
Figure 8:
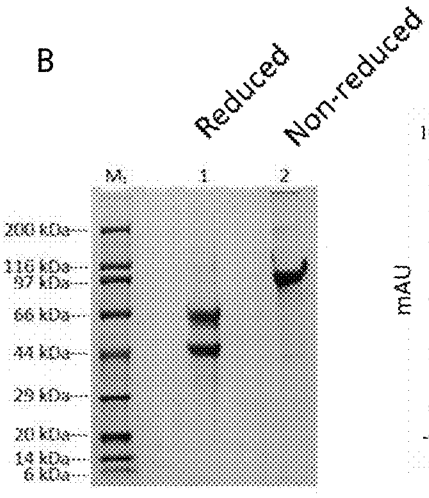
Figure 8:
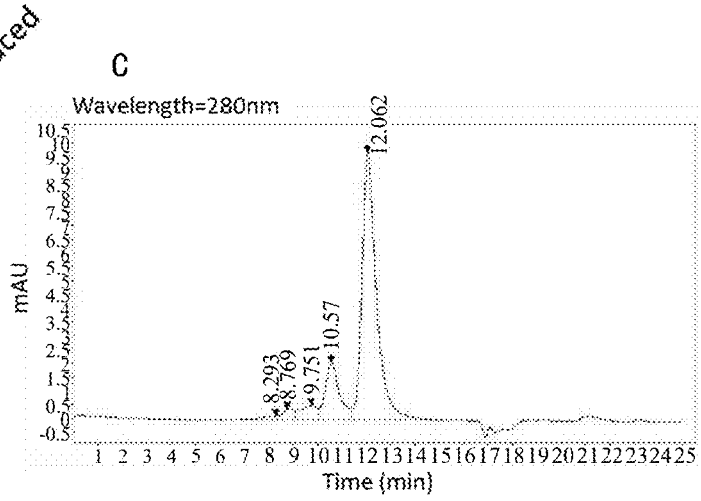
Figure 9:
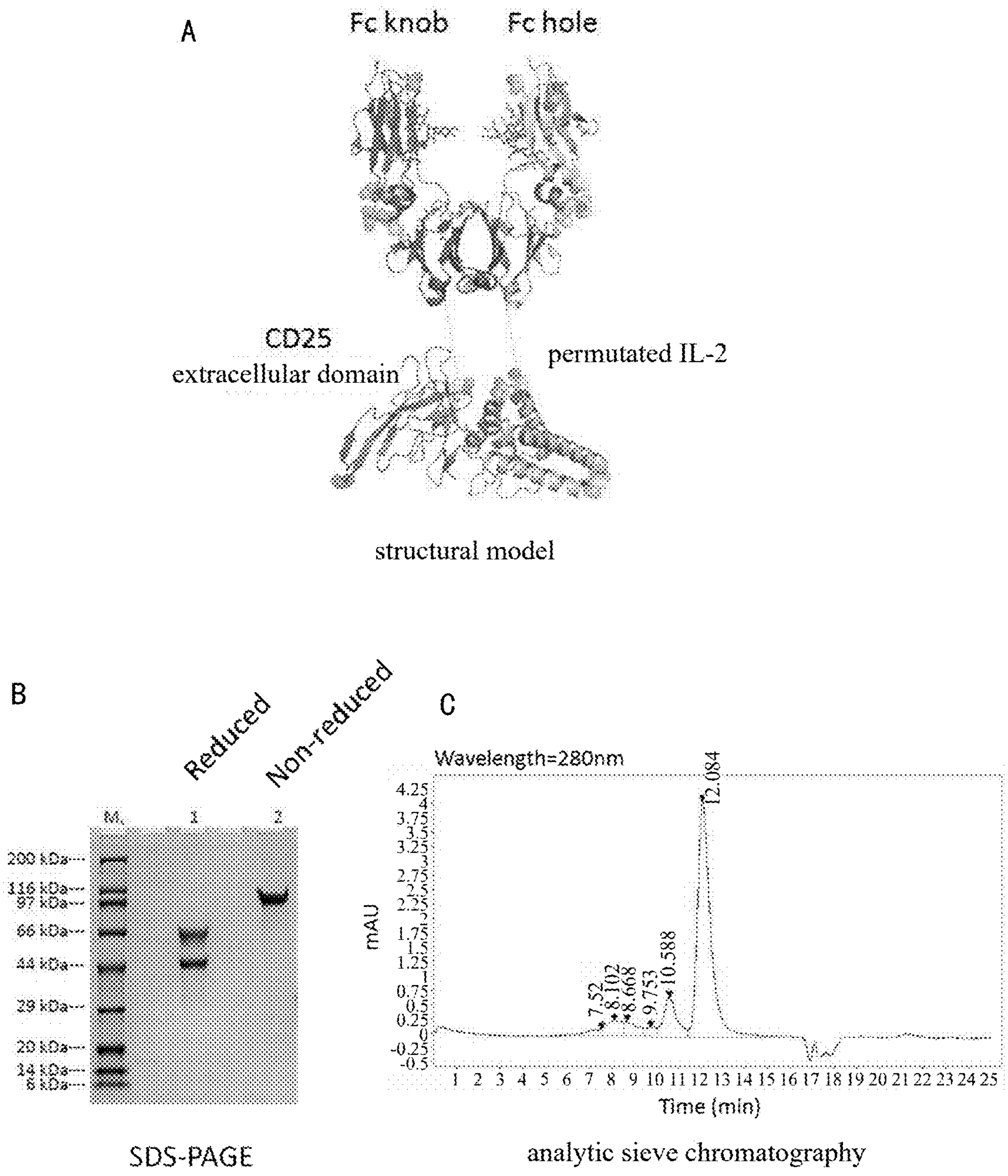

The results were shown in FIG. 4-9. FIG. 4: loop 1 of IL-2 was opened to form circularly permutated IL-2, and the insertion site was at C361 of HSA (SEQ ID NO: 12). FIG. 5: loop 2 of IL-2 was opened to form circularly permutated IL-2, and the insertion site was at D56 of HSA (SEQ ID NO: 13). FIG. 6: loop 2 of IL-2 was opened to form circularly permutated IL-2, and the insertion site was at A300 of HSA (SEQ ID NO: 14). FIG. 7: loop 1 of IL-2 was opened to form circularly permutated IL-2, and the insertion site was in A362 of HSA (SEQ ID NO: 15). FIG. 8: circularly permutated IL-2 was fused with knob chain of knob-in-hole modified human IgG1 Fc region (SEQ ID NO: 31), extracellular domain of CD25 was fused with hole chain of knob-in-hole modified human IgG1 Fc region (SEQ ID NO: 32). FIG. 9: circularly permutated IL-2 was fused with hole chain of knob-in-hole modified human IgG1 Fc region (SEQ ID NO: 33), extracellular domain of CD25 was fused with knob chain of knob-in-hole modified human IgG1 Fc region (SEQ ID NO: 34). In FIG. In 4-7, panel A showed the structural model of CD25 binding site of IL-2 shielded by HSA, panel B showed the SDS-PAGE results of reduced and non-reduced fusion polypeptides, and panel C showed the molecular sieve analysis results. In FIG. In 8 and 9, panel A showed the structural model of the polypeptide dimer according to the present disclosure, panel B showed the SDS-PAGE results of reduced and non-reduced polypeptide dimers, and panel C showed the molecular sieve analysis results.

As shown in Fig As shown in 4-7, four fusion polypeptides achieved high expression levels. SDS-PAGE and SEC-HPLC showed high purity and high homogeneity. High sequence coverage was detected by LC-MS, confirming the integrity and correctness of the purified fusion polypeptides.

As shown in FIGS. 8 and 9, both polypeptide dimers achieved high expression levels. SDS-PAGE and SEC-HPLC showed high purity and high homogeneity. High sequence coverage was detected by LC-MS, confirming the integrity and correctness of the purified dimers.

Example 3 Detection of Activities of Fusion Polypeptide and Polypeptide Dimer

In this example, HEK-Blue™ IL-2 cell line (INVIVOGEN) was used to detect the activity of these fusion proteins in activating downstream signal pathways at the cell level.

The HEK-Blue™ IL-2 cell line was constructed by stable transfection of the genes encoding the molecules required for IL-2 signal pathways in human embryonic kidney 293 cells (HEK-293), the molecules including CD25, CD122 and CD132 receptor molecules, human JAK3 kinase and transcription factor STAT5, together with the secretory embryonic alkaline phosphatase (SEAP) reporter gene regulated by STAT5. When the cell line was stimulated by IL-2, it will activate the downstream signal pathways to activate STAT5 and upregulate the secretion and expression of SEAP.

The above detection was completed by Nanjing Topoxin Biotechnology Co., Ltd. The procedures were as follows:

1. Experiment Preparation 1.1. Preparation of QUANTI Blue solution: QB reagent and QB buffer were thawed at room temperature, to which was added 98 mL of sterile water, after blending, the mixture was divided into 10 mL/tube, and stored in dark at −20° C.

1.2. Inactivation of serum: 45 mL of serum (FBS) was placed into a 50 mL centrifuge tube, with heat inactivation in 56° C. water bath for 30 min (mixing every 10 min), and was stored at 4° C. for further use.

1.3. Culture medium

Growth medium: DMEM+10% FBS+1% PS+100 μg/mL Normocin+1 μg/ml puromycin+1×HEK-Blue™ CLR Selection; Testing medium: DMEM+10% FBS (Inactivated)+1% PS+100 μg/mL Normocin; Frozen medium: DMEM+20% FBS+10% DMSO.

2. Cell Culture, Passage and Preservation 2.1. The cells were placed in the growth medium, and cultured with passage in an incubator at 37° C., 5% $CO_2$;

2.2. When the cell confluence reached 70-80% and the cells were under good condition, the supernatant was discarded and the growth medium preheated in 37° C. water bath was used to resuspend the cells. After cell counting, 200×g centrifugation was conducted for 5 min, and the supernatant was discarded. The cells was suspended with 4° C. precooled frozen medium, and the cell density was adjusted to 5-7×$10^6$ cells/mL, 1 mL per tube. The tubes were put into the programing cooling box, and stored overnight at −80° C. with liquid nitrogen for long-term storage.

3. Verification with HEK-Blue IL-2 System 3.1. Preparation of HEK-Blue IL-2 cell suspension: the cells were rinsed gently twice with preheated DPBS and resuspended with preheated DPBS to form a single cell suspension. After cell counting, 200×g centrifugation was conducted for 5 min. The cells were suspended with preheated testing medium, with the cell density of 2.8×$10^5$ cells/mL.

3.2. Samples of protein (positive control, human IL-2 ACROBIOSYSTEMS, catalog No. IL2-H4113) and HSA (negative control) or human IgG1 Fc segment (negative control, ACROBIOSYSTEMS, catalog No. FCC-H5214) were prepared with serial gradient dilution as follows: initial concentration 650 μM, 5-fold dilution, 8 gradients.

3.3. 20 μL of sample of serial gradient dilution and 180 μL of cell suspension were added to each well of the culture plate (three replicates for each sample), the plate was cultured in incubator at 37° C., 5% $CO_2$ for 20-24 h.

3.4. Supernatant of each culture was added into 96-well plate at 20 μL/well, and the QUANTI-Blue solution thawed and recovered to room temperature was added at 180 μL/well, at 37° C., with incubation for 1-3 h. read with A microplate reader was used to read the absorbance at OD 620-655 nm, and analyze the data.

4. Detection of Fusion Polypeptide Activity

The procedures in step 3 were employed to detect the activity of fusion polypeptide and polypeptide dimer prepared in Example 2, wherein each fusion polypeptide was also prepared into a series of gradient dilution samples according to the procedures in step 3.2.

Figure 10:
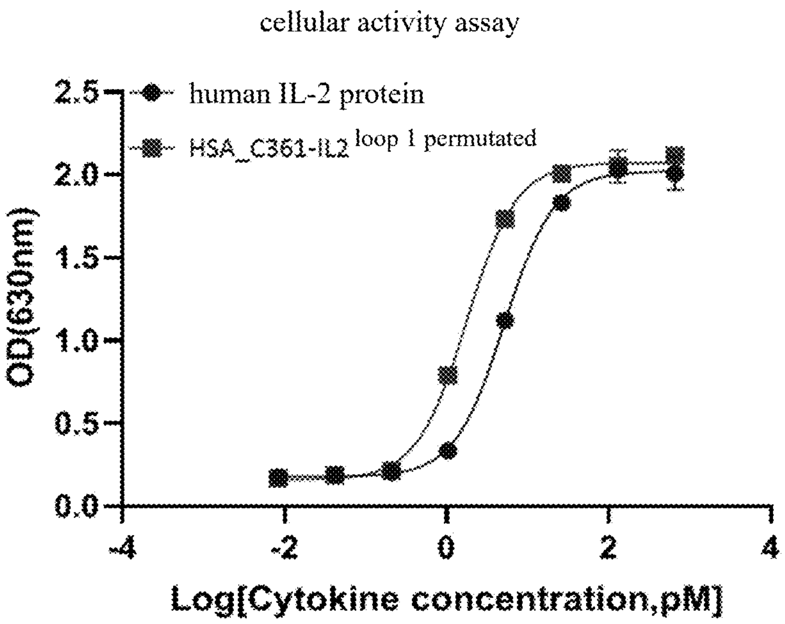
FIG. 10-FIG. 13 show the in vitro activity assay of the fusion polypeptide according to the present disclosure.
Figure 11:
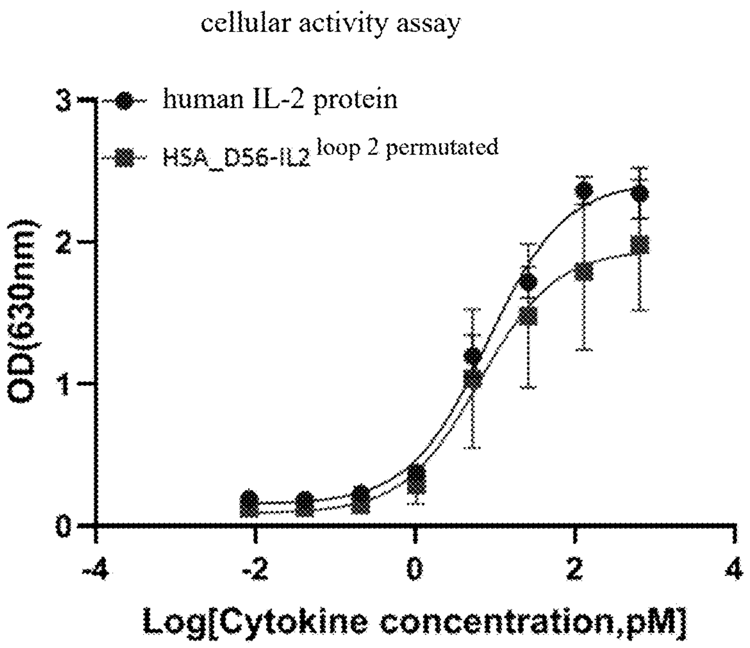
Figure 12:
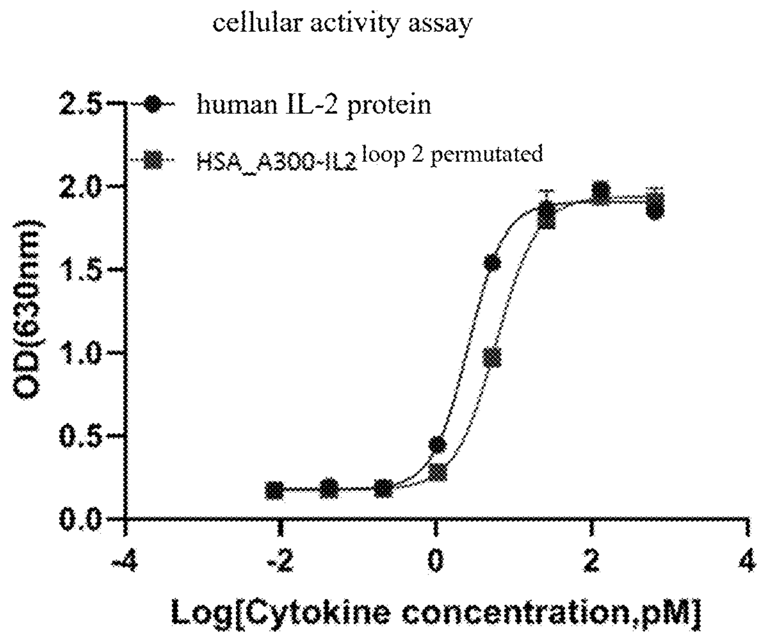
Figure 13:
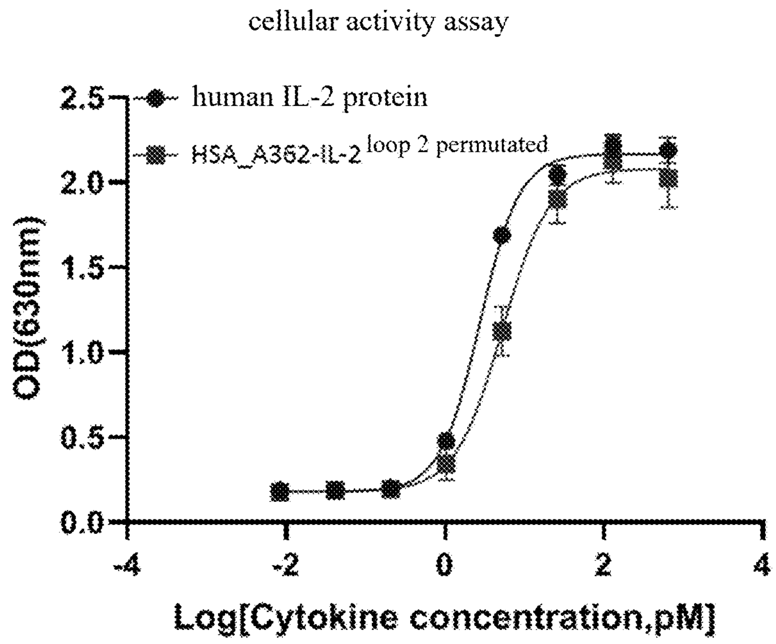
Figure 14:
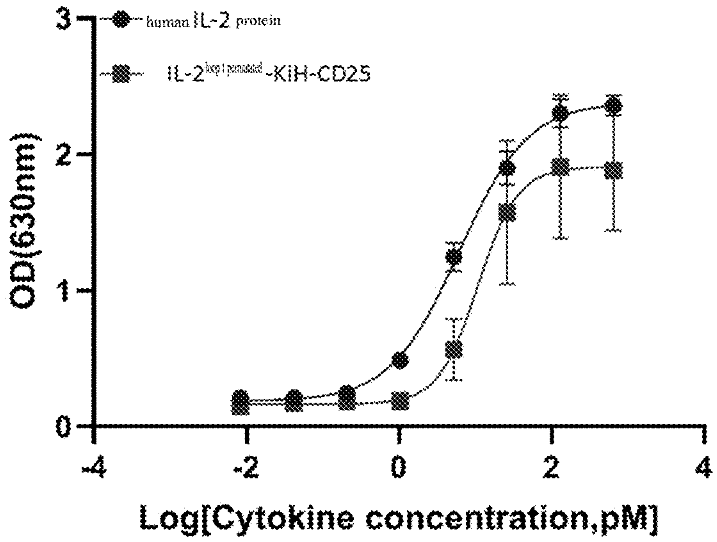
FIG. 14 and FIG. 15 show the in vitro activity assay results of the polypeptide dimer according to the present disclosure, and the amino acid sequence of the circularly permutated IL-2 is as shown in SEQ ID NO: 21.
Figure 15:
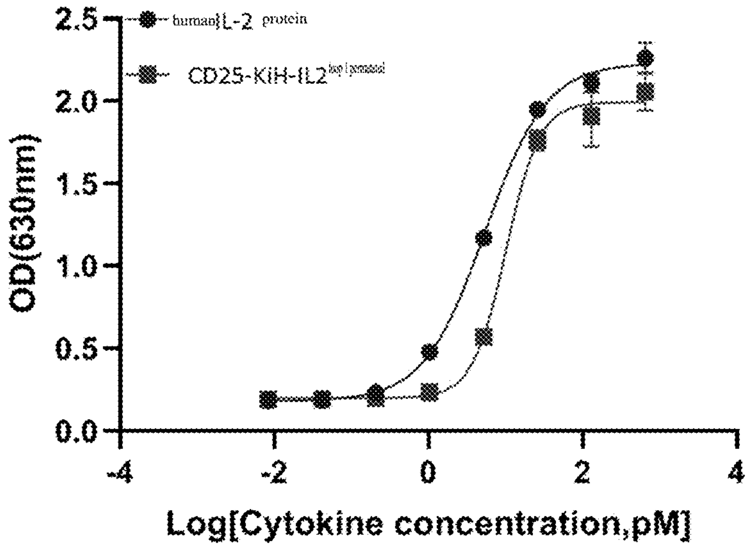

The results were shown in FIG. 10-15. FIG. 10: loop 1 of IL-2 was opened to form circularly permutated IL-2, and the insertion site was at C361 of HSA (SEQ ID NO: 12). FIG. 11: loop 2 of IL-2 was opened to form circularly permutated IL-2, and the insertion site was at D56 of HSA (SEQ ID NO: 13). FIG. 12: loop 2 of IL-2 was opened to form circularly permutated IL-2, and the insertion site was at A300 of HSA (SEQ ID NO: 14). FIG. 13: loop 1 of IL-2 was opened to form circularly permutated IL-2, and the insertion site was in A362 of HSA (SEQ ID NO: 15). FIG. 14: the first polypeptide comprised circularly permutated IL-2, which was fused with knob chain of knob-in-hole modified human IgG1 Fc region (SEQ ID NO: 31), the second polypeptide comprised extracellular domain of CD25, which was fused with hole chain of knob-in-hole modified human IgG1 Fc region (SEQ ID NO: 32). FIG. 15: the first polypeptide comprised circularly permutated IL-2, which was fused with hole chain of knob-in-hole modified human IgG1 Fc region (SEQ ID NO: 33), the second polypeptide comprised extracellular domain of CD25, which was fused with knob chain of knob-in-hole modified human IgG1 Fc region (SEQ ID NO: 34).

The comparisons between the concentration for 50% of maximal effect (EC50) of each fusion polypeptides as detected and EC50 of human IL-2 were shown in Tables 1-6 below.

TABLE 1

| Comparison between fusion polypeptide of SEQ ID NO: 12 and human IL-2 | | |
|---|---|---|
| | Human IL-2 | Fusion polypeptide of SEQ ID NO: 12 |
| EC50 (pM) | 5.123 | 1.750 |

TABLE 2

| Comparison between fusion polypeptide of SEQ ID NO: 13 and human IL-2 | | |
|---|---|---|
| | Human IL-2 | Fusion polypeptide of SEQ ID NO: 13 |
| EC50 (pM) | 7.934 | 6.356 |

TABLE 3

| Comparison between fusion polypeptide of SEQ ID NO: 14 and human IL-2 | | |
|---|---|---|
| | Human IL-2 | Fusion polypeptide of SEQ ID NO: 14 |
| EC50 (pM) | 2.583 | 5.859 |

TABLE 4

| Comparison between fusion polypeptide of SEQ ID NO: 15 and human IL-2 | | |
|---|---|---|
| | Human IL-2 | Fusion polypeptide of SEQ ID NO: 15 |
| EC50 (pM) | 2.755 | 5.253 |

TABLE 5

| Comparison between polypeptide dimer 1 (SEQ ID NO: 31+ SEQ ID NO: 32) and human IL-2 | | |
|---|---|---|
| | Human IL-2 | Polypeptide dimer 1 |
| EC50 (pM) | 6.117 | 10.83 |

TABLE 6

| Comparison between polypeptide dimer 2 (SEQ ID NO: 33 + SEQ ID NO: 34) and human IL-2 | | |
|---|---|---|
| | Human IL-2 | Polypeptide dimer 2 |
| EC50 (pM) | 5.406 | 10.17 |

The results showed that the fusion polypeptide according to the present disclosure showed an activity comparable to or improved over wildtype IL-2, while the HSA or Fc region fragment did not show the corresponding response (results not shown).

Example 4 Detection of Interaction Between Fusion Polypeptides and IL-2 Receptor The interaction between the fusion polypeptide or the polypeptide dimer according to the present disorder and IL-2 receptor was measured using a high-throughput molecular interaction instrument based on the principle of surface plasmon resonance imaging (SPRi).

1. The following receptor proteins or combinations of receptor proteins were immobilized on the surface of carboxyl chip:

CD25;

CD122;

CD25+CD122;

CD122+CD132; and

CD25+CD122+CD132.

2. The wildtype IL-2 protein solutions at gradient concentration were used as the mobile phase, and the SPRi interaction experiment was conducted according to the manufacturer's instructions to measure the binding signal and affinity.

3. The fusion polypeptide or the polypeptide dimer solutions according to the present disclosure prepared following the results of step 2 at gradient concentrations were used as the mobile phase, and the SPRi interaction experiment was conducted according to the manufacturer's instructions to measure the binding signal and affinity.

Example 5 Detection of In Vivo Activity of Fusion Polypeptide

Activities of five selected fusion polypeptide or polypeptide dimer molecules were measured (see Table 7 below) in B16F10 melanoma mouse model for activating the immune system to kill tumors, and the infiltration of CD8+ T cells in tumor tissue was observed. The experiments were entrusted to Jiangsu Jichu Biotechnology Co., Ltd.

TABLE 7

| Code of molecule | Name of molecule | SEQ ID NO: |
|---|---|---|
| ZJ-1 | IL-$2^{loop1\ permutated}$-KiH-CD25 | 31 + 32 |
| ZJ-2 | HSA C361-IL$2^{loop1\ permutated}$ | 12 |
| ZJ-6 | HSA D56-IL $2^{loop2\ permutated}$ | 13 |
| ZJ-12 | HSA A300-IL $2^{loop2\ permutated}$ | 14 |
| ZJ-15 | HSA A362-IL-$2^{loop2\ permutated}$ | 15 |

5.1. Determination of Anti-Tumor Activity in In Vivo Model

B16F10 melanoma cells were cultured in DMEM (Dulbecco's Modified Eagle's Medium) medium+10% (v/v) fetal bovine serum (FBS).

C57BL/6 mice were fed adaptively for a week, B16F10 melanoma cells ($1\times10^6$/animal) were injected subcutaneously, and the mice were kept for 7 days to allow the tumor to grow. The mice with tumors were divided into six groups (9 mice in each group) and injected with the fusion polypeptide or polypeptide dimer molecules and blank control (PBS), respectively in the tail vein. The injection amounts of the fusion polypeptide or polypeptide dimer molecules was 2 mg/kg body weight, with injection once every nine days, three times in total (DO, D9 and D18). The body weight and tumor size (length and width) of each mouse were measured every three days to calculate the tumor volume. The survived mice were sacrificed 27 days after the first injection, and the tumors were taken for photos and embedded in wax for pathological sections for subsequent immunohistochemical experiments.

5.2. Immunohistochemical Detection of CD8 Expression in Tumor Sections a). The slices were subjected to dewaxing and hydration; xylene treatment for 3 times, 5 min each time; anhydrous ethanol treatment for 2 times, 5 min each time; 95% ethanol treatment for 2 times, 5 min each time; distilled water treatment for 2 times, 5 min each time.

b). After thermal remediation with citric acid antigen remediation method, the samples were cooled to room temperature, and washed with PBS for 3 times, 5 min each time.

c). The immunostaining blocking solution was used for blocking at room temperature for 15 min, and then the blocking solution was removed without washing. The anti-CD 8 primary antibody (dilution ratio: 1:2000) was added for incubation at room temperature for 1 h.

d). The samples were washed with PBS for three times, 5 min each time; and incubated with secondary antibody for 1 h.

e). The samples were washed with PBS for three times, 5 min each time; and developed with DAB, and the end point of development was determined by microscopic observation.

f). After development, hematoxylin was used for restaining for 2 min, and tap water was used for returning blue. The samples were subjected to dehydration with ethanol of gradient concentration, made transparent with xylene, and sealed with neutral gum.

g). Image ProPlus software was used to conduct semi-quantitative analysis on immunohistochemical staining results:

Average optical density (IOD/area)=cumulative optical density value/measured area of dyed area.

The higher the average optical density, the stronger the positive.

5.3. Experimental Results

Figure 16:
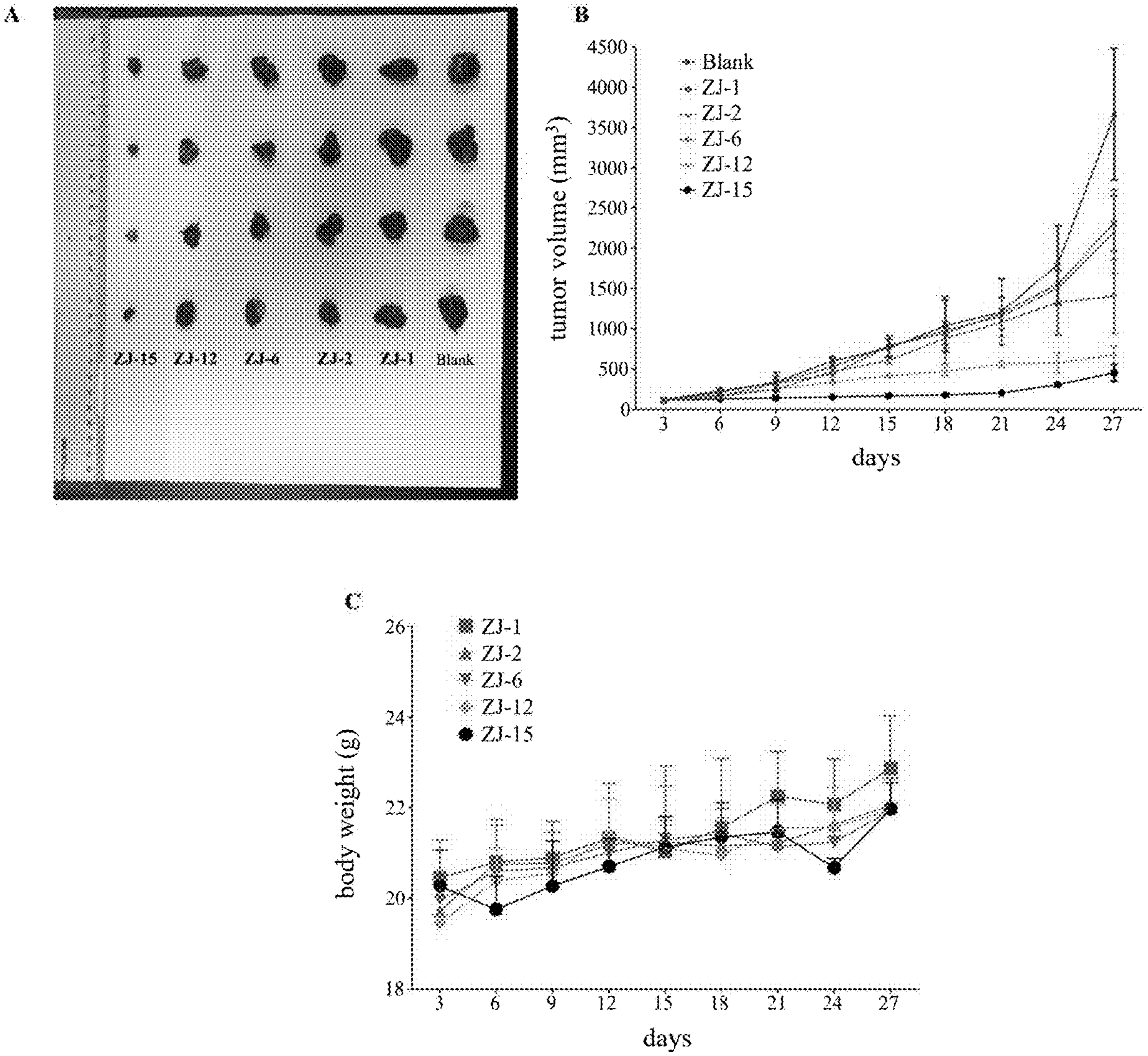
FIG. 16 shows the experimental results of injecting the fusion polypeptide or polypeptide dimer according to the present disclosure into tumor-bearing mice; A: tumor, 27 days after the first injection; B: curve for the tumor volume over time; and C: curve for mice body weight over time.

As shown in FIGS. 16A and B, at the dose of 2 mg/kg, in all of the selected five fusion polypeptide or polypeptide dimer showed anti-tumor activities in mouse melanoma models, among which ZJ-15 showed the strongest activity, and nearly no tumor growth. Compared with the data reported in the prior art (Charych et al., Clin Canc Res 2016), the fusion polypeptide or polypeptide dimer molecules according to the present disclosure (especially, ZJ-15 and ZJ-12) showed significantly superior antitumor activity in vivo over wildtype IL-2 with the same animal tumor model, dose, administration mode and frequency.

As shown in FIG. 16C, when the fusion polypeptide or polypeptide dimer molecule according to the present disclosure were administered to mice at a dose of 2 mg/kg (relatively high for cytokine), the body weights of mice still steadily increased. Such results showed that the fusion polypeptide or polypeptide dimer molecules according to the present disclosure had good tolerance potential in vivo, proving the safety of the fusion polypeptide or polypeptide dimer molecules according to the present disclosure.

The expression of CD8 was observed by immunohistochemical staining of tumor tissue sections to detect the infiltration of CD8+ T cells (killing T cells) in tumors.

Figure 17:
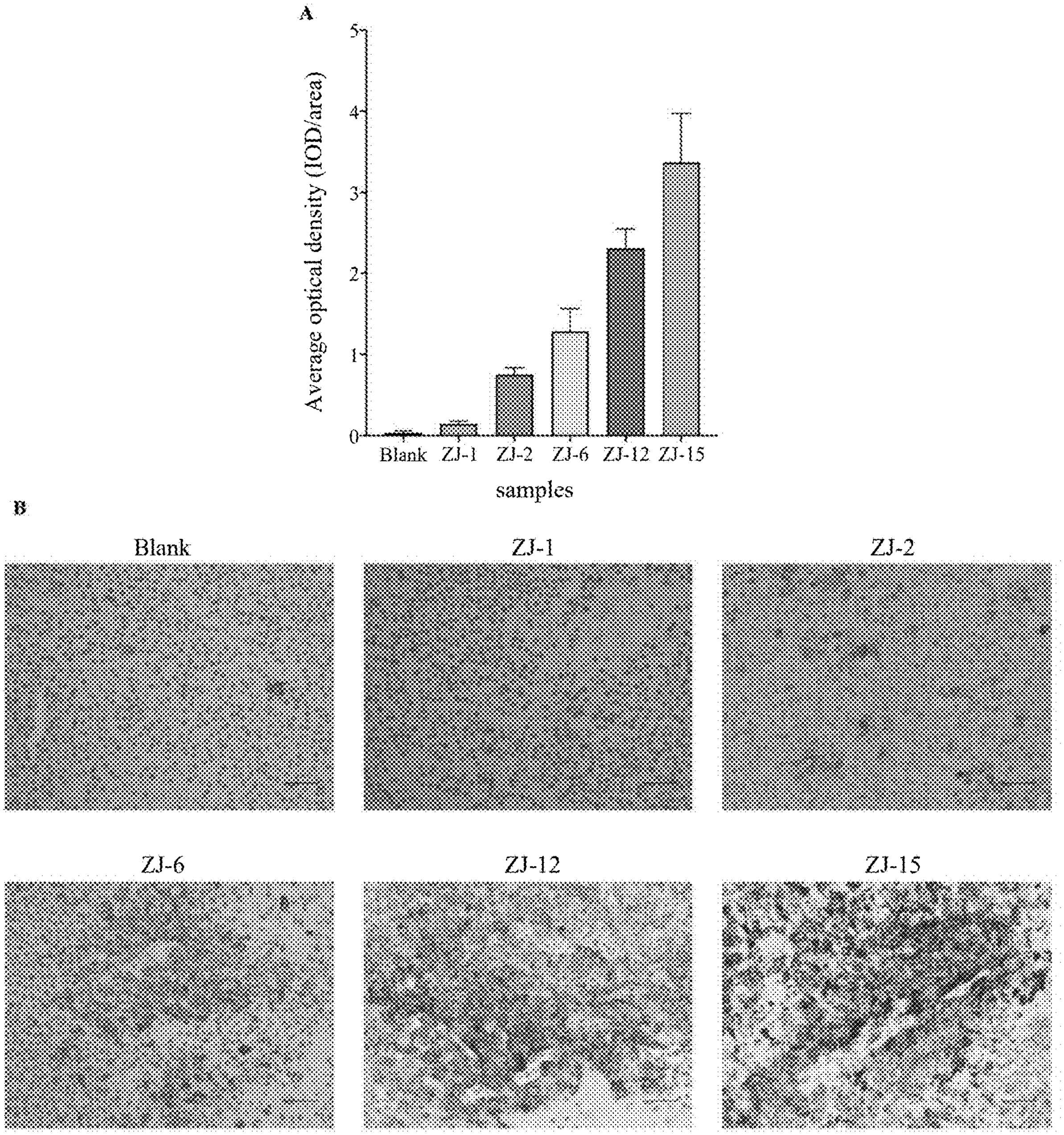
FIG. 17 shows the results of immunohistochemical staining of tumors from different groups of mice; A: mean optical density; and B: representative imaging results.

As shown in FIG. 17A, the degree of invasion of CD8+ T cells induced by these molecules was highly correlated with their anti-tumor activities (see FIGS. 16A and B). The higher the degree of infiltration of CD8+ T cells, the more inhibition to tumor growth. This was consistent with the working mechanism of the fusion polypeptide or polypeptide dimer molecules according to the present disclosure expected by the inventor, that is, the fusion polypeptide or polypeptide dimer molecules according to the present disclosure can activate the body's own immune system to kill tumor tissues in a better way. FIG. 17B showed the immunohistochemical staining photos of some representative tumor sections, which more intuitively showed the infiltration of CD8+ T cells in tumor tissues under the interventions of different molecules, in which blue represented the nucleus, and brown represented the CD8 expression signal. It can be clearly observed that, for example, ZJ-15 molecule induce a large number of CD8+ T cells to enter tumor tissues for killing and inhibition.

The invention claimed is:

1. A fusion polypeptide, comprising an amino acid sequence of one of SEQ ID NOs: 8-11.

2. A pharmaceutical composition, comprising the fusion polypeptide according to claim 1.

3. An isolated polynucleotide, encoding the fusion polypeptide according to claim 1.

4. An expression vector, comprising the polynucleotide according to claim 3.

5. A host cell, comprising the expression vector according to claim 4.

6. A host cell, comprising the polynucleotide according to claim 3.

* * * * *